(12) United States Patent
Jenkins

(10) Patent No.: US 10,285,638 B2
(45) Date of Patent: May 14, 2019

(54) METHODS AND SYSTEMS FOR MEDICATION MONITORING

(71) Applicant: Barry L. Jenkins, Pottsville, PA (US)

(72) Inventor: Barry L. Jenkins, Pottsville, PA (US)

(73) Assignee: CONTINUOUS PRECISION MEDICINE, Research Triangle Park, NC (US)

( * ) Notice: Subject to any disclaimer, the term of this patent is extended or adjusted under 35 U.S.C. 154(b) by 261 days.

(21) Appl. No.: 15/170,501

(22) Filed: Jun. 1, 2016

(65) Prior Publication Data

US 2016/0356763 A1 Dec. 8, 2016

Related U.S. Application Data

(60) Provisional application No. 62/169,756, filed on Jun. 2, 2015, provisional application No. 62/185,568, filed on Jun. 27, 2015.

(51) Int. Cl.
*H05B 33/00* (2006.01)
*A61B 5/00* (2006.01)
(Continued)

(52) U.S. Cl.
CPC .......... *A61B 5/4833* (2013.01); *A61B 5/0075* (2013.01); *A61B 5/02405* (2013.01); *A61B 5/0533* (2013.01); *A61B 5/4848* (2013.01); *A61J 7/00* (2013.01); *A61J 7/0007* (2013.01); *G01J 3/42* (2013.01); *G01N 33/15* (2013.01); *G01N 33/497* (2013.01); *G06F 19/00* (2013.01); *G06N 3/006* (2013.01); *G06N 3/0445* (2013.01);
(Continued)

(58) Field of Classification Search
CPC ................. G01N 33/497; G01N 33/15; A61K 47/48092; A61K 47/48215; A61K 47/48238; A61K 49/0006; A61K 49/006; G16H 50/20; G01J 3/42; G06F 19/00; G06N 5/048
See application file for complete search history.

(56) References Cited

U.S. PATENT DOCUMENTS

| | | | |
|---|---|---|---|
| 6,284,219 B1 * | 9/2001 | Ajami ................ | A61K 51/1206 424/1.11 |
| 2007/0060819 A1 * | 3/2007 | Altshuler ............ | A61B 5/0059 600/475 |

(Continued)

OTHER PUBLICATIONS

Edward Choi, et al., "Doctor AI: Predicting Clinical Events via Recurrent Neural Networks", Learning (cs.LG), arXiv:1511.05942v8 [cs.LG], Version 8, Mar. 19, 2016, 19 pages.

(Continued)

*Primary Examiner* — Kiho Kim
(74) *Attorney, Agent, or Firm* — Oblon, McClelland, Maier & Neustadt, L.L.P.

(57) ABSTRACT

A method of determining whether a patient has taken a dose of medication. The method includes including a first-pass tracer substance with at least one dose of the medication. The first-pass tracer substance is detectable in a body of the patient using a sensor. In addition, the first-pass tracer substance has a short half-life at the site of detection in the body. Further, processing circuitry determines that the patient has taken the dose of medication when the first-pass tracer substance is detected using the sensor at a time after a scheduled medication administration.

8 Claims, 59 Drawing Sheets

(51) Int. Cl.
| | |
|---|---|
| G06N 5/04 | (2006.01) |
| G01J 3/42 | (2006.01) |
| G01N 33/15 | (2006.01) |
| G01N 33/497 | (2006.01) |
| A61B 5/024 | (2006.01) |
| A61B 5/053 | (2006.01) |
| A61J 7/00 | (2006.01) |
| G16H 50/20 | (2018.01) |
| G06F 19/00 | (2018.01) |
| G06N 3/00 | (2006.01) |
| G06N 3/04 | (2006.01) |
| G06N 3/12 | (2006.01) |
| A61B 5/08 | (2006.01) |
| A61B 5/16 | (2006.01) |

(52) U.S. Cl.
CPC .............. *G06N 3/12* (2013.01); *G06N 5/048* (2013.01); *G16H 50/20* (2018.01); *A61B 5/082* (2013.01); *A61B 5/165* (2013.01); *A61B 5/4845* (2013.01); *A61B 5/742* (2013.01)

(56) References Cited

U.S. PATENT DOCUMENTS

2010/0272652 A1* 10/2010 Levinson ......... A61K 47/48092
424/9.8
2011/0181410 A1* 7/2011 Levinson ............ G06F 19/3456
340/540
2012/0039809 A1* 2/2012 Levinson ........... A61B 10/0045
424/9.1
2017/0095184 A1* 4/2017 Heikenfeld .......... A61B 5/6831

OTHER PUBLICATIONS

Andrew R. Joyce, et al., "Modeling the onset of drug dependence: A consideration of the requirement for protein synthesis", Journal of Theoretical Biology, vol. 240, 2006, pp. 531-537.

Robert B. Raffa, et al., "Modified 'Joyce model' of opioid dependence/withdrawal", Eur. J. Pharmacol., vol. 551, No. 1-3, Dec. 3, 2006, 7 pages.

Lingjiong Zhu, "Nonlinear Hawkes Processes", Probability (math.PR), arXiv:1304.7531v3 [math.PR], Version 3, Jun. 23, 2013, 218 pages.

Veenu Mangat, "Swarm Intelligence Based Technique for Rule Mining in the Medical Domain", International Journal of Computer Applications (0975-8887), vol. 4, No. 1, Jul. 2010, pp. 19-24.

Abraham Peper, "A theory of drug tolerance and dependence II: the mathematical model", Journal of Theoretical Biology, vol. 229, 2004, pp. 491-500.

* cited by examiner

FIG. 1C
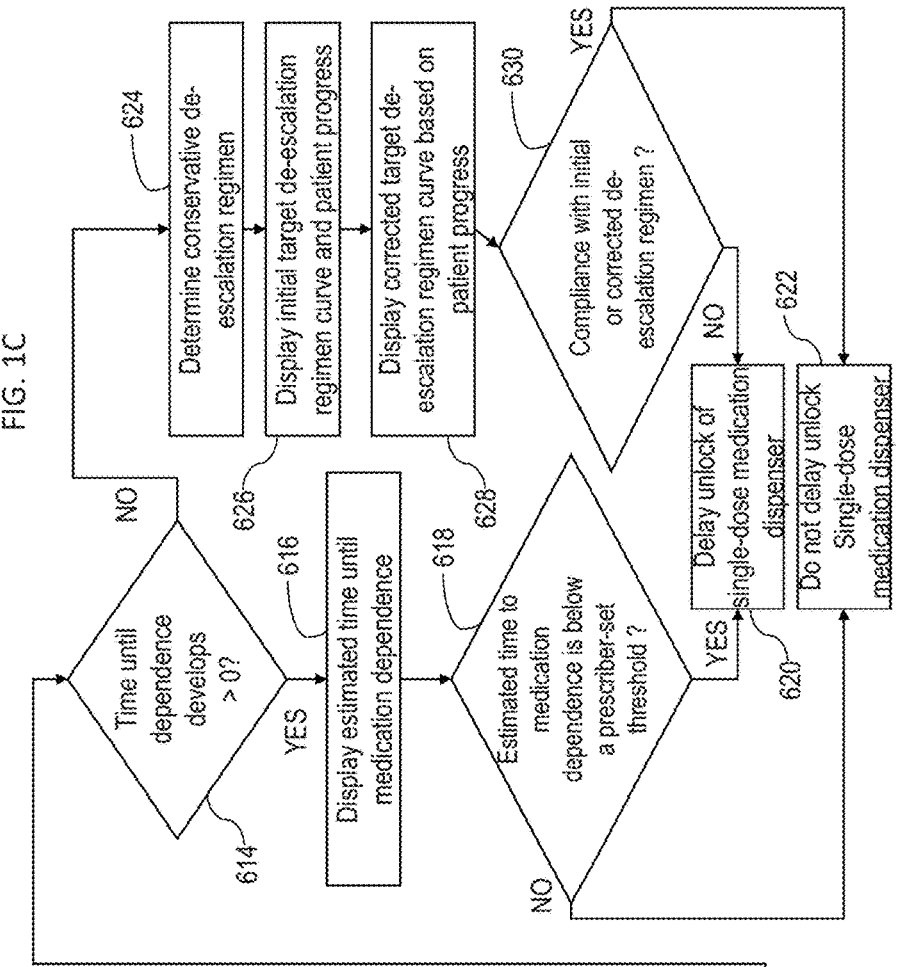
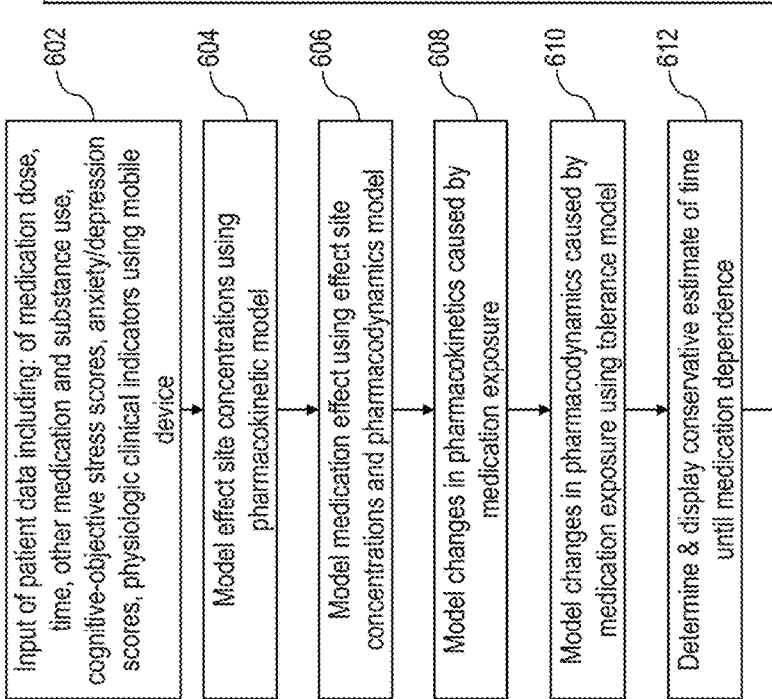

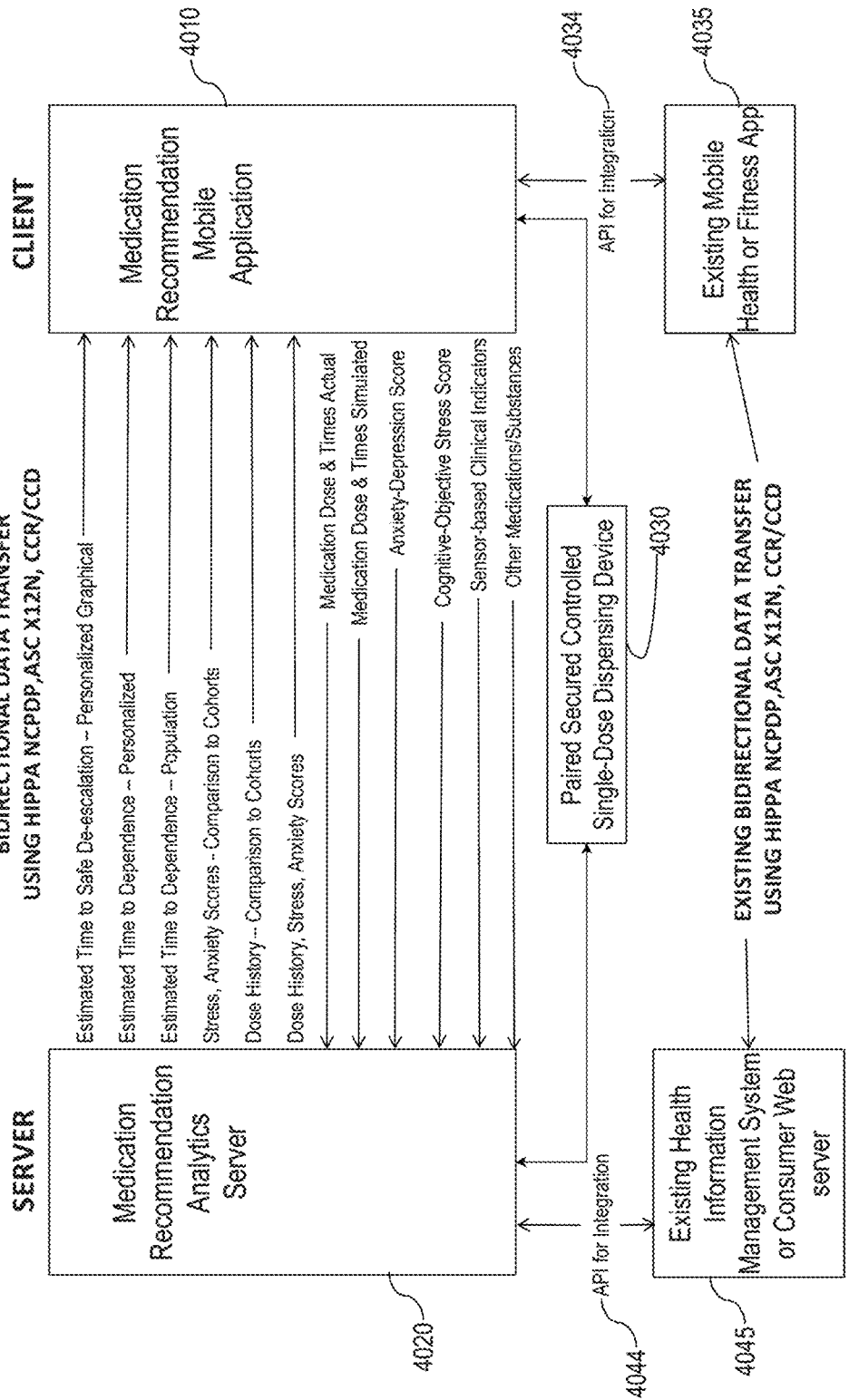

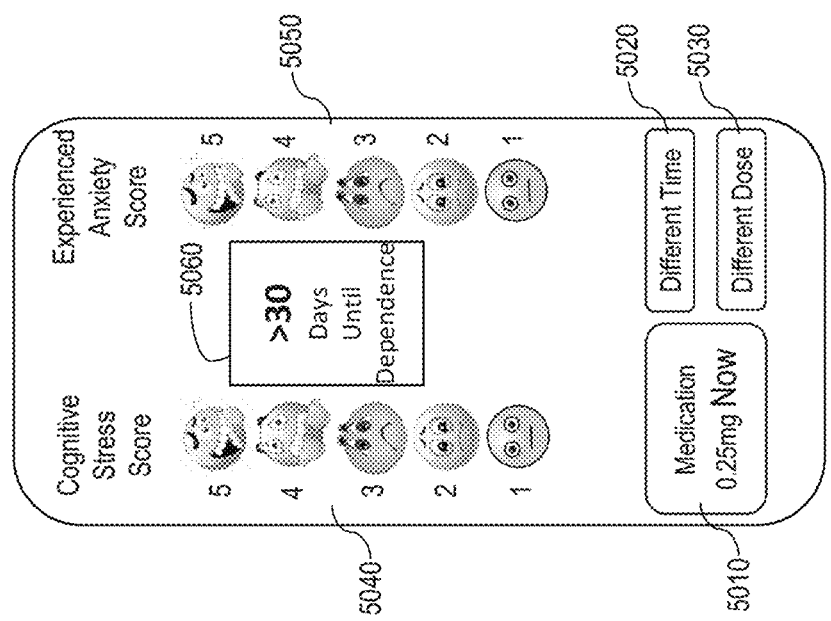

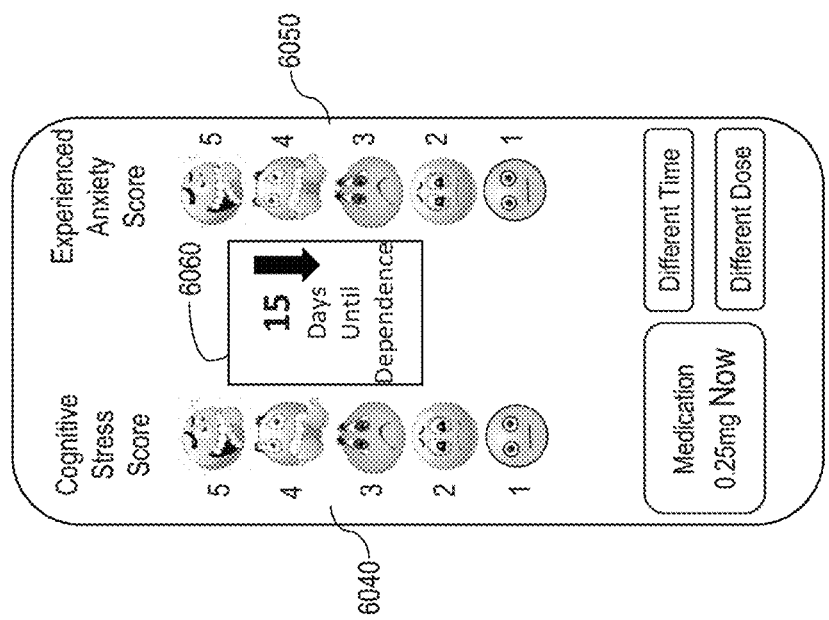

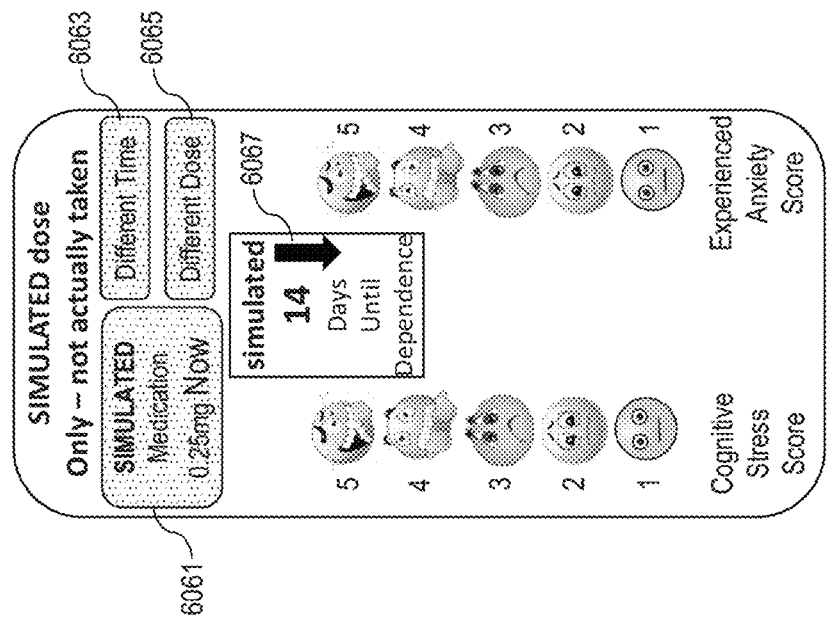

Yerkes-Dodson Curve – Performance Anxiety
PRIOR ART

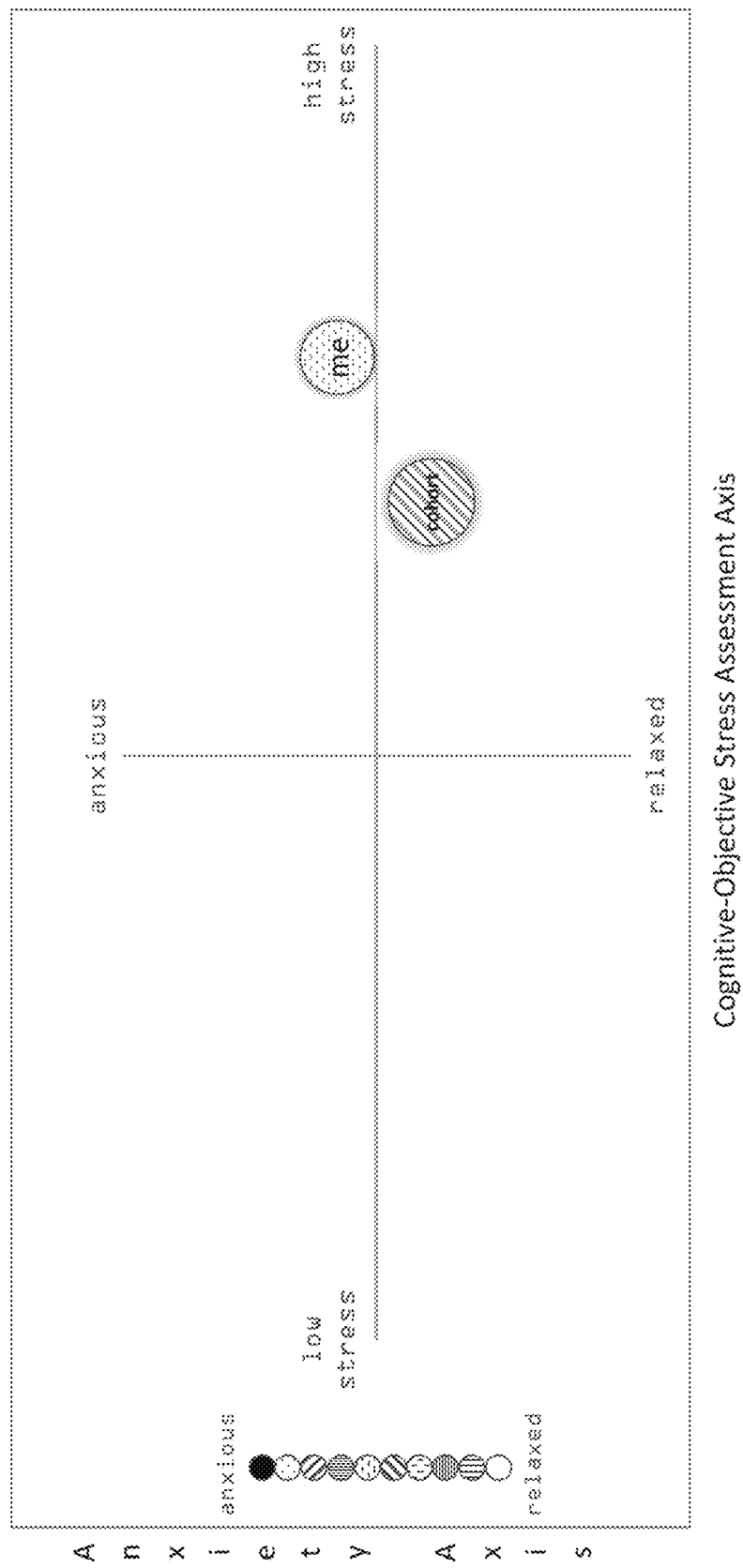

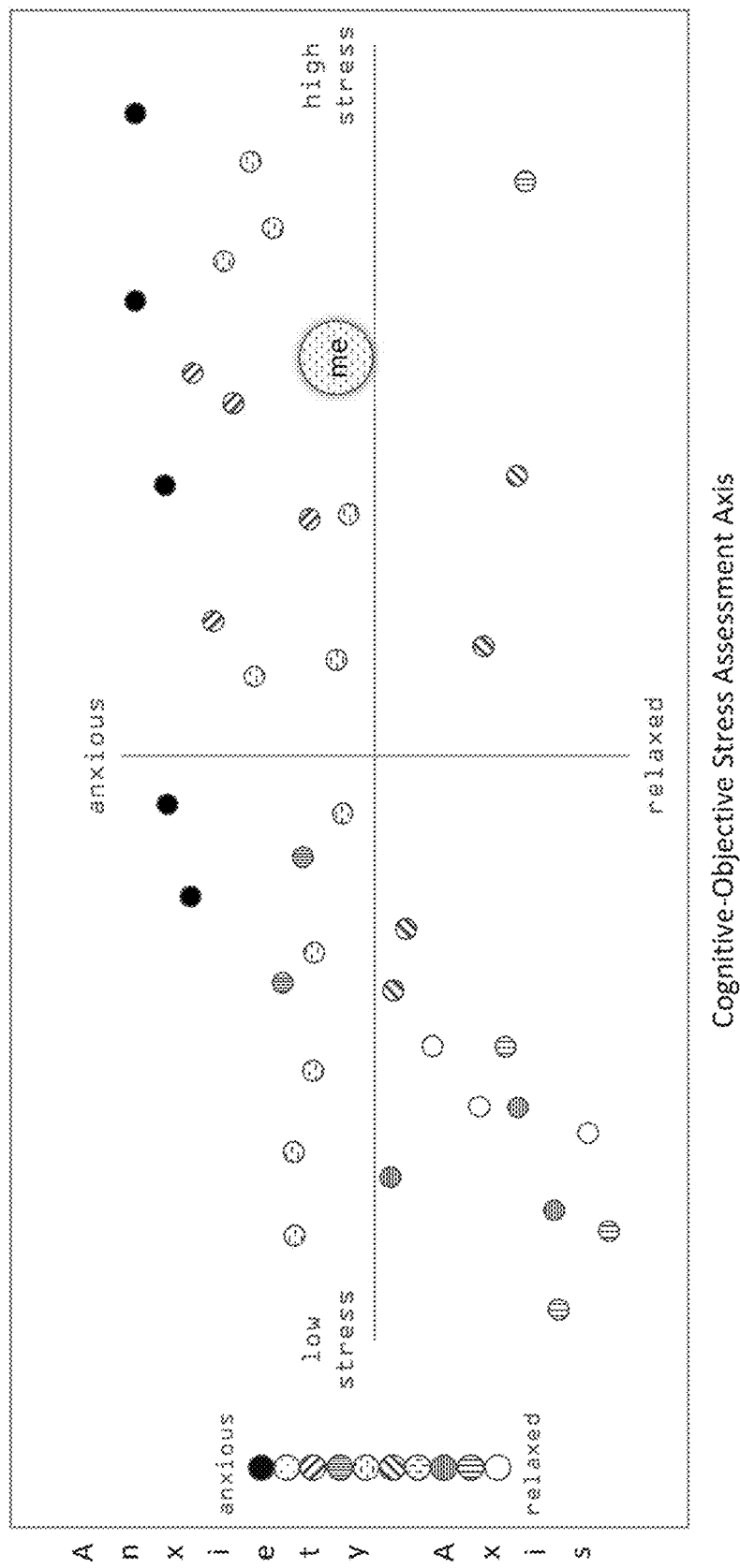

Zero Tablets Dispensed

Bottom Level

Side View

Upper Level

Upper Level

One Tablet Dispensed

Side View

Bottom Level

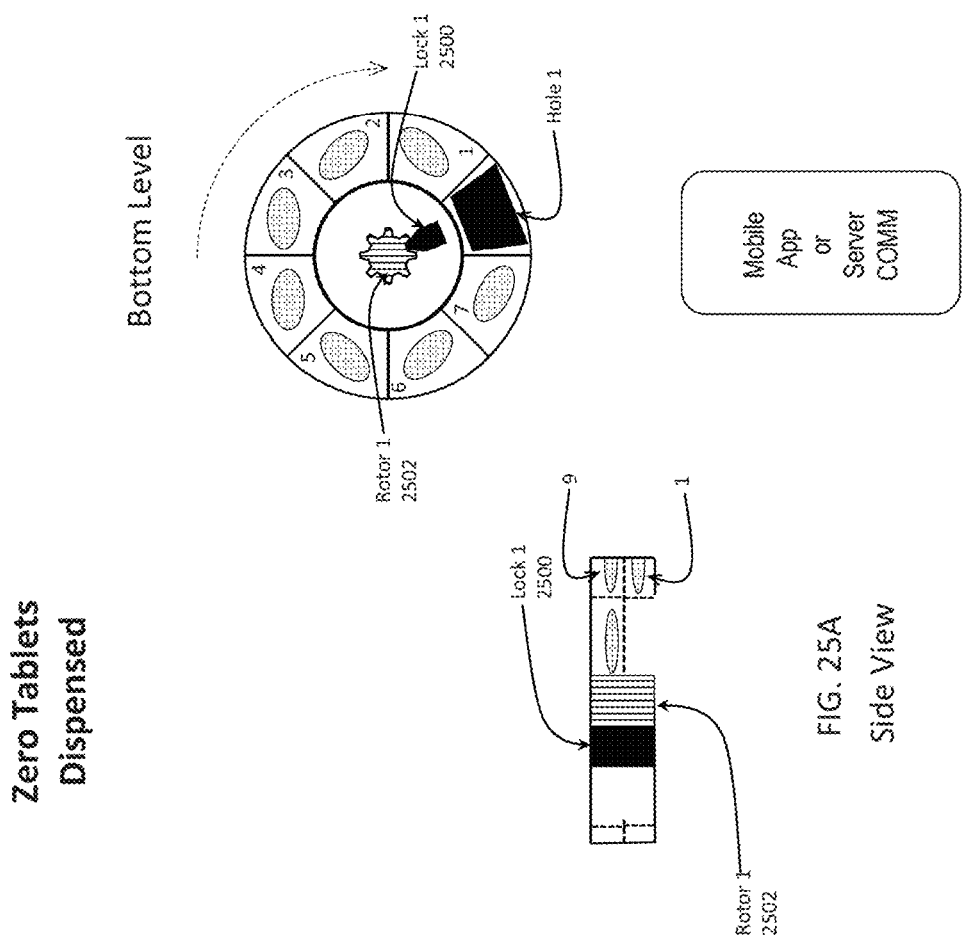

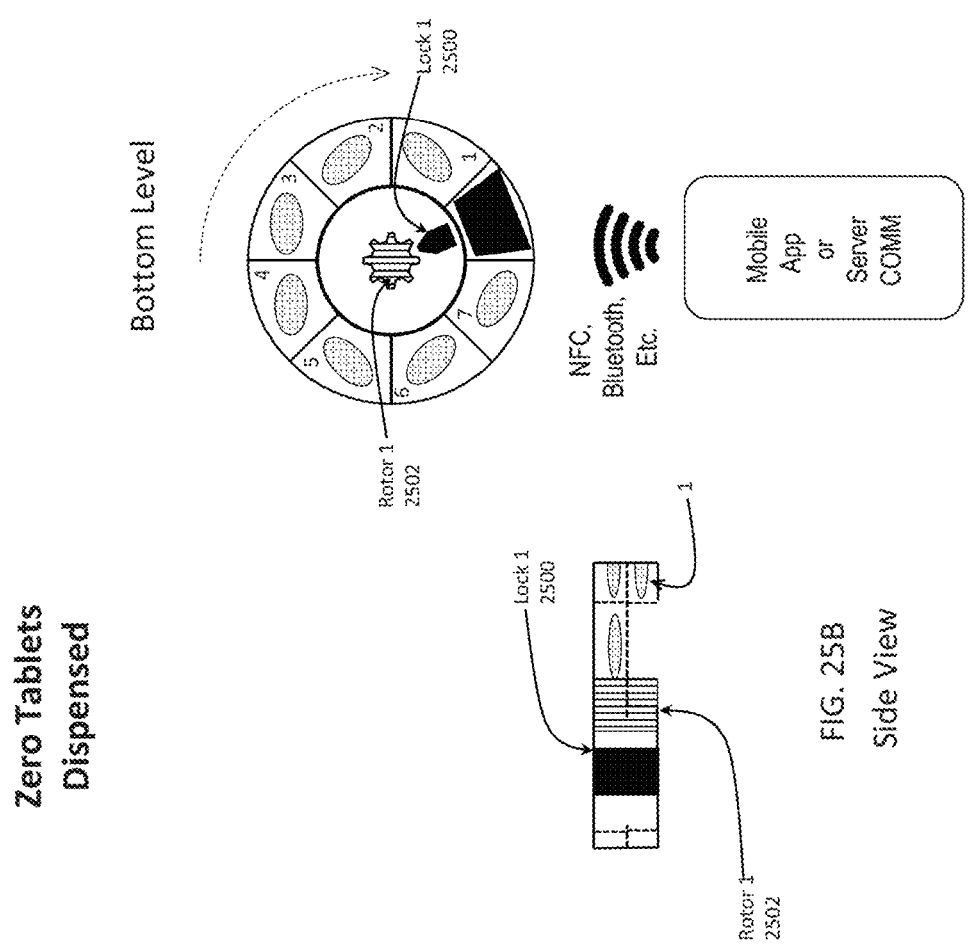

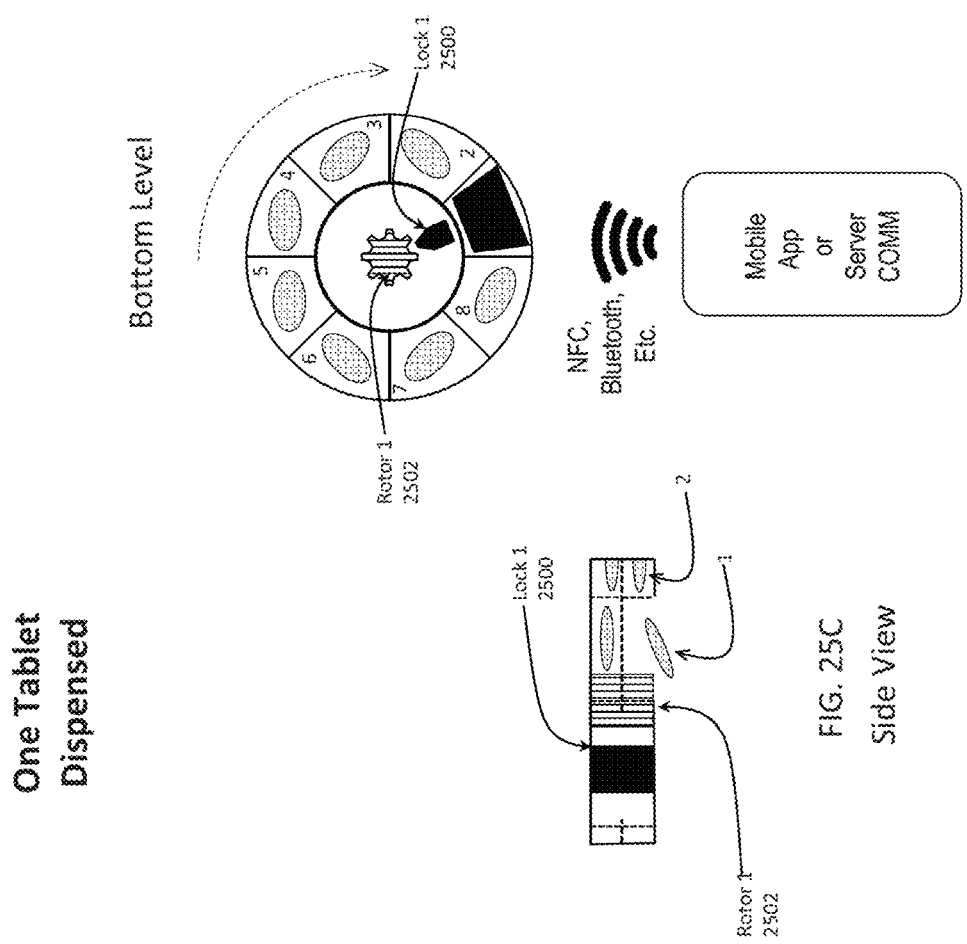

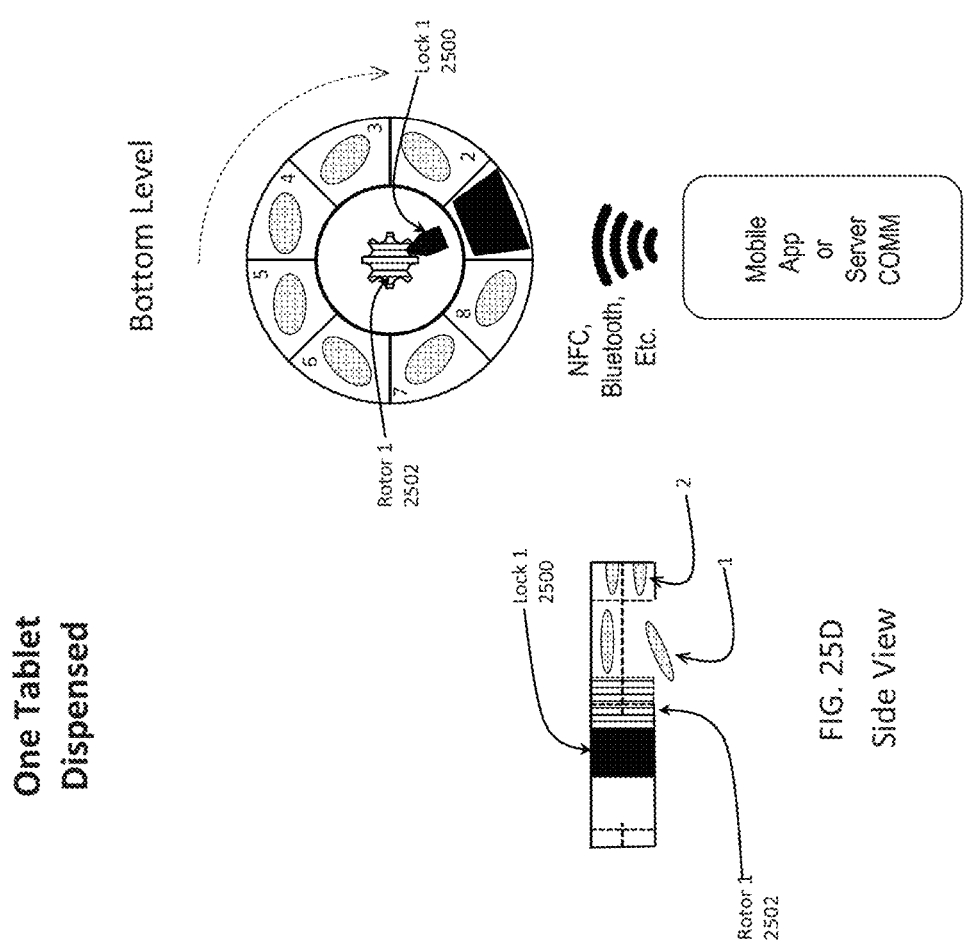

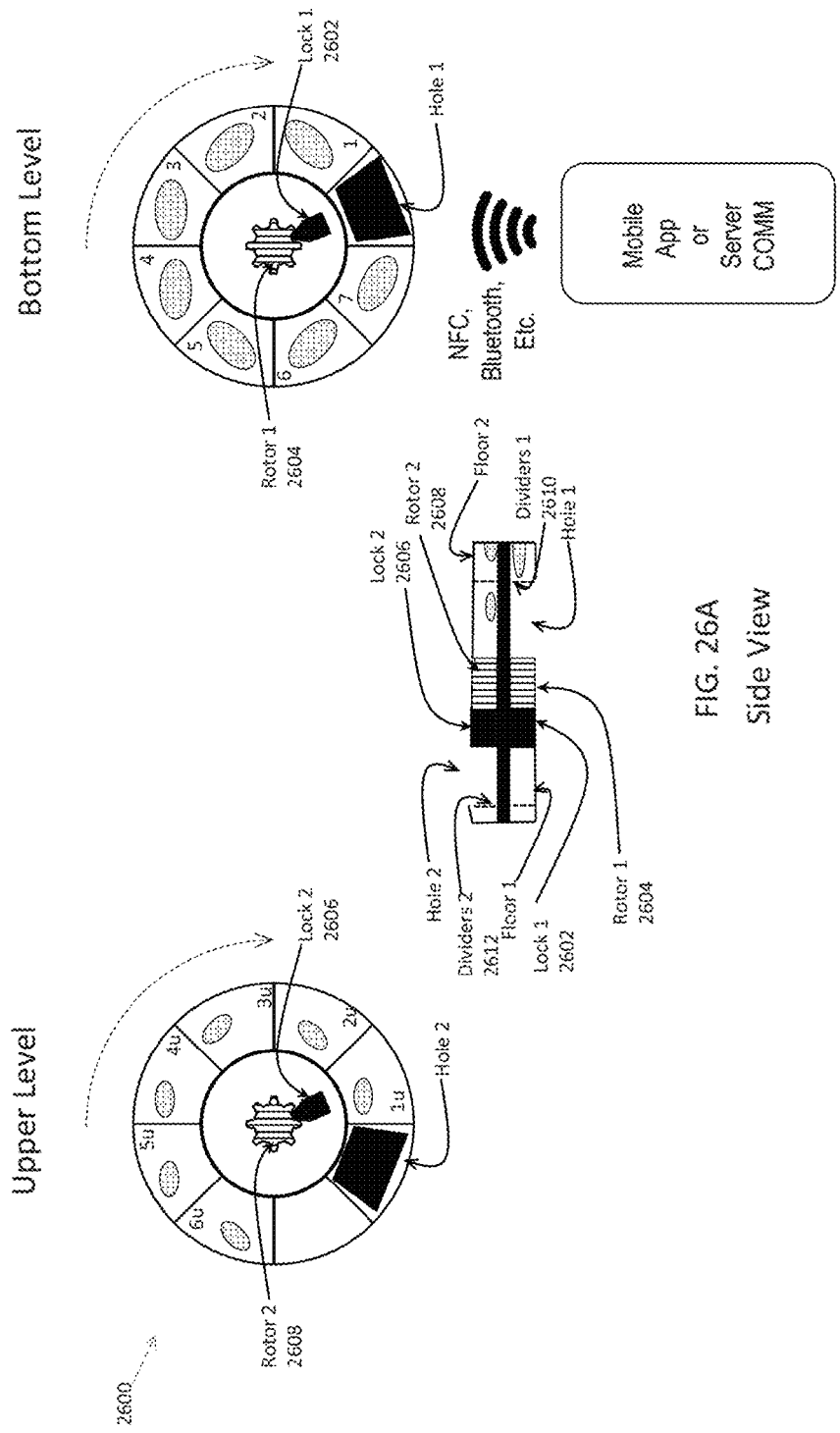

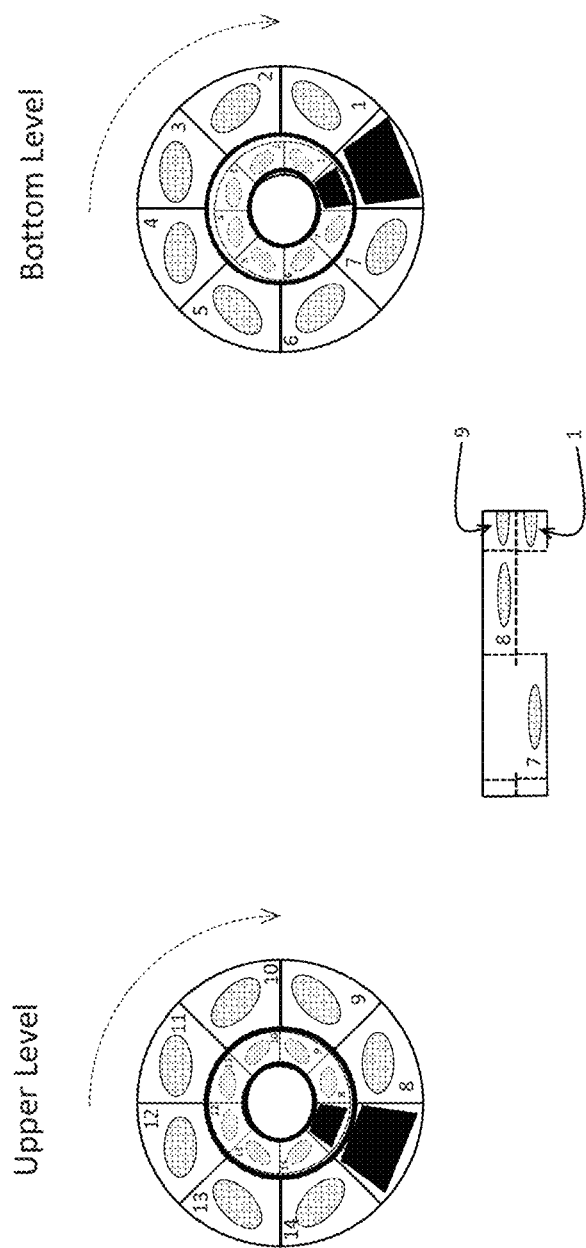

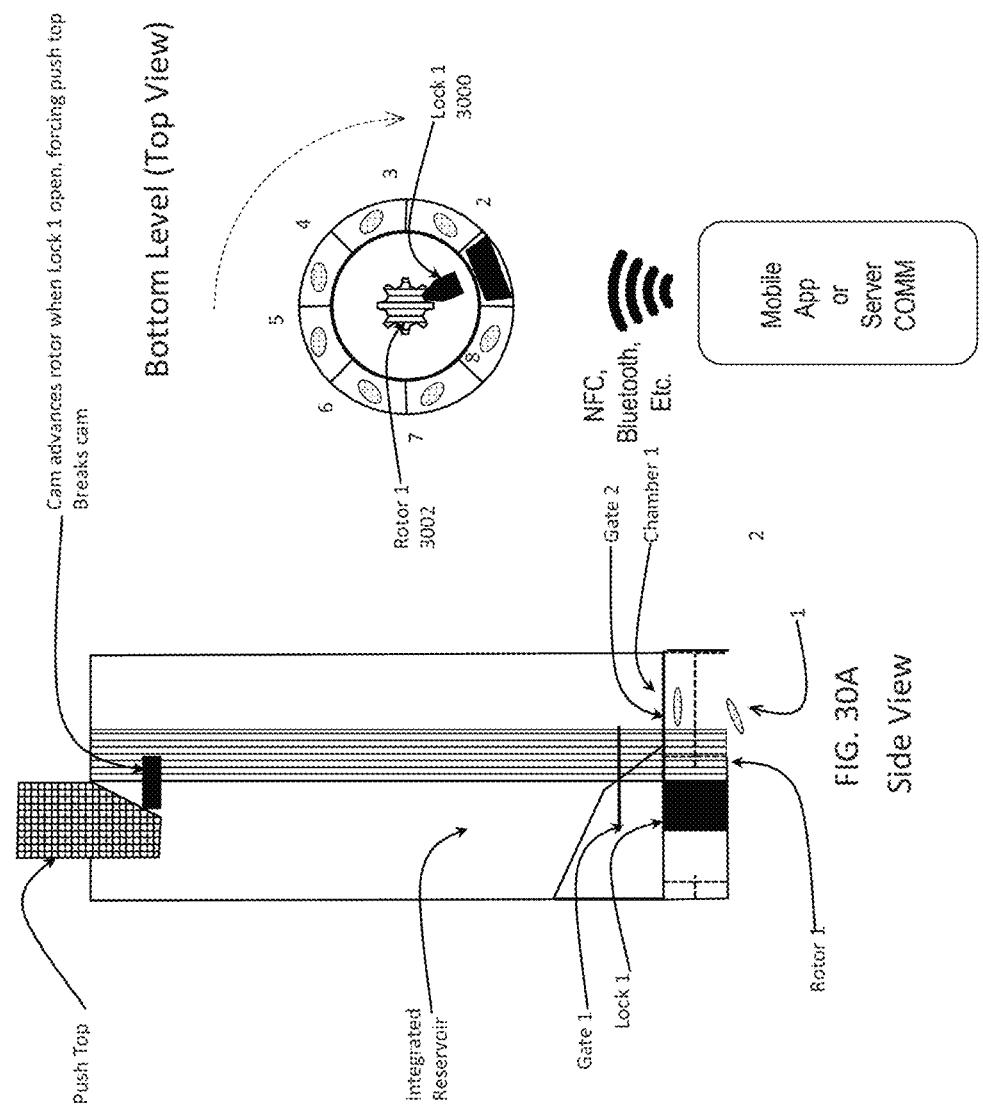

Gated Manual Shake Design

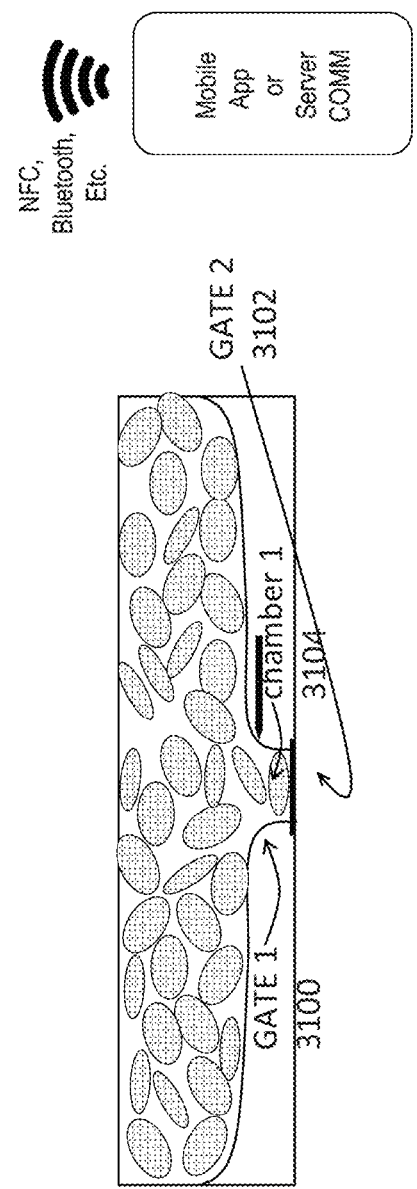

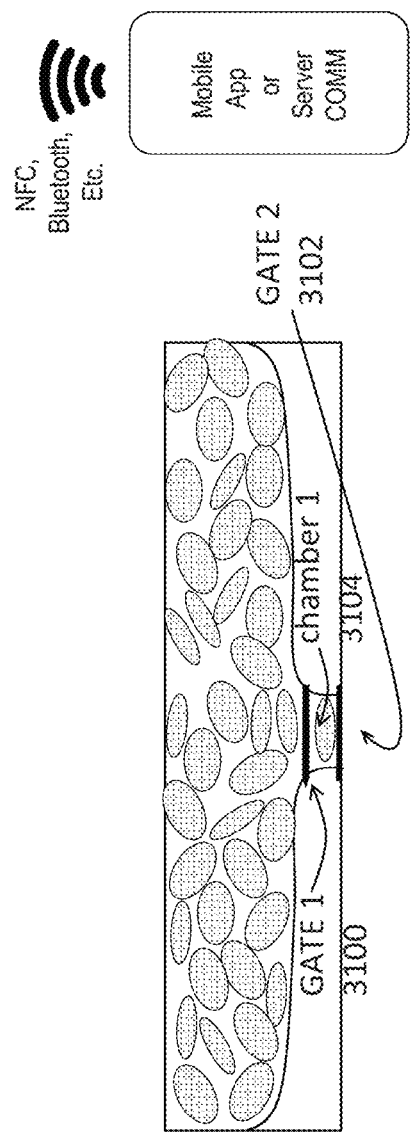

Homeostatic Model of Medication Tolerance

PRIOR ART

FIG. 35B
Receptor-Induction Model of Medication Tolerance $$W_t / W_{50} = (1 - e^{-\alpha t}) + (1 - e^{-\beta(t+\delta)}).$$

PRIOR ART

FIG. 35C

Scoring Patient Assessment for Anxiety

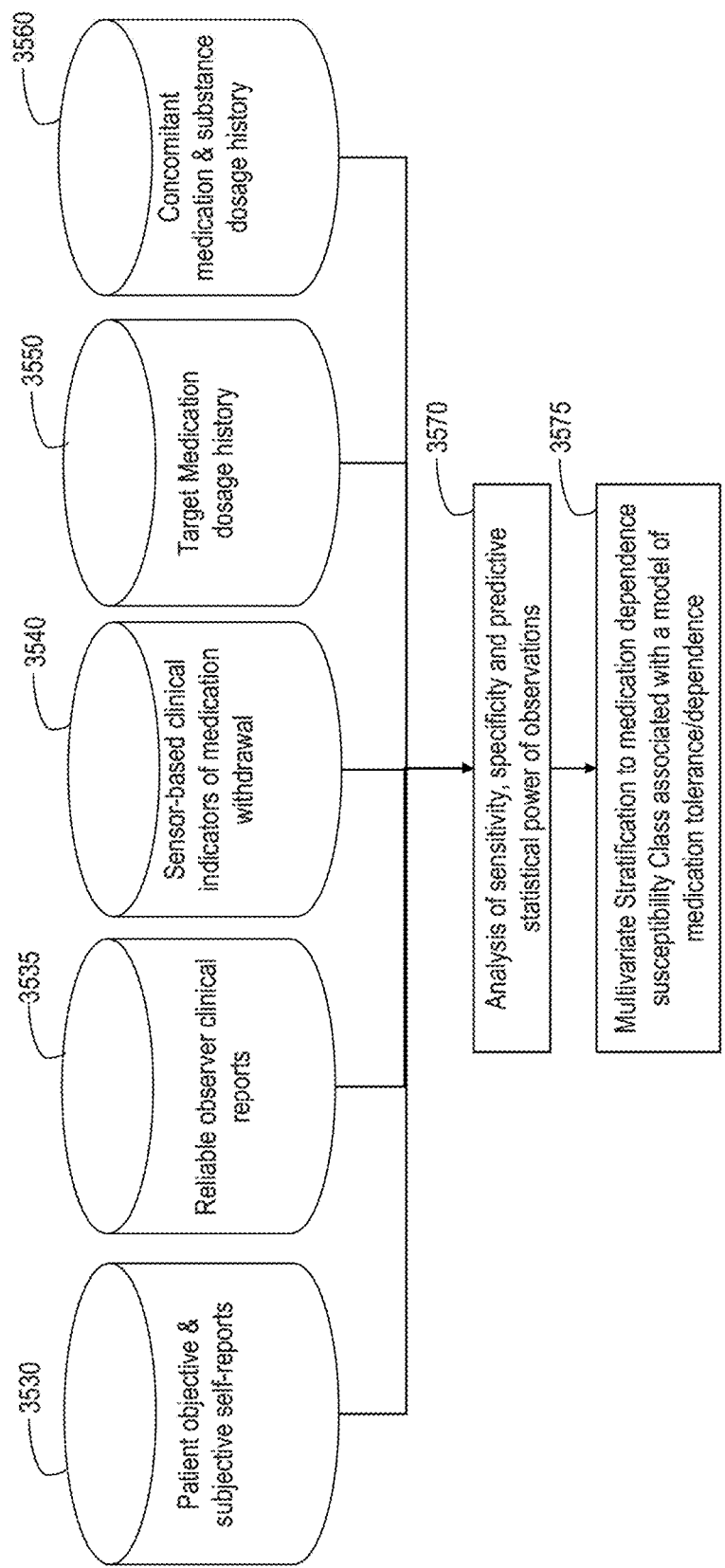

PRIOR ART

FIG. 35G

Scoring Patient Assessment for Anxiety

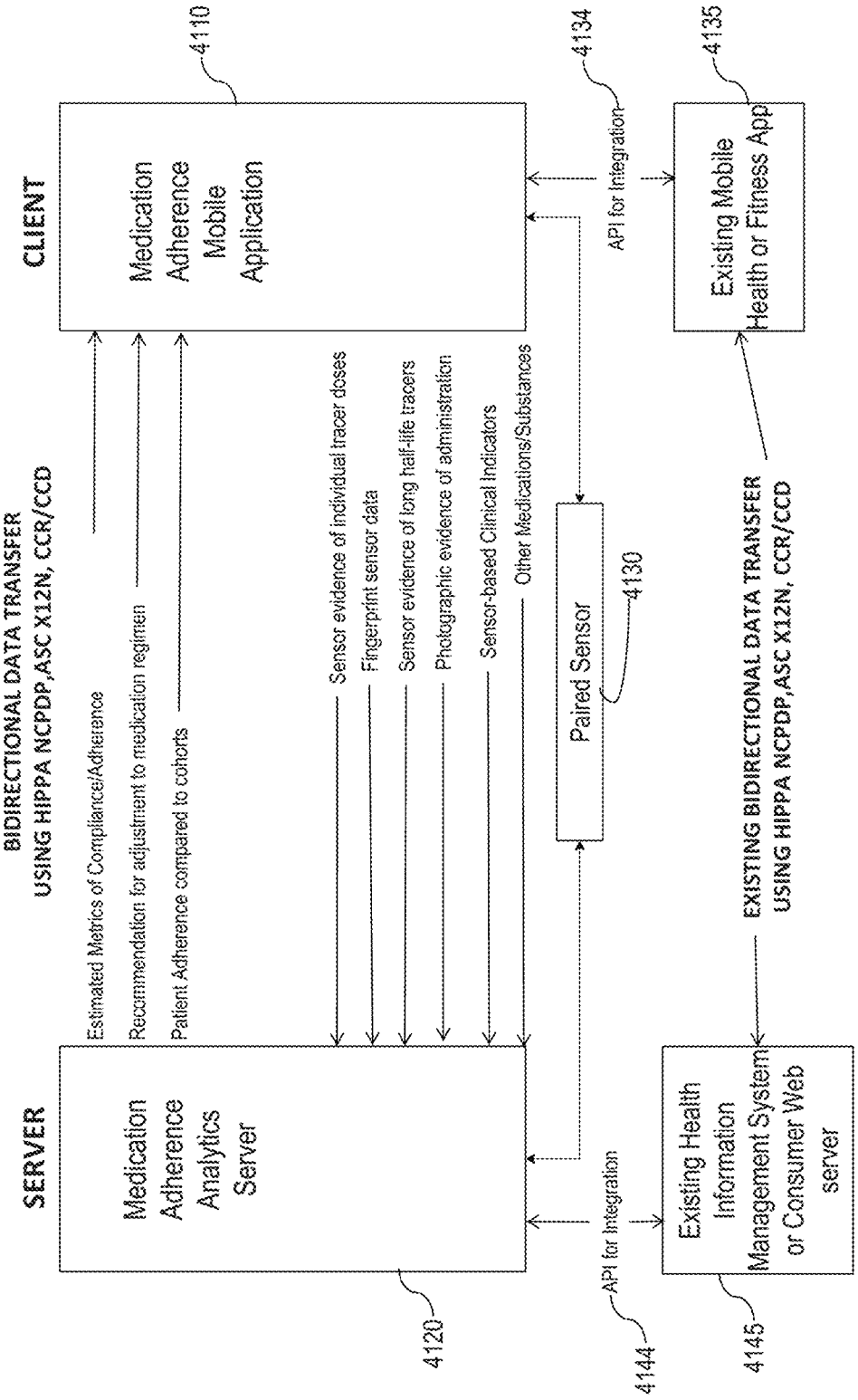

METHODS AND SYSTEMS FOR MEDICATION MONITORING

CROSS-REFERENCE TO RELATED APPLICATIONS

This application claims the benefit of priority under 35 U.S.C. § 119(e) to U.S. Provisional Application No. 62/169,756 filed on Jun. 2, 2015, the entirety of which is incorporated herein by reference. This application also claims the benefit of priority under 35 U.S.C. § 119(e) to U.S. Provisional Application No. 62/185,568 filed on Jun. 27, 2015, the entirety of which is incorporated herein by reference.

FIELD

This application relates generally to the field of pharmacology and drug administration. In particular, disclosed embodiments relate to systems and methods for using clinical observations and pharmacological models to make recommendations for medication management. More specifically, these systems and methods are used for determining and presenting dosing guidelines which reduce the risk of drug tolerance and dependence, and which improve adherence to prescribed medication regimens.

BACKGROUND

For most drugs, proper dosing is complicated by several factors. First, the time course of drug levels over time varies from patient to patient. This is termed pharmacokinetic uncertainty. Second, the drug level that corresponds to a desired clinical effect varies from patient to patient. This is termed pharmacodynamics uncertainty. Third, patients can develop tolerance and dependence to medications if the effect-site is exposed to the drug at sufficient concentrations over sufficient time.

Many commonly prescribed medications can lead to tolerance (requiring an increasing larger dose to achieve the same effect) and dependence (experience withdrawal symptoms when the medication is discontinued or the dose is reduced). For example, certain members of benzodiazepine class of medications used to treat anxiety can lead to tolerance and dependence within weeks of initiating therapy.

Unfortunately, these and other medications that can lead to tolerance and dependence are often prescribed as "PRN" ("as needed") medications, a prescription which gives the patient substantial discretion in deciding on the timing (and sometimes the amount) of each dose taken. Even when dosing limits are included in the PRN prescription, this flexibility often leads to escalating dosages which can result in medication tolerance and dependence.

In contrast, other medications (e.g., antipsychotic medications, immunosuppressant medications etc.) tend to be underused by patients which can lead to therapeutic failures caused by poor adherence to prescribed medication regimens.

The foregoing "Background" description is for the purpose of generally presenting the context of the disclosure. Work of the inventor, to the extent it is described in this background section, as well as aspects of the description which may not otherwise qualify as prior art at the time of filing, are neither expressly or impliedly admitted as prior art against the present invention. The foregoing paragraphs have been provided by way of general introduction, and are not intended to limit the scope of the following claims. The described embodiments, together with further advantages, will be best understood by reference to the following detailed description taken in conjunction with the accompanying drawings.

SUMMARY

In an exemplary aspect, a method of determining whether a patient has taken a dose of medication, the method includes including a first-pass tracer substance with at least one dose of the medication. The first-pass tracer substance is detectable in a body of the patient using a sensor, and the first-pass tracer substance has a short half-life at the site of detection in the body. The method also includes determining, using processing circuitry, that the patient has taken the dose of medication when the first-pass tracer substance is detected using the sensor at a time after a scheduled medication administration.

In some exemplary aspects, a method of determining whether a patient has taken a dose of medication, includes including a first-pass tracer substance with at least one dose of the medication. The first-pass tracer substance is detectable in the body of the patient using a sensor, and the first-pass tracer substance has a short half-life at the site of detection in the body by the sensor. The method also includes detecting, using the sensor, the first-pass tracer substance at a time after a scheduled medication administration, recording, using processing circuitry, at the scheduled medication administration, at least one image of the patient taking the dose of the medication, and determining, using the processing circuitry, an increased probability that the patient has taken the dose of medication when the first-pass tracer substance is detected by the sensor and the detection correlates with the at least one image.

In some exemplary aspects, a method of determining whether a patient has taken a dose of a medication, includes including a primary first-pass tracer substance with at least one first dose of the medication. The primary tracer substance is detectable in the body of the patient using a sensor, and the first-pass tracer substance has a short half-life at the site of detection in the body by the sensor. The first dose of medication has a first unique indicator indicating that the first dose of medication contains the primary first-pass tracer substance. The method also includes detecting, using the sensor, the primary first-pass tracer substance at a time after the medication dose containing the primary first-pass tracer substance is scheduled to be taken by the patient. Further, the method includes including a secondary first-pass tracer substance with at least one second dose of the medication. The secondary first-pass tracer substance is detectable in the body using the sensor, and the secondary first-pass tracer substance has a short half-life at the site of detection in the body by the sensor, and the at least one second dose of medication has a second unique indicator indicating that the at least second dose of medication contains the secondary first-pass tracer. The method also includes detecting, using the sensor, the secondary first-pass tracer substance at a time after the medication dose containing the secondary first-pass tracer substance should have been taken by the patient, recording, using processing circuitry, at the time that the patient takes the dose of the medication, a unique indicator of the dose of medication indicating that the dose of medication contains the primary tracer substance or the secondary tracer substance, matching, using the processing circuitry, a result of the detection by the sensor to the unique indicator on the dose of medication, and outputting, using the processing circuitry, a negative result when the result of the detection and the unique indicator does not match indicating the patient did not take the dose of medication.

In some exemplary aspects, a method of determining whether a patient is adhering to a prescribed medication regimen, includes including a first-pass tracer substance with at least one dose of the medication. The first-pass tracer substance being detectable in the body of the patient using a first sensor, and the first-pass tracer substance having a short half-life at the site of detection in the body. The method also includes detecting, using the first sensor, the first-pass tracer substance at a first plurality of times after the medication containing the first-pass tracer substance has been taken by the patient and including a long half-life tracer substance with at least one dose of the medication. The long half-life tracer substance being detectable in the body using a second sensor. The long half-life tracer substance having a long half-life at the site of detection in the body. The method also includes detecting, using the second sensor, the long half-life tracer substance at a second plurality of times, and determining, using processing circuitry, an increased probability that the patient is adhering to the prescribed medication regimen when the number of times the first-pass tracer substance was detected corresponds to a number of scheduled doses during a detection period and the long half-life tracer substance is detected at least a predetermined number of times during the detection period.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1C is an exemplary flowchart illustrating a method for enforcing a dosage schedule using a conservative computer-implemented model of medication dependence and a locked single-dose dispensing device that is electronically paired to the computer-implemented model, according to certain exemplary aspects;

FIG. 4 is an exemplary diagram showing a method of estimating medication tolerance-dependence implemented as a distributed client-server system;

FIG. 5 is an exemplary diagram showing display of a scale for objective, cognitive scoring of the stressfulness of a current situation; a scale for scoring the current level of anxiety; display of buttons for entering medication dose and time; and display of a conservative estimate of the time until medication dependence for a case in which dependence is currently estimated to occur in more than 30 days;

FIG. 6A is an exemplary diagram showing display of a scale for objective, cognitive scoring of the stressfulness of a current situation; a scale for scoring the current level of anxiety; display of buttons for entering medication dose and time; and display of a conservative estimate of the time until medication dependence for a case in which dependence is currently estimated to occur in 15 days and the time until dependence is decreasing;

FIG. 6E is an exemplary diagram showing display of buttons for entering a simulated medication dose, which is a dose not actually taken by the patient but which is entered in order to determine the effect of the simulated dose or doses on the conservative estimate of the time until medication dependence;

FIG. 21 is an exemplary scatter plot showing the display of average anxiety score vs. the average cognitive-objective stress assessment score for an individual compared to the average for the individual's cohort;

FIG. 22 is an exemplary scatter plot showing the display of average anxiety score vs. the average cognitive-objective stress assessment score for an individual compared to the other individuals within the cohort;

FIG. 25A is an exemplary diagram showing additional elements of a single-dose dispensing device including a locking mechanism and a paired electronic device;

FIG. 25B is an exemplary diagram showing additional elements of a single-dose dispensing device including a locking mechanism and a paired electronic device which has opened the single-dose locking device using a wireless signal;

FIG. 25C is an exemplary diagram showing additional elements of a single-dose dispensing device including a locking mechanism and a paired electronic device which has opened the single-dose locking device using a wireless signal allowing the single-dose dispensing device to be moved to the next rotational position and thereby enabling dispensation of a single dose of the medication;

FIG. 25D is an exemplary diagram showing the single-dose dispensing device returned to a default locked state after dispensation of the single dose of medication;

FIG. 26A is an exemplary diagram showing a locked, secure, single-dose medication dispensing device that is paired to and controlled by a Mobile app or Server, and having two independent rotary sweep mechanisms capable of being unlocked independently;

FIG. 26B is an exemplary diagram showing elements of a single-dose dispensing device having an outer dispensing ring and at least one inner dispensing ring;

FIG. 30A is an exemplary diagram showing a tubular embodiment of a portable secure, paired single-dose medication dispensing device employing a hybrid gravity feed with gates and a cascade feed with floor holes, and using a push top which motivates a cam driving an unlocked rotor;

FIG. 32 is an exemplary diagram showing a secure-single dose medication dispensing device using a shake-facilitated feed into a lock chamber controlled by two gates, in a second stage of lock chamber operation;

FIG. 33 is an exemplary diagram showing a secure-single dose medication dispensing device using a shake-facilitated feed into a lock chamber controlled by two gates, in a third stage of lock chamber operation;

FIG. 35B is an exemplary diagram of a known method of modeling medication tolerance using a model of receptor induction;

FIG. 35C is an exemplary known patient assessment for patient stress and anxiety;

FIG. 35D is an exemplary flow diagram showing a method of expert prescriber system which incorporates patient dosage history, patient history of concomitant medication and substance use, patient self-reports and self-monitoring data, as well as clinical indicators from reliable observers and sensor evidence of potential medication withdrawal signs in order to classify or reclassify a patient into s medication dependence susceptibility class associated with a model of medication tolerance/dependence;

FIG. 35G is an exemplary known patient assessment for patient stress and anxiety;

FIG. 40 is an exemplary diagram showing a method of monitoring patient adherence to a medication regimen using detectable tracers in medications implemented as a distributed client-server system.

DETAILED DESCRIPTION

Figure 1A:
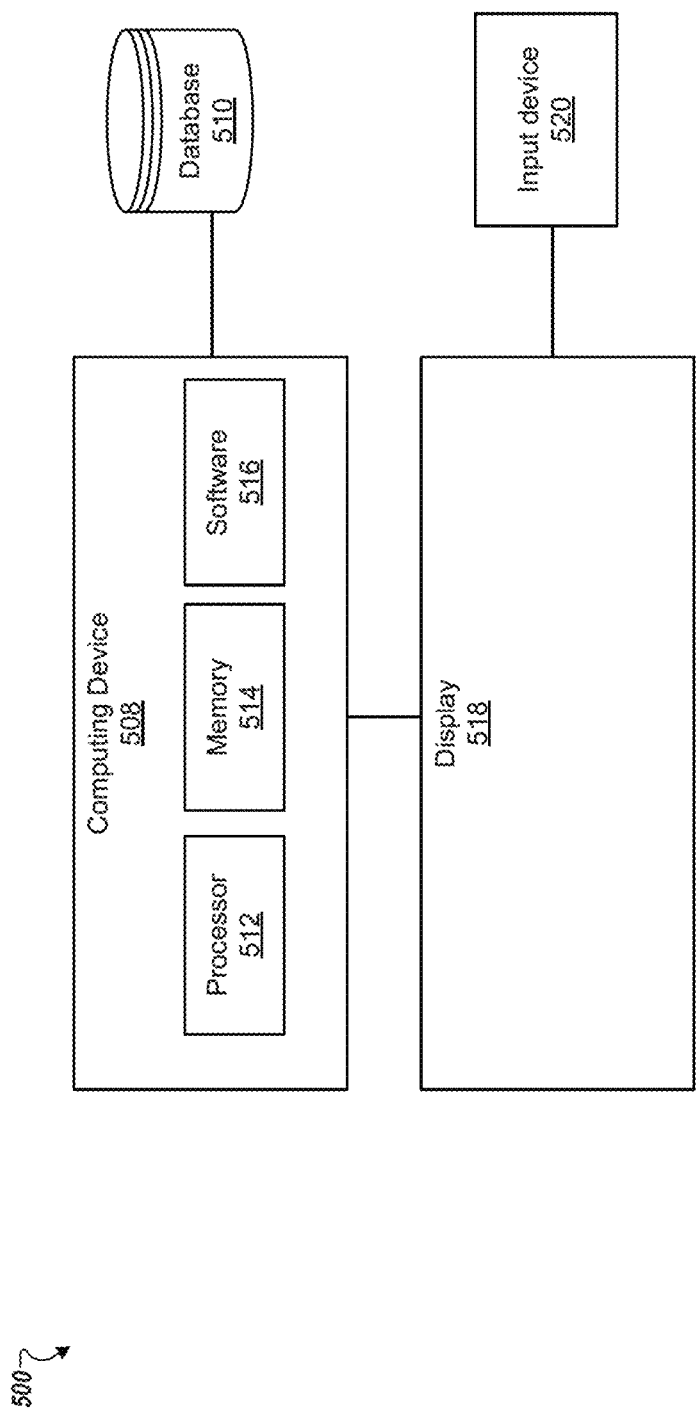
FIGS. 1A and 1B are exemplary schematic diagrams illustrating systems for recommending dose and time of medication administrating, according to certain exemplary aspects.

Referring now to the drawings, wherein like reference numerals designate identical or corresponding parts throughout several views, the following description relates to systems and associated methodologies for managing a risk of medication dependence.

In the following description, various exemplary embodiments are described. For purposes of explanation, specific configurations and details are set forth in order to provide a thorough understanding of the embodiments. However, it will also be apparent to one skilled in the art that the embodiments may be practiced without the specific details presented herein. Furthermore, well known features may be omitted or simplified in order not to obscure the embodiments.

Unless specifically stated otherwise, as apparent from the following discussions, it is appreciated that throughout the specification discussions utilizing terms such as "processing," "computing," "calculating," "determining," or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Figure 1B:
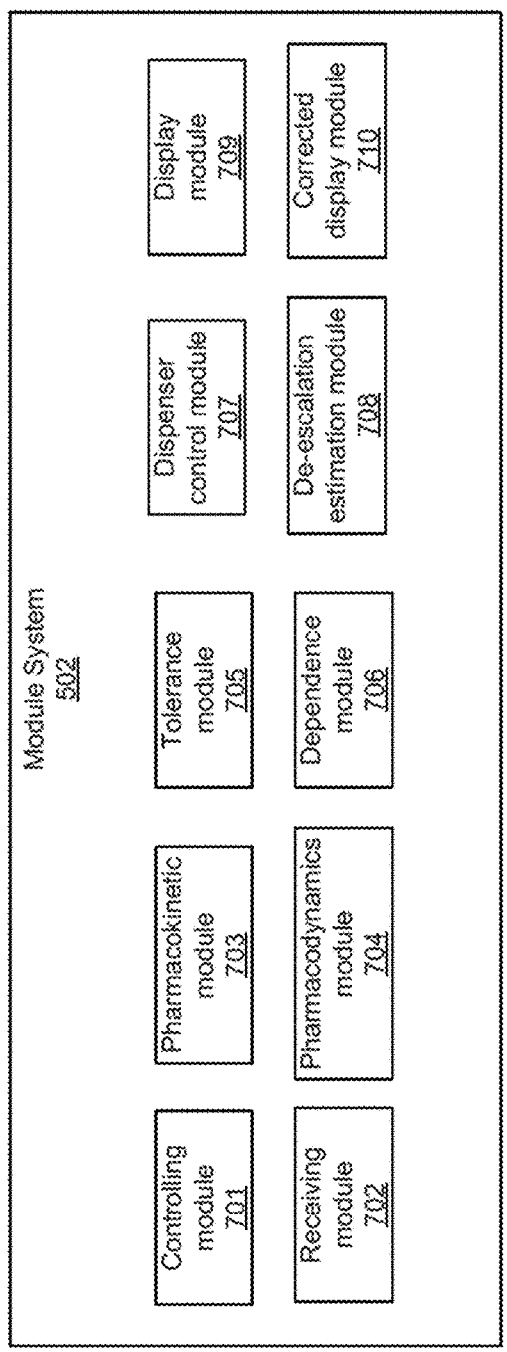

FIGS. 1A and 1B schematically illustrate examples of a system 500 for providing dosing recommendations and for controlling a secure single-dose administration device. Although the FIGS. 1A and 1B show an exemplary conventional general-purpose digital environment, it will be understood that other computing environments may also be used. For example, one or more embodiments may use an environment having fewer than or otherwise more than all of the various aspects shown in FIGS. 1A and 1B, and these aspects may appear in various combinations and sub-combinations that will be apparent to one of ordinary skill in the art.

As shown in FIG. 1A, system 500 may include a computing device 508. Computing device 508 may include, for example, any suitable processing system, computing system, computing device, processing device, computer, processor, or the like, and may be implemented using any suitable combination of hardware and/or software. Computing device 508 may include for example one or more processor(s) 512, memory 514, and software 516. Data may be transferred, for example, to computing device 508. The data may be stored in the memory 514 as for example digital information and transferred to computing device 508 by uploading, copying, or transmitting the digital information. Processor 504 may communicate with computing device 508 via wired or wireless command and execution signals.

In certain aspects, using a matching method, computing device 508 may include units, modules, means, and circuitry for various steps described herein for recommending a drug dose and timing and for controlling a single-dose administration device.

Memory 514 and database 510 may include cache memory, long term memory such as a hard drive, and/or external memory, for example, including random access memory (RAM), read only memory (ROM), dynamic RAM (DRAM), synchronous DRAM (SD-RAM), flash memory, volatile memory, non-volatile memory, cache memory, buffer, short term memory unit, long term memory unit, or other suitable memory units or storage units. Memory 506 and database 510 may store instructions (e.g., software 516) and data to execute embodiments of the aforementioned methods, steps and functionality (e.g., in long-term memory, such as a hard drive).

Computing device 508 may include a computing module having machine-executable instructions. The instructions may include, for example, a data processing mechanism (including, for example, embodiments of methods described herein) and a modeling mechanism. These instructions may be used to cause processor 512 using associated software 516 modules programmed with the instructions to perform the operations described herein. Alternatively, the operations may be performed by specific hardware that may contain hardwired logic for performing the operations, or by any combination of programmed computer components and custom hardware components.

Embodiments may include an article such as a computer or processor readable medium, or a computer or processor storage medium, such as, for example, a memory, a nontransitory computer-readable storage medium, such as a disk drive or a USB flash memory, encoding, including or storing instructions, e.g., computer-executable instructions, which when executed by a processor or controller, carry out methods disclosed herein.

In exemplary embodiments, a user (e.g., a clinician interacting with a server module or a patient interacting with a client module) has a user computer with Internet access that is operatively coupled to a server via a network, which can be an internet or intranet. User computer and server may implement various aspects of the embodiments that are apparent in the detailed description. For example, a user computer may be in the form of a personal computer, a tablet, a personal digital assistant (PDA), or a smart phone. The user computer may be configured with an application program that communicates with the server. This application program can include a conventional browser or browser-like programs.

Processor 512 may perform various methods described herein. For example, processor 512 may execute the method of FIG. 2.

Display 518 may display results and/or intermediate data such as the time until a patient will likely develop medication dependence, for example, as shown in the diagram of FIG. 6. Display 518 may include a monitor or screen, such as an organic light emitting diode (LED) screen, liquid crystal display (LCD) screen, thin film transistor display, or the like. In one embodiment, the user may interact with display 518 using input device(s) 520.

Input device(s) 520 may include a keyboard, pointing device (e.g., mouse, trackball, pen), a touch screen or cursor direction keys, communicating information and command selections to processor 512. Input device 520 may communicate user direction information and command selections to the processor 512. For example, a user may use the input device 520 to select.

Processor 512 may include, for example, one or more processors, controllers, central processing units ("CPUs"), or graphical processing units ("GPUs"), or field programmable gate arrays ("FPGAs"). Software 516 may be stored, for example, in memory 514.

As shown in FIG. 1B, module system 502 may include a plurality of modules or units capable of performing operations described herein. In an embodiment, system 500 may include a controlling module 701, a receiving module 702, a pharmacokinetic module 703, a pharmacodynamics module 704, a tolerance module 705, a dependence module 706, a dispenser control module 707, a de-escalation estimation module 708, a display module 709, and a corrected display module 710.

The modules described herein may be implemented as either software and/or hardware and may be stored in any type of computer-readable medium or other computer storage device. For example, each of the modules described herein may be implemented in circuitry that is programmable (e.g. microprocessor-based circuits) or dedicated circuits such as application specific integrated circuits (ASICS) or field programmable gate arrays (FPGAS). In one embodiment, a central processing unit (CPU) could execute software to perform the functions attributable to each of the modules described herein. The CPU may execute software instructions written in a programing language such as Java, C, or assembly. One or more software instructions in the modules may be embedded in firmware, such as an erasable programmable read-only memory (EPROM).

Controlling module 701 may determine which information or service is being requested of a server by a client. Receiving module 702 may receive from database 510 information associated with the service determined by the controlling module 701. For example, the information received by the receiving module 702, via a mobile input device or other sensor, may be information about a patient. Input information received by the receiving module 702 may include dose and time of medication administration, information about other medication dosages and substance use, cognitive-objective stress scores, anxiety or depression scores input using a numeric or visual analog scale, galvanic skin conductance or other real-time physiologic clinical indicators obtained from sensors.

The pharmacokinetic modeling module 703 may facilitate estimating effect-site concentrations of the medication according to information provided by the receiving module 702 and a pharmacokinetic model.

Information from the pharmacokinetic module 703 is provided to the pharmacodynamics module 704 which estimates the site-effect using the information provided by the receiving module 702 and a pharmacodynamics model.

The tolerance modeling module 705 estimates a tolerance level to a medication that develops over time. For example, the tolerance module 705 may estimate the decrease in the effect of a medication at the effect site that occurs with prolonged or repeated exposure of the body to the medication. The tolerance module 705 may include methods to estimate changes in the pharmacokinetic model for the medication, that is changes in the rate of metabolism that occur with increased exposure of the metabolic system to the medication, for example, as a result of metabolic enzyme induction. The tolerance module 705 may also include methods to estimate changes in the pharmacodynamics module 704 for the medication, that is, changes in the magnitude of the effect of the medication at the effect site that occur, for example, as a result of receptor upregulation or downregulation. The tolerance module 705 can employ a combined tolerance modelling method, for example incorporating a physiologic homeostatic disturbance model, or incorporate other modeling methods including continuous-time Markov chain based models, intensity based point processing modeling techniques such as Hawkes processes, or recurrent neural networks or other machine learning methods using individual and population data provided by the receiving module 702.

The dependence module 706 displays the time, for example the number of days, until the patient is predicted to become dependent on the medication assuming that the past dosage history is maintained in the future. In certain aspects, the patient can also enter a future dosage plan that differs from the past dosage history in order to determine the projected impact on the time until dependence. For example, a patient may voluntarily enter a reduced dosage plan in order to determine if this plan would delay or prevent medication dependence. Such a plan could also be entered by a clinician for a particular patient in order to guide medication therapy toward a dosage regimen which has a lower risk of medication dependence. In embodiments, the estimation of medication dependence can employ the tolerance models used by the tolerance module 705, where the occurrence dependence is determined to be in some proportion or in a threshold relationship to the level of tolerance.

The dispenser control module 707 controls the unlocking of a single-dose dispenser device that is configured to connect to the dispenser control module 707 via a hard-wired or wireless connection. In embodiments, the dispenser control module 707 may transmit a signal using Near Field Communication, Blue Tooth or other signal to the single-dose dispensing device which allows the device to unlock, making a single dose of the medication available to the patient.

The de-escalation estimation module 708 employs the tolerance estimation module 705 (combined tolerance estimation module) and the dependence estimation module 706, but incorporating future (de-escalation) dosing schedule that is different from the past dosing schedule and which may reduce medication tolerance and dependence compared to continuing the past dosing schedule.

The display module 709 displays a graphical depiction of the initial future dosing schedule recommended by the de-escalation estimation module 708, and the dependence estimation module 706, assuming that the recommended de-escalation schedule is adhered to. In embodiments, the graphical depiction may include the recommended daily dosing schedule plotted as a target curve showing a total dose per day for the entire duration of the de-escalation regimen, e.g., until a target daily dose that results in a conservative estimation that the patient will no longer be dependent on the medication, e.g. as determined by the de-escalation estimation module 708, using the planned dose schedule.

The corrected display module 710 displays a graphical depiction of a corrected future dosing schedule recommended by the de-escalation estimation module 708 and the dependence module 706, based on past dosing history and assuming that the corrected future de-escalation schedule will be adhered to. The corrected display module 710 presents a graphical representation of the newly estimated de-escalation curve for the patient which will show a longer period to approaching a target dose (which has a lower probability of dependence) if the patient fails to comply with the initial de-escalation regimen first displayed by the display module 709. Conversely, if the patient de-escalates the dosing regimen faster than the initial de-escalation dosing schedule initially displayed by the display module 709, then the target dose may be reached earlier than projected by the initial de-escalation regimen.

Figure 1D:
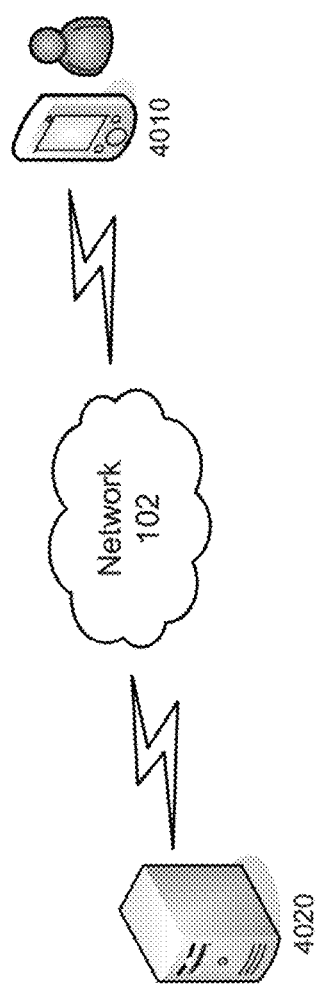
FIG. 1D illustrates a system for managing a risk of medication dependence, according to certain exemplary aspects.

FIG. 1D illustrates a system for managing a risk of medication dependence according to certain exemplary aspects. The system may include a server 4020, a client device 4010, and a network 102. The network 102 is any network that allows the server 4020 and the client device 4010 to communicate information with each other. Suitable networks can include or interface with any one or more of a local intranet, a PAN (Personal Area Network), a LAN (Local Area Network), a WAN (Wide Area Network), a MAN (Metropolitan Area Network), a VPN (Virtual Private Network), or a SAN (storage area network). Furthermore, communications may also include links to any of a variety of wireless networks, including WAP (Wireless Application Protocol), GPRS (General Packet Radio Service), GSM (Global system for Mobile Communication), CDMA (Code Division Multiple Access) or TDMA (Time Division Multiple Access), cellular phone networks, GPS (Global Positioning System), CDPD (Cellular digit packet data), Bluetooth radio, or an IEEE 802.11 based radio frequency.

FIG. 1C illustrates a method for recommending and controlling dose and timing of medication administration according to certain aspects. The term "medication," as used herein, may refer to any drug that can be administered to a patient. In an embodiment, the route is oral administration, for example ingestion of a pill or capsule. In embodiments, the drug may be an anxiolytic or anti-anxiety medication, for example alprazolam; an analgesic such as oxycodone, an antidepressant, or an antibiotic.

At step 602, the server 4020 or the receiving module 702 may receive information about a patient. The information may be transmitted by the client device 4010 or a sensor. Input information may include dose and time of medication administration, information about other medication dosages and substance use, cognitive-objective stress scores, anxiety or depression scores input using a numeric or visual analog scale, galvanic skin conductance or other real-time physiologic clinical indicators obtained from sensors as would be understood by one of ordinary skill in the art.

At step 604, the server 4020 may estimate effect-site concentrations of the medication based at least in part on the information received at step 604 using a pharmacokinetic model.

For example, embodiments can employ a single-compartment first-order pharmacokinetic model implementing the characteristics of:

$$C_c(t) = \frac{\text{Dose}}{V_c} e^{-t*Cl/V}$$

where:
$C_c$ is the concentration of the medication in the single compartment,
t is time,
Dose is the dose of the medication,
Cl is the clearance where Cl=$k_1$ $V_c$
$k_1$ is the time constant, and
$V_c$ is the volume of distribution of the compartment.

Embodiments may also employ two-compartment or higher compartment pharmacokinetic models. Embodiments may also employ kinetic models that are not first-order, for example using hyperbolic enzyme kinetic models such as Michaelis Menten kinetics.

In one aspect, information from the receiving module 702 is inputted into the pharmacokinetic module 703 which estimates effect-site concentrations of the medication. Information from the pharmacokinetic module 703 is provided to the pharmacodynamics module 704 which models the effect of the medication at the effect site.

At step 606, the processing circuitry may model a medication effect based on the effect-site concentrations and a pharmacodynamics model.

At step 608, processing circuitry models changes in the pharmacokinetics model which occur over time as a result of medication exposure. For example, at step 608, the processing circuitry can estimate changes in the elimination half-live of a medication that can occur because of enzyme induction caused by prolonged exposure to the medication or a related medication. At step 608, the current level of pharmacokinetic tolerance as well as to predict the level of tolerance in the future is estimated, assuming that the current dosage schedule is employed.

At step 610, circuitry can model changes in the pharmacodynamics model which occurs over time as a result of medication exposure. For example, circuitry can estimate changes in drug receptor levels that occur with prolonged exposure to the drug as a consequence of compensatory receptor upregulation (for receptor antagonist drugs) or downregulation (for receptor agonist drugs). At step 610, the current level of pharmacodynamics tolerance is estimated. In addition, the level of tolerance in the future is predicted assuming that the current dosage schedule is employed. Circuitry can employ models of pharmacodynamics tolerance based on receptor induction physiologic homeostasis (such as described in conjunction with FIG. 35A) or more general models based on continuous-time Markov chain based models, intensity based point processing modeling techniques (e.g., Nonlinear Hawkes Processes, such as described in Lingjiong Zhu PhD Thesis Department of Mathematics New York University May 2013), recurrent neural networks (e.g, *Doctor AI: Predicting Clinical Events via Recurrent Neural Networks*, Edward Choi, Mohammad Taha Bahadori, Andy Schuetz, Walter F. Stewart, Jimeng Sun barXiv:1511.05942v8 [cs.LG], 19 Mar. 2016) or other machine learning methods as would be understood by one of ordinary skill in the art such as, for example, (*Swarm Intelligence Based Technique for Rule Mining in the Medical Domain*, Veenu Mangat, International Journal of Computer Applications (0975-8887) Volume 4-No. 1 July 2010) using individual and population data provided by the receiving module 702. In embodiments, the pharmacodynamics tolerance prediction can be based on domain specific, knowledge-based and/or rule-based expert system methods and other clinical decision support modelling methods which may also incorporate neural network or other machine learning techniques as would be understood by one of ordinary skill in the art.

In certain aspects, the modeling of changes in both pharmacokinetic (e.g., at step 608) and pharmacodynamics (e.g., at step 610) parameters that occur with increasing exposure to a medication can be implemented into a single tolerance estimation module (e.g., tolerance module 705) which can include discrete models of pharmacokinetic tolerance, pharmacodynamics tolerance and/or combined physiologic homeostatic models of tolerance, as well as machine learning methods applied to individual patient and population data received at step 602 by the receiving module 702 and may employ domain specific, knowledge-based and/or rule-based expert system methods and other clinical decision support modelling methods which may also incorporate neural network or other machine learning techniques as would be understood by one of ordinary skill in the art.

A step 612, circuitry (e.g., dependence determination module 706) uses results from steps 608 and 610 to determine a conservative estimate of the time until a patient will become dependent on a medication. In certain aspects, the estimation of medication dependence can employ the tolerance models used at steps 608 and 610, where the occurrence dependence is determined to be in some proportion or in a threshold relationship to the level of tolerance. In some aspects, at step 612, a conservative estimate of the time until a patient is predicted to become dependent on the medication can be displayed.

In decision step 614, a determination is made of whether the patient is already dependent on the medication based on the conservative estimate determined at step 612. If the patient is not already estimated to be dependent on the medication, resulting in a "yes" at step 614, the process moves to step 616. Otherwise, if the patient is already estimated to be dependent on the medication, resulting in a "no" at step 614, the process moves to step 624.

At step 616, circuitry (e.g., the dependence module 706) displays the time until the patient is predicted to become dependent on the medication, assuming that the current dosage schedule is maintained. In embodiments, the conservative estimate of time until medication dependence determined at step 612 and displayed at step 616 may be based on alternative future dosing schedules. For example, a patient may voluntarily enter a reduced dosage plan in order to determine if this alternative plan would delay or prevent medication dependence. Such a plan could also be entered by a clinician for a particular patient in order to guide medication therapy toward a dosage regimen which has a lower risk of medication dependence.

In decision step 618, a determination is made of whether the time to medication dependence, as determined at step 612, is below a threshold value set by medication prescriber. If the time until medication dependence is below a prescriber-determined value, resulting in a "yes" at step 618, then the process moves on to step 620. In response to determining that the estimated time to medication dependence is not below a prescriber set threshold, resulting in a "no" at step 618, the process moves on to step 622. The prescriber set threshold may represent a predetermined threshold for example, 3 days.

At step 620, circuitry delays the unlocking of single-dose medication dispenser. A control signal may be sent to the dispenser-control module 707 which delays the unlocking of the single-dose dispenser device. At step 622, circuitry does not delay the unlocking of the single-dose medication dispenser.

If, in decision step 614, it is determined that the time to the development of medication tolerance for a patient is less than zero, then the circuitry (e.g., de-escalation estimation module 708) determines conservative de-escalation regimen at step 624. In one example, the de-escalation estimation module 708 employs pharmacodynamics estimation determined at step 610 (e.g., the tolerance module 705) and dependence estimation at step 612 but incorporating future (de-escalation) dosing schedule that is different from the past dosing schedule and which will reduce medication tolerance and dependence compared to continuing the past dosing schedule. The de-escalation estimation module 708 determines an initial de-escalation regimen that can be re-determined based on the actual dosing behavior of the patient received at step 602.

At step 626, circuitry (e.g., display module 709, processing circuitry of the client device 4010) displays a graphical depiction of the initial future dosing schedule determined at step 624, for example by the de-escalation estimation module 708 and the dependence estimation module 706, assuming that the recommended de-escalation schedule is adhered to. In certain aspects, the graphical depiction may include the recommended daily dosing schedule plotted as a target curve showing total dose per day for the entire duration of the de-escalation regimen, for example, until a target daily dose that results in a conservative estimation that the patient will no longer be dependent on the medication as determined at step 612, using the planned dose schedule.

At step 628, circuitry (e.g., corrected de-escalation display module 710) displays a graphical depiction of a corrected future dosing schedule determined at step 624 and step 612, for example by the de-escalation estimation module 708 and the dependence module 706, using all past dosing history and assuming that the corrected future de-escalation schedule will be adhered to. At step 628, a graphical representation of the newly estimated de-escalation curve for the patient is presented to the user. The graphical representation shows a longer period to approaching a target dose (which has a lower probability of dependence) if the patient fails to comply with the initial de-escalation regimen displayed at step 626. Conversely, if the patient de-escalates the dosing regimen faster than the initial de-escalation dosing schedule displayed at step 626, then the target dose may be reached earlier than projected by the initial de-escalation regimen. However, by following a de-escalation regimen which is faster than the recommended de-escalation regimen, the patient's daily dosing (as determined at step 602) may at time fall below the initial target curve initially displayed at step 626 indicating to the patient an increased risk of withdrawal symptoms during these periods when the actual daily dose falls below the recommended daily dose for the de-escalation regimen.

In certain aspects, the initial de-escalation curve (as displayed at step 626) may be displayed together with the corrected de-escalation curve (as displayed at step 628) and together with the patient's actual daily doses. The display of these two curves, together with the actual daily doses provides a clear graphical portrayal of the patients past adherence to the curve and the effect of the patient's compliance with the regimen on the future shape of the de-escalation curve and the effect of compliance on the targeted estimated time until the patient is no longer dependent on the medication. The clear portrayal provides powerful, continuous feedback to a patient and can be an unambiguous motivator toward the goal of achieving medication independence. Embodiments may include various gamification motivators such as motivating the patient to follow a safe "glide slope" toward a medication "soft landing" which achieves lower daily doses and a lower risk of medication tolerance and dependence.

In decision step 630, a determination is made of whether the patient is in substantial compliance with the initial or corrected de-escalation regimen. If it is determined that the patient is in substantial compliance, resulting in a "yes" at step 630, the process moves on to step 622.

At step 622, the processing circuitry does not delay unlocking the single-dose medication container when it is time for a next dose. The single-dose medication container is paired to the dispenser control module 707. If, on the other hand, it is determined that the patient is not in substantial compliance, resulting in a "no" at step 630, the control flow proceeds to step 620 in which the dispenser control module 707 may cause a delay in the unlocking of a single dose-medication dispenser that is paired to the dispenser control module 707.

Figure 2:
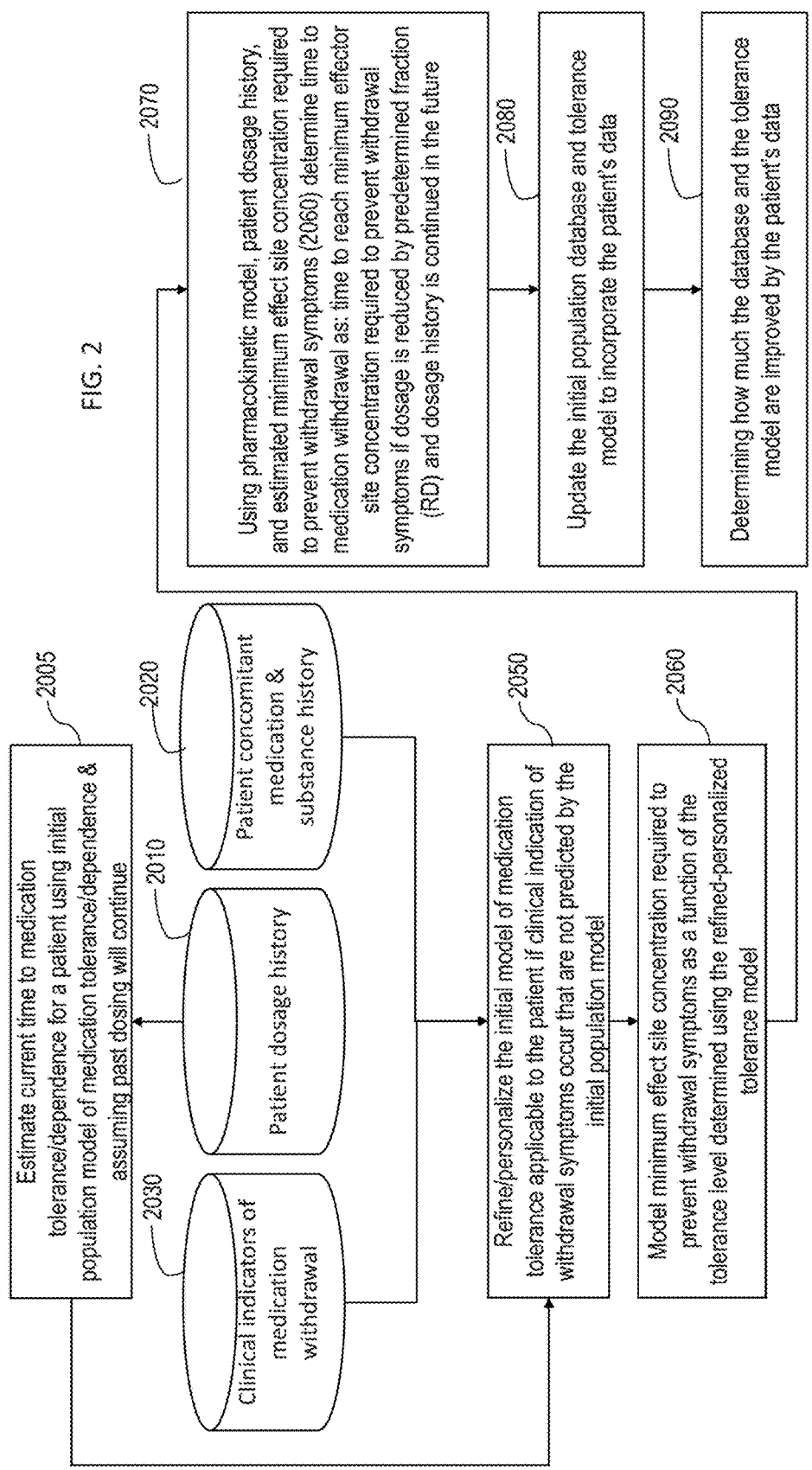
FIG. 2 is an exemplary flowchart illustrating a method of collecting and using clinical indicators of possible medication withdrawal in order to modify the model of medication tolerance-dependence being applied to a patient to estimate the time to development of medication tolerance/dependence.

FIG. 2 is an exemplary flow diagram showing a method of refining a population model of medication dependence using data from a single patient and of identifying information that can modify the population model according to one example. At step 2005, a baseline population model of medication tolerance and dependence is used to estimate the time until a patient will become dependent on a medication based on the patient dose history that may be stored in a patient dosage history data store 2010. The data store 2010 includes information about the doses of medication taken by a patient and the times that the doses were taken. In embodiments, the information may be entered by a patient using the client device 4010 to report the dose and time that the medication (e.g., a pill) is taken. In some embodiments, the reliability of this information is increased using a paired single-dose administration device (e.g., steps 620 and 622 of FIG. 1C, and the dispenser control module 707 of FIG. 1B) that verifies that all doses are accounted for. In a data store 2020, information representing the patient's concomitant medication use and substance use history is represented. In a data store 2030, information indicating clinical indicators of medication withdrawal is stored. For example, for an anxiolytic medication, the data store 2030 may contain information about periods when a high subjective stress score (e.g., input at step 602 and the receiving module 702 of FIG. 1B) during periods when a low cognitive objective stress score is reported (e.g. also input in step 602 of FIG. 1C, receiving module 702 of FIG. 1B). Additionally, in embodiments, data store 2030 may also include other clinical indicators of withdrawal not reported by the patient. For example, for anxiolytic medications the information in data store 2030 may include galvanic skin response information, heart rate variability information, or startle response data that can be acquired as an initial assessment or ongoing monitoring. In the data store 2020 information about a patient's concomitant medication and substance use is stored.

In step 2050, information from data stores 2020 and 2030 is used to personalize or otherwise refine the population model initially used to estimate the patient's time to medication dependence, for example at step 2005. For example, refinement or personalization of the population model may include using information from data store 2020 or 2030 to classify or stratify a patient into a specific risk class for medication dependence and a specific model of medication tolerance and dependence reflecting the patient's risk class is then applied in step 2050. For example, the population model used at step 2005 may incorporate specific values of time constants for receptor induction (e.g., time constants $\alpha$ and $\beta$ shown in FIG. 35B) when using the population model; and may use other values for these time constants when applied to a patient in a different risk class for tolerance and dependence, as determined by stratification criteria which employ patient-specific data stored in the data stores 2020 and 2030. The tolerance/dependence model employed at step 2050 may also use data from data store 2030 which includes information representing clinical indicators of potential medication withdrawal symptoms. For example, the information, stored in data store 2030 may include high anxiety level scores reported by a patient (e.g., using a visual analog scale for anxiety) during a time when the patient also reports a relatively low Cognitive Objective Stress (COS) score. In embodiments, the information, in data store 2030, may include high galvanic skin response readings from a sensor during periods when the COS score is low. The information representing a discrepancy between the anxiety score and the COS score may also be weighed based on its frequency of occurrence as well as the timing of occurrence. For example, in embodiments, a consistently recurring discrepancy between COS score and anxiety score at a time when the estimated effect site concentration (e.g., as determined at step 604 of FIG. 1C) is close to, but not below a threshold level that is conservatively expected to produce withdrawal symptom in the initial can be taken as evidence of withdrawal symptoms and the time constants of the initial population model of medication tolerance (e.g., using the receptor induction model of FIG. 35B) can be adjusted so that that the model applied to the patient conservatively predicts an increased probability of withdrawal symptoms under the same conditions.

In some embodiments, the medication may be an opioid analgesic and the data from data store 2030 can include clinical indicators of narcotic withdrawal. For example, a clinical indicator of opiate withdrawal may be sensor data from quantitative sensory testing device comprising a statistically significant indication of opioid-induced hyperalgesia as described in Differential Opioid Tolerance and Opioid-induced Hyperalgesia: A Clinical Reality, Hayhurst, C., Durieux, M. Anesthesiology 2 2016, Vol 124 483-488. In certain aspects, the statistical significance of a sensor reading can be determined by a number of existing methods of determining if a correlation between the sensor reading and a clinical finding (e.g., galvanic skin response and high anxiety score) would occur by chance. In embodiments, the p-value can be determined using Chi-square distribution calculation or other methods. In embodiments, the sensitivity and specificity of the sensor reading is employed in the determination of statistical significance. In embodiments, low-cost modern Quantitative Sensory Testing (QST) devices, such as NerveCheck, described in NerveCheck: An Inexpensive Quantitative Sensory Testing Device for Patients with Diabetic Neuropathy, Orburajus, G et. al, Diabetes Research and Clinical Practice 113, 101-107 can be employed as a sensor to identify clinical indicators of opioid-induced hyperalgesia associated with opioid tolerance and withdrawal.

The phenomena of opioid induced hyperalgesia (OIH) is a form or rapid medication tolerance for opioid narcotics that can occur in the very early stages of opioid therapy. The phenomenon has been recognized in the in-patient setting, and has been described in the immediate post-operative period and in other clinical settings, (e.g., Opioid-induced Hyperalgesia A Qualitative Systematic Review Martin S. Angst, M. D., J. David Clark, M. D., Ph.D. Anesthesiology 2006; 104:570-87 © 2006 American Society of Anesthesiologists, Inc. Lippincott Williams & Wilkins, Inc.). A hallmark of early-onset OIH is escalation of narcotic requirements in the early phase of opioid therapy. In some embodiments of the present method and system of determining, reporting, and enforcing personalized dosing guidelines to manage the risk of drug dependence, the method uses techniques to identify very early pattern of medication as a potential clinical indicator of rapid medication tolerance and dependence susceptibility. In such embodiments, for example, estimating the time until a patient will become dependent on a medication using the patient's dose history may comprise: a) recording the dose and time of each medication accessed by a patient from a locked, single-dose medication dispenser controlled by circuitry (e.g., circuitry of the server and/or circuitry of the client device); b) recording each request for a medication dose; c) estimating the patient's past effect site concentration of the medication at a plurality of times in the past using the patient's dose history and a pharmacokinetic model; d) estimating the patient's future effect site concentration of the medication at a plurality of times in the future using the pharmacokinetic model and setting the future dose history to be a function of the past dose history; e) estimating the patient's future level of medication tolerance using a model of medication tolerance for the medication and the patient's estimated effect site concentration at the plurality of times in the past, and in the future; f) modifying the model of medication tolerance applied to the patient in step e) of estimating the patient's future level of medication tolerance to increase the level of medication tolerance if either the dose and time of each medication accessed in step a), or the request for each medication in step b) indicate an administration or request pattern consistent with early dose escalation; g) setting the estimated medication withdrawal level to be the minimum effect site concentration necessary to prevent withdrawal symptoms to be a function of the patient's current level of medication tolerance; h) estimating, using the patient's estimated future effect site concentrations, the patient's estimated future level of medication tolerance, and the pharmacokinetic model, the time until medication withdrawal level will be reached if the patient's medication dosage is reduced, in the future, by a predetermined amount; and i) unlocking the single-dose medication dispenser controlled by the client device 4010 and/or the server 4020 only if the time until medication withdrawal level will be reached exceeds a predetermined value.

In certain aspects, an early, escalation of medication access or medication requests made by the patient using the access-control means can be used as a clinical indicator as early withdrawal (e.g., in step 2050 of FIG. 2) or early tolerance. In either case, the tolerance model being applied to the patient is modified to reflect a greater tendency toward medication tolerance and, using a dynamic model, a shorter estimated time until the patient will become dependent on the medication. In some embodiments, a pattern of early escalation of medication doses or medication dose requests is detected from the frequency of activation of the dispenser control module 707 for a paired secured controlled single-dose dispensing device (e.g., unit 4030 in FIG. 4), the detected pattern being detected either in the mobile application client device (e.g., client device 4010 of FIG. 4) or a server (e.g., the server 4020) communicating with the client device and the single-dose dispensing device. In either case a pattern of early dose escalation or early attempted dose escalation can, in some embodiments, be interpreted by the medication management system as clinical evidence of early mediation tolerance (for example, early Opioid Induced Hyperalgesia if the medication is an opioid analgesic) that has not been predicted by a model of medication tolerance that was initially applied to the patient. In such cases, the server 4020 can issue a warning, to the medication prescriber for example, of the possibility that the patient may be susceptible to early medication tolerance and dependence. In some embodiments, the warning of potential early tolerance and dependence is used to immediately identify a more conservative model of medication tolerance for the patient, which can potentially enforce a more conservative dosing regimen by communication with the paired secured controlled single-dose dispensing device 4030.

Figure 35A:
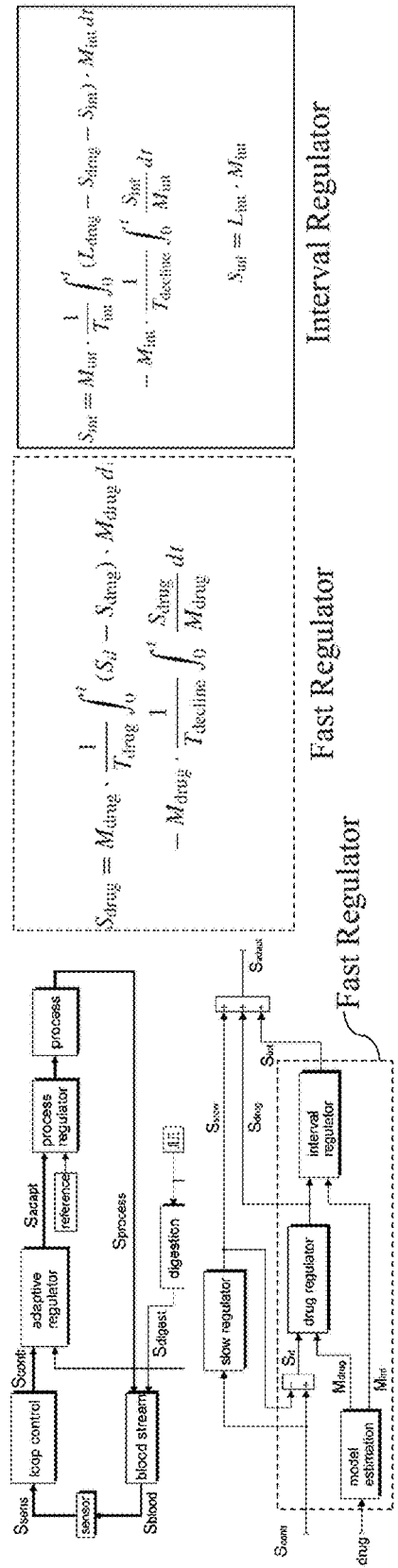
FIG. 35A is an exemplary diagram of a known method of modeling medication tolerance using a homeostatic physiologic model.

In step 2060, the refined/personalized model of medication tolerance determined in step 2050 is used to estimate a minimum effect site concentration required to prevent medication withdrawal as a function of the tolerance level determined using the refined/personalized tolerance model determined at step 2050. In embodiments, the minimum estimated effect site concentration required to prevent withdrawal symptoms may be selected to be as function of the current estimated level of medication tolerance in the personalized model of tolerance for the patient used in step 2050. For example, for an agonistic medication the state of tolerance may be selected to be in some proportion to the current estimated concentration of receptors (e.g., $W_t/W_{50}$ determined using the receptor induction model of FIG. 36B, and the time constants $\alpha$ and $\beta$ adjusted to achieve the refined receptor level). Embodiments may employ alternate tolerance/dependence models, for example, a homeostatic-physiologic model of tolerance, implemented as a dynamical system in digital or analog circuitry, as shown in FIG. 35A can be employed in which case the time constants of $T_{decline}$ and $T_{interval}$ are adjusted so as to achieve a level of $S_{adapt}$ which reflects a level of tolerance corresponding to early medication withdrawal.

In step 2070, the estimated time to medication withdrawal is determined using a pharmacokinetic model, patient dosage history data store 2010, and the estimated minimum effect site concentration required to prevent withdrawal symptoms (determined at step 2060). For example, the time may be estimated as the time to reach minimum effector site concentration required to prevent withdrawal symptoms if dosage is reduced by a predetermined fraction (RD) and dosage history is continued in the future. The dosage reduction factor RD, for example, may be expressed as a fraction of the current daily dose, or an absolute value in reduction. In step 2080, the database of patient information for the initial population model of mediation tolerance/dependence is updated to include the new information from the current patient. In embodiments, the initial population model of tolerance/dependence (e.g., step 2005).

In step 2090, it is determined by how much the population database (and by inference the population tolerance model) is improved by the patient's data. In embodiments, the method of Mandel described in U.S. Provisional Application No. 62/062,525 incorporated herein by reference in its entirety may be applied to determine the improvement to the population data made by an individual patient.

In some embodiments, the pharmacokinetic model employed is a population model. In certain aspects, the pharmacokinetic model may employ distribution half-lives or other time constants that are measured for the mediation for the specific patient, for example, from sample plasma concentrations or other measurements of the medication concentration obtained from the patient.

Figure 3:
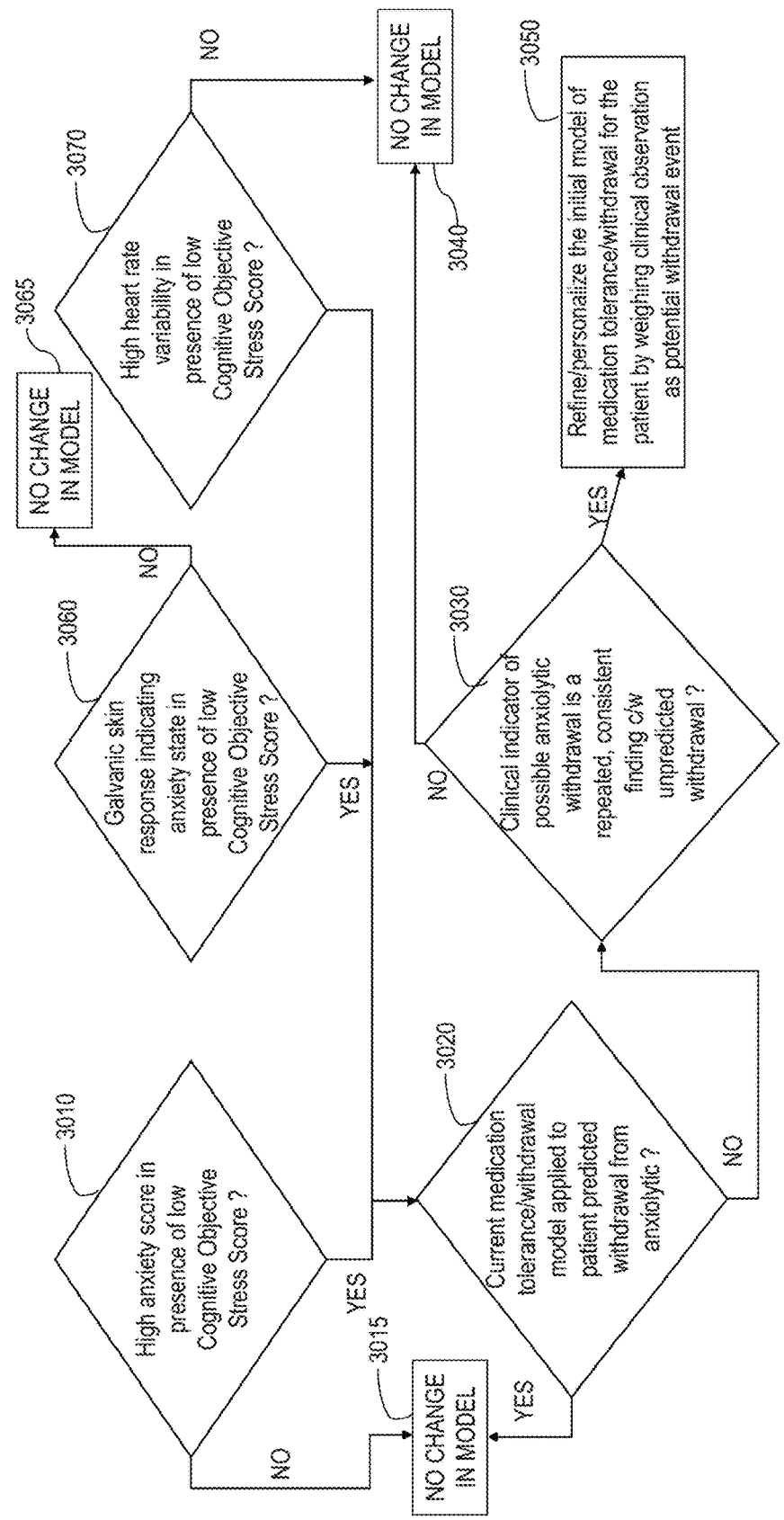
FIG. 3 is an exemplary schematic diagram illustrating a method of collecting patient information representing clinical indicators of possible medication withdrawal and using clinical indicators of possible medication withdrawal in order to modify the model of medication tolerance-dependence being applied to a patient to estimate the time to development of medication tolerance/dependence.

FIG. 3 is an exemplary flow diagram showing additional detail of a method of refining/personalizing a model of medication tolerance/dependence for anxiolytic medications according to one example.

In step 3010, a determination is made of whether there is no significant discrepancy between the COS score and the anxiety score. That is, an anxiety score that is high relative to an objective assessment of the stressfulness of the current situation is identified. The objective assessment of stressfulness may be determined by a Cognitive Objective Stress (COS) score that is reported by the patient at the same time that the patient reports an anxiety score (e.g., using an anxiety visual analog scale ranging from 1-5 with 1 being no anxiety and 5 being extreme anxiety or panic). For example, the self-report may be acquired in step 602 of FIG. 1C (e.g., via the receiving module 702). Other scoring methods using other scales may include intensity of physical signs associated with anxiety (e.g., trembling, dry mouth, choking sensation, dyspnea, tachypnea, or the like). A Cognitive Objective Stress (COS) score is a self-assessment tool which asks the patient to provide an objective score of the stressfulness of the situation independent of any anxious thoughts. The COS score is meant to filter the current situation through anxiety coping strategies and anxiety control responses that are commonly taught in conjunction with cognitive behavioral therapy. For example, the patient may be asked to reassess an anxious situation while deliberately avoiding the common thinking errors that typically accompany anxiety (e.g., jumping to conclusions, tunnel vision, all-or-nothing thinking, catastrophizing, or the like). The COS score attempts to isolate normal and objectively justifiable symptoms and signs of stress based on an objective analysis of the situation. For example, the COS score may incorporate techniques developed by Aaron T. Beck described in *Cognitive therapy and the emotional disorders*, Beck, A. T. (1975), Madison, Conn.: International Universities Press, Inc. ISBN 0-8236-0990-1, such as objective analysis of the likelihood and severity of a negative outcome in a certain situation as well as identifying and avoiding helplessness assumptions and underestimations of safety. The patient is instructed to assign a COS score to the stressfulness of the situation by examining beliefs about the stressfulness of the situation and systematically analyzing the reasonableness and correctness of the specific beliefs. The cognitive filtering and analyzing makes the COS score reflect a more objective assessment of the current situation than the anxiety score, which reflects the unfiltered emotional response or symptom.

Figure 35C:
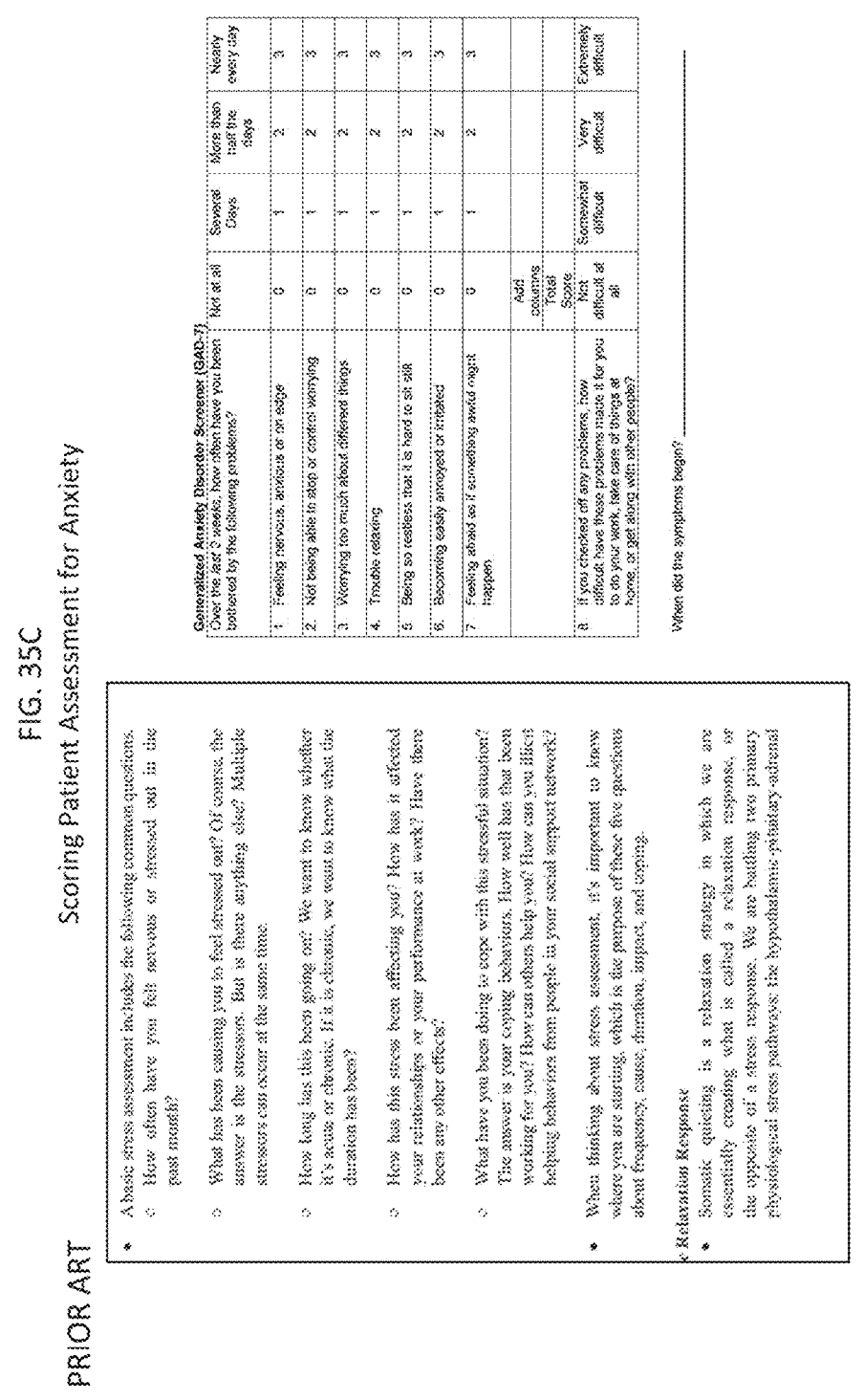

In exemplary embodiments, a patient is provided with instruction in the COS scoring technique using cognitive behavioral therapy methods which emphasize an objective analysis of the content and process of cognition and its potential governing role over non-rational thoughts and emotional responses such as anxiety, depression and the emotional subjective component of pain. FIGS. 35C and 35G shows exemplary known patient assessments for patient stress and anxiety.

If, in decision step 3010, it is determined that there is no significant discrepancy between the COS score and the anxiety score, then control flow proceeds to step 3015 where the tolerance/dependence is not refined/modified/or personalized for the patient. If it is determined, in decision step 3010, that there is a significant discrepancy between a COS score and an anxiety score then control flow proceeds to decision step 3020.

In decision step 3020, it is determined if the medication tolerance/withdrawal model currently being applied to the patient actually predicted a likelihood of anxiolytic withdrawal. If in decision step 3020 the withdrawal is predicted by the current model being applied to the patient, then control flow proceeds to step 3015, where no change is made to the model or the parameters of the model.

If on the other hand, in decision step 3020 it is determined that the model of medication tolerance/dependence currently being applied to the patient did not predict the likelihood of withdrawal symptoms (as indicated by a COS-anxiety score discrepancy), then control flow proceeds to step 3030.

If in decision step 3030, it is determined that there is no consistent, repeated observation of a clinical indicator of anxiolytic medication withdrawal then control flow proceeds to step 3040 where no modification is made to the tolerance-dependence model.

If, in decision step 3030, it is determined that there is a consistent, repeated observation of a clinical indicator of anxiolytic medication withdrawal then control flow proceeds to step 3050 where modification is made to the tolerance-dependence model. At step 3050, circuitry may modify the model of medication tolerance-dependence using a multivariate weights applied to one or more clinical indicators of potential medication withdrawal. For example, discrepancy between COS score and anxiety score may be given less weight for a patient that has not completed cognitive behavioral therapy instruction in using a COS scoring system, or for a patient who has been shown to report exaggerated scores or other incorrect use of the COS scoring method.

In one aspect, a galvanic skin response may be used as a clinical indicator of potential anxiolytic medication withdrawal. At step 3060, a determination is made of whether a galvanic skin response indicates an anxiety state. Galvanic skin response has been shown to be capable of differentiating stress levels in individuals with a success rate greater than 75% as described in *A Stress Sensor Based on Galvanic Skin Response (GSR) Controlled by ZigBee*, María Viqueira Villarejo, Begoña Garcia Zapirain and Amaia Méndez Zorrilla, Sensors 2012, 12, 6075-6101.

If, in decision step 3060 it is determined that there no galvanic skin response reading suggesting a relatively high anxiety state in the presence of a low COS score, then control flow proceeds to step 3065, where the model of medication tolerance/dependence currently being applied to the patient is not modified.

If in decision step 3060 it is determined that there is a galvanic skin response reading suggesting a relatively high anxiety state in the presence of a low COS score, then control flow proceeds to step 3020, which begins the analysis of the significance and consistency of this clinical indicator of potential anxiolytic medication withdrawal, as described above.

In one aspect, heart rate variability may be used as a clinical indicator of potential anxiolytic medication withdrawal. At step 3070, a determination is made of whether there is a high heart rate variability reading.

If, in decision step 3070 it is determined that there is no heart rate variability reading suggesting a relatively high anxiety state in the presence of a low COS score, then control flow proceeds to step 3040, where the model of medication tolerance/dependence currently being applied to the patient is not modified.

If, in decision step 3070 it is determined that there is a heart rate variability reading suggesting a relatively high anxiety state in the presence of a low COS score, then control flow proceeds to step 3020, which begins the analysis of the significance and consistency of this clinical indicator of potential anxiolytic medication withdrawal, as described above.

In embodiments, other clinical indicators of medication withdrawal can be used. For example, for analgesic medications a discrepancy between the expected level of analgesia predicted by an analgesic medication tolerance model and an objective or subjective clinical indicator of pain level could be weighed for repeatability and reliability, and potentially used to modify the analgesic tolerance-dependence model being used for a particular patient.

FIG. 35D is an exemplary flow diagram showing a clinical decision support method for prescription and recommendation dosing of anxiolytic medications using a personalized model of medication tolerance-dependence. Data store 3530 includes information including patient self-reports about the intensity of symptoms or signs. For example in the case of anxiety treatment with anxiolytic medications, elements of the anxiety assessment shown in FIG. 35C could be used, as well as other assessment vehicles published, for example, in the cognitive behavioral therapy literature. Patient self-reports may include purely subjective scoring of symptom severity and may also include potentially more objective assessments (e.g., the Cognitive Objective Stress Score in the case of anxiety). For analgesic medications, a subjective pain score and a filtered objective analysis of pain that is self reported. In the case of antidepressant medication, self-report of mood or other depression scales could be used.

Data store 3535 includes information including reports from reliable observers about the apparent intensity of symptoms or signs. For example in the case of anxiety treatment with anxiolytic medications, elements of clinician-scored assessments of the patient's anxiousness state could be used. In the case of depression, clinician-provided assessment vehicles could be employed. For analgesic medications, a subjective pain score and a filtered objective analysis of pain signs exhibited by the patient could be input by a clinician. Of course, the reliability and accuracy of this third party information may be verified, and in response to determining that the information can not be verifiable, then a lower weight or zero weight may be given.

Data store 3540 includes sensor-based clinical indicators of medication withdrawal. For example, the data store 3540 may include information about galvanic skin response, startle response, heart rate variability or other signs potentially associated with anxiolytic medication withdrawal. In the case of narcotic analgesic medication, or antidepressant medication withdrawal other physiologic sensor-based clinical indicators could be used.

Data store 3550 includes the patient's medication dosage history for the target medication (e.g., a narcotic analgesic medication in the case of pain management).

Data store 3560 includes the concomitant medication and substance dosage history for a patient. Self-reporting of concomitant medications and substance use, especially dosages, is notoriously unreliable and the weight of such reports may be increased using drug screening or other independent, objective evidence. When the concomitant medication dosage schedule is being enforced using the paired, locked, single-dose administration method (e.g., step 620 of FIG. 1C, and the dispenser control module 707 of FIG. 1B) then the weight of the information may be increased.

In step 3570, the processing circuitry may analyze each of the sources of information in the data stores 3530, 3535, 3540, 3550, 3560, to determine the statistical weighing that could be attributed to each of the elements of the clinical information stored in the data stores 3530, 3535, 3540, 3550, 3560.

In step 3575, the weighed information from data stores 3530, 3535, 3540, 3550, 3560 is used to determine a model of medication tolerance/dependence that is applied to estimate the patients susceptibility to medication dependence, for example to estimate the time until the patient would experience withdrawal symptoms if the current dosage was reduced by a predetermined amount.

Figure 36:
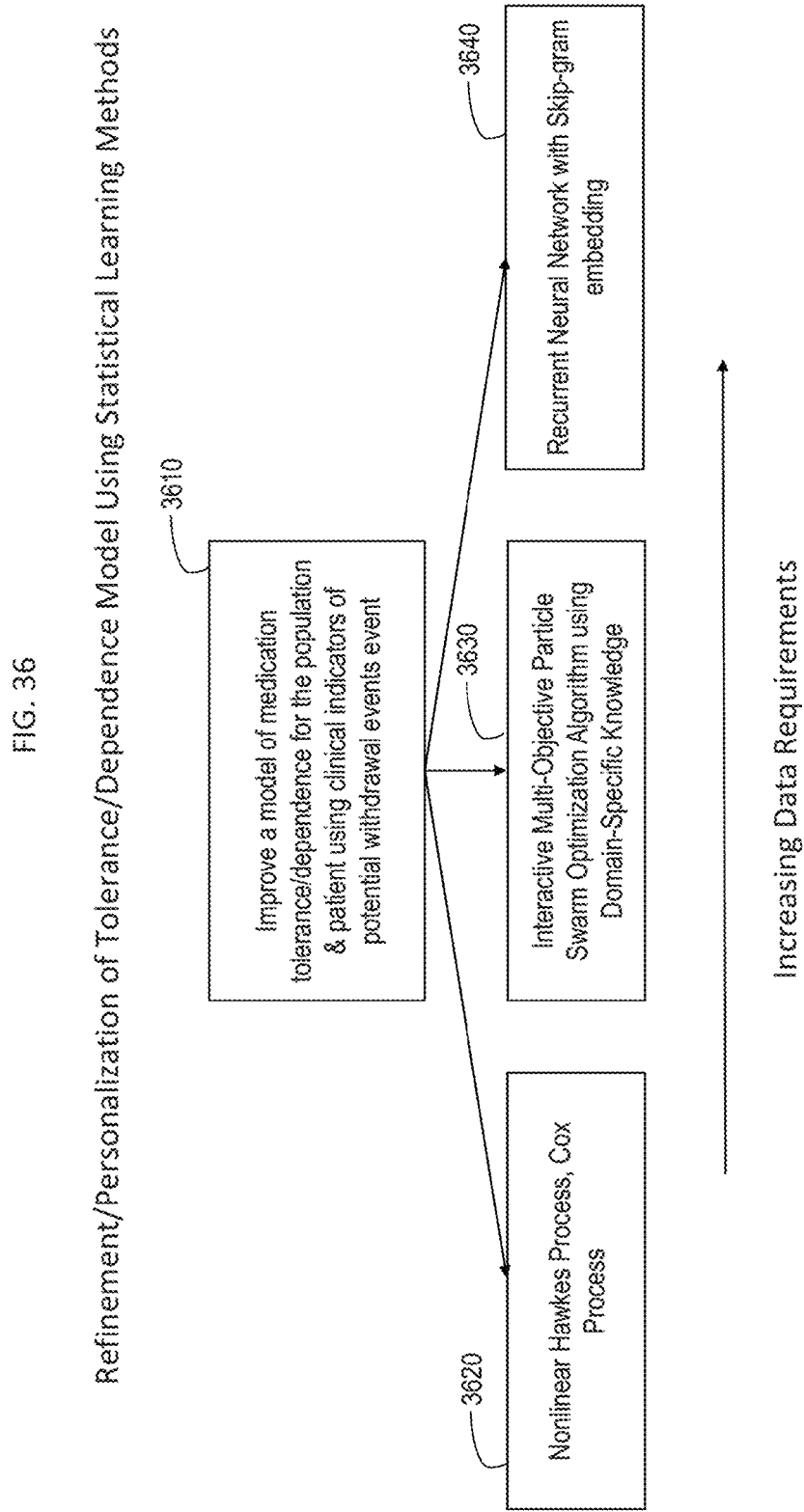
FIG. 36 is an exemplary flow diagram showing a method of improving population and patient-customized models of medication tolerance/dependence using statistical and machine learning methods.

FIG. 36 is an exemplary flow diagram showing a range of statistical learning methods that can be applied to the data of data stores 3530, 3535, 3540, 3550, 3560 to improve a population model of medication tolerance/withdrawal based on population data, and to adapt or otherwise refine or personalize a model of medication tolerance and dependence to a specific patient based on patient-specific data.

In step 3610, a method to improve the model of medication tolerance/dependence is identified. In one aspect, the method is identified based on the data available. For example, statistical learning methods have a lower data requirement than recurrent neural network techniques.

In step 3620, a statistical learning method such as non-linear Hawkes process or Cox process may be employed as would be understood by one of ordinary skill in the art. These methods can be used when the size of initial population database is relatively small. With an increasing amount of data, the step of 3630, can include methods which of interactive multi-objective particle swarm optimization using human input and employing domain-specific (e.g., expert prescriber) knowledge such as methods described in (1) Swarm Intelligence Based Technique for Rule Mining in the Medical Domain International Journal of Computer Applications, (0975-8887), Volume 4-No. 1, Jul. 2010 19, Veenu Mangat, and (2) Interactive multi-objective particle swarm optimization with heatmap-visualization-based user interface Engineering Optimization, Vol. 42, No. 2, February 2010, 119-139, Jan Hettenhausenay, Andrew Lewisaz, and Sanaz Mostaghimbx, each incorporated herein by reference in its entirety.

At step 3640, the population model of medication tolerance/dependence can be refined by applying recurrent neural networks with skip-gram embedding techniques. In addition, individual patients can be assigned to specific sub-models. The sub-models may be entirely different models with different rules, or the same models with different parameter values.

FIG. 4 is an exemplary diagram showing a method of estimating medication tolerance-dependence implemented as a distributed client-server system. For example, the client device 4010 can be implemented as a medication recommendation mobile application using a smartphone, tablet, portable fitness device such as Fitbit or Apple iWatch, or any mobile appliance as would be understood by one of ordinary skill in the art. For example, the server 4020 may provide the client device 4010 with the medication recommendation mobile application for installation on the client device 4010. For example, the client device 4010 can record information from a patient input or sensor input implemented as a receiving module (e.g., step 602 FIG. 1C, and the receiving module 702 FIG. 1B). In exemplary embodiments, the receiving module implemented as a medication recommendation mobile application on a mobile device may record the time and dose of the patient's medication. The patient may also enter the time and dose of simulated dosages of the medications. Simulated doses are entered into the system in order to determine the effect of a simulated dose or dosages on the estimated time until medication dependence (as discussed in conjunction with FIG. 6B). As shown in FIG. 4, the receiving module may also allow input of anxiety score, cognitive objective stress score, dosages of other medications or substances. Additionally, input to the input module may come from sensors which can provide information about physiologic, sensor-based clinical indicators of stress or anxiety (e.g., galvanic skin response, heart rate and heart rate variability, respiratory rate, startle response, and the like). In embodiments, the information input to the input module can be stored in the client device 4010. In some embodiments, the input information may be sent to the server 4020, via for example, a HIPAA-compliant protocol (the health insurance portability and accountability act) such as NCPDP (national council for prescription drug programs), ASC X12N (accredited standards committee), or CCR/CCD (continuity of care record/continuity of care document).

As shown in the exemplary diagram of FIG. 4, the server 4020 may receive the data from the client device 4010 and may determine an estimated time until medication dependence will develop. The server 4020 may transmit the estimated time to the client using a HIPAA-compliant interface (and, for example, using the methods described in conjunction with the methods discussed in conjunction with FIG. 1-3, FIG. 35A-B, FIG. 36B). Alternatively or additionally, the processing circuitry of the client device 4010 may determine the estimated time until medication dependence will develop.

If the patient is already estimated to potentially be dependent on the medication, the server 4020 may determine a conservative de-escalation regimen and a time period until the patient will conservatively no longer be dependent on the mediation if the regimen is followed. The server 4020 can transmit the time period and/or a graphical representation of the planned de-escalation regimen and an updated de-escalation curve (for example, as discussed in conjunction with FIGS. 10-14) to the client device 4010. Alternatively or additionally, the processing circuitry of the client device 4010 may determine the conservative de-escalation regimen and the time period until the patient will conservatively no longer be dependent on the medication if the regimen is followed in cooperation with the server 4020 or in duplication.

Further, as shown in the exemplary diagram of FIG. 4, the server 4020 may store information about population or cohort medication dosages, cognitive objective stress scores, anxiety scores, or other clinical indicators relative to the medication for which recommendations are being made (e.g., pain scores for analgesics, mood scores and other cognitive scoring instruments for antidepressants, and the like). In exemplary embodiments, the information can be transmitted from the server 4020 to the client device 4010 and provided to the patient for comparing to the population or to specific cohort groups as discussed in conjunction with FIG. 21 and FIG. 22.

As shown in the exemplary diagram of FIG. 4, embodiments are possible in which either the client device 4010 or the server 4020 or both communicate with a paired, secured, controlled single-dose dispensing device 4030. The controlled single-dose dispensing device 4030, for example may be controlled by steps 620 and/or 622 of FIG. 1C (e.g., via the dispenser control module 707 of FIG. 1B), as discussed in conjunction with FIG. 1C, and FIGS. 23-34.

In exemplary embodiments, the client device 4010 can be a stand-alone implementation or integrated, as client middleware (e.g., an application program interface 4034) to an existing mobile health or fitness application 4035, other consumer application, or as embedded hardware. Similarly, the sever 4020 may be implemented as a stand-alone health information system for medication management or may be integrated to an existing health information management (HIM) system or a consumer information server system (e.g., web server 4045) through an interface 4044. For embodiments in which both the client and the server implementations are integrated into existing mobile health and server HIM systems, the communication between the client device 4010 and the server 4020 can be via existing communications protocols between the existing mobile health application 4035 and the server HIM system 4045, which can employ NCPDP, ASC X12N, CCR/CCD, or other HIPAA-compliant protocols.

In some embodiments, the client device 4010, can display an estimated time until the patient can become dependent on the medication via the Medication Recommendation Mobile Application. Further, the medication recommendation mobile application can present the user with a button for controlling the operation of the paired secured controlled single-dose dispensing device 4030. In some embodiments, the button may not unlock the single-dose dispensing device 4030 until other criteria are satisfied (e.g., because the estimated time to medication dependence is below a prescriber-set threshold as shown in step 618 of FIG. 1C). The Medication Recommendation Mobile Application gives no display or other indication to the patient that the button will not result in the administration of the dose by the single-dose medication dispenser. In such embodiments, unsuccessful patient medication requests made by the patient are recorded by the system and the frequency or other trending of these requests can be analyzed as a potential clinical indicator of early medication tolerance associated with early dose escalation (e.g., opioid induced hyperalgesia in the case of opioid medications or other tachyphalaxis for other medications). Clinical indicators of early tolerance can then be used as information by the system to refine the medication tolerance model for the patient (e.g., in step 2050 of FIG. 2) to reflect a greater susceptibility to medication tolerance and dependence.

FIG. 5 is a diagram showing an exemplary client medication recommendation mobile application or fitness application according to one example. FIG. 5 shows an exemplary display of a scale for objective, cognitive scoring of the stressfulness of a current situation 5040; a scale for scoring the current level of anxiety 5050; display of buttons for entering medication dose and time (5010, 5020, 5030); and display of a conservative estimate of the time until medication dependence 5060. In FIG. 5, the conservative estimate of time until medication dependence is currently estimated to occur in more than 30 days. In exemplary embodiments, the "Medication" label on the medication button 5010 may be an anxiolytic such as alprazolam and displayed as "alprazolam". In embodiments, the conservatively estimated time until dependence, as displayed in FIG. 5, is determined, for example using the method described in conjunction with FIGS. 1-3, FIGS. 35A-35D, and FIG. 36.

The medication button 5010 is an example of an input to the receiving module 702 and to step 602, which for example makes entry of the dose. The medication button 5010 may show a usual dose (e.g., 0.25 mg) as default and the current time as the administration time for easy entry by the user. The exemplary buttons labeled Different Time 5020 and Different Dose 5030 allow entry of alternative doses and times that the medicine was actually taken.

In FIG. 5, the exemplary cognitive objective stress score input 5040 is represented as a visual analog scale ranging from 1-5. The exemplary anxiety score 5050 is represented using a visual analog scale from 1-5. The user may enter both scores at the time of medication administration or at other times.

FIG. 6A is an exemplary diagram showing display of a scale for objective, cognitive scoring of the stressfulness of a current situation; a scale for scoring the current level of anxiety; display of buttons for entering medication dose and time; and display of a conservative estimate of the time until medication dependence for a case in which dependence is currently estimated to occur in 15 days and the time until dependence is decreasing. The exemplary display of a conservative estimate of the time until medication dependence button 6060 shows a case in which dependence is currently estimated to occur in 15 days if the past dosage regimen is continued. In exemplary embodiments, the time until medication dependence is determined, for example, using the methods described in conjunction with FIGS. 1-3, FIGS. 35A-35D, and FIG. 36. In this example, the medication tolerance method indicates that the time until medication dependence is decreasing. The cognitive stress score and experienced anxiety score may be entered using scale 6040 and scale 6050 respectively.

Figure 6B:
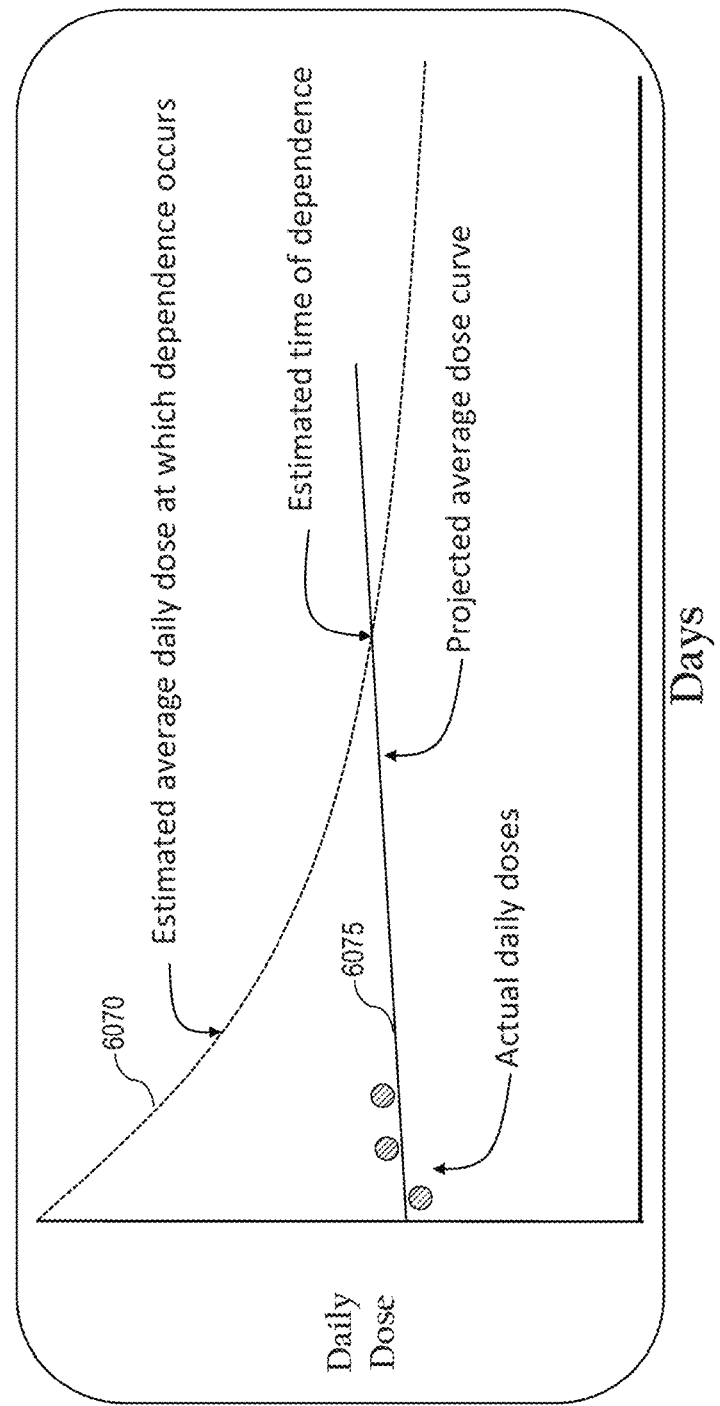
FIG. 6B is an exemplary diagram showing display of a first projected curve giving the daily medication dose that is estimated to result in medication dependence as a function of time, a second curve giving the actual and extrapolated daily medication dose, and the intersection of the two curves which is the estimated time and daily dose at which medication dependence occurs.

Alternate embodiments can portray the approach to medication dependence graphically, for example as shown in FIG. 6B. FIG. 6B is an exemplary diagram showing display of a first projected curve 6070 showing the average daily medication dose that is estimated to result in medication dependence as a function of time, a second curve 6075 giving the projected average daily dose curve projected into the future and assuming the patient's historical dosing average. Actual daily doses taken by the patient in the past are plotted as large hatched circles labeled "Actual daily doses" together with the projected average dose. The intersection of the first projected curve 6070 and the second curve 6075 is the estimated time and average daily dose at which medication dependence occurs. In this exemplary graphical depiction of the approach to medication dependence, the curve representing estimated average daily dose at which dependence will occur is conservatively estimated, for example, using the methods described in conjunction with FIGS. 1-3, FIGS. 35A-35D, and FIG. 36. Alternate embodiments can display other metrics of medication load such as an estimated average plasma concentration (e.g., using the pharmacokinetic model of step 604 of FIG. 1C, module 703 of FIG. 1B). Embodiments may incorporate various averaging windows and filters as appropriate to display the dynamics of specific medications.

Figure 6C:
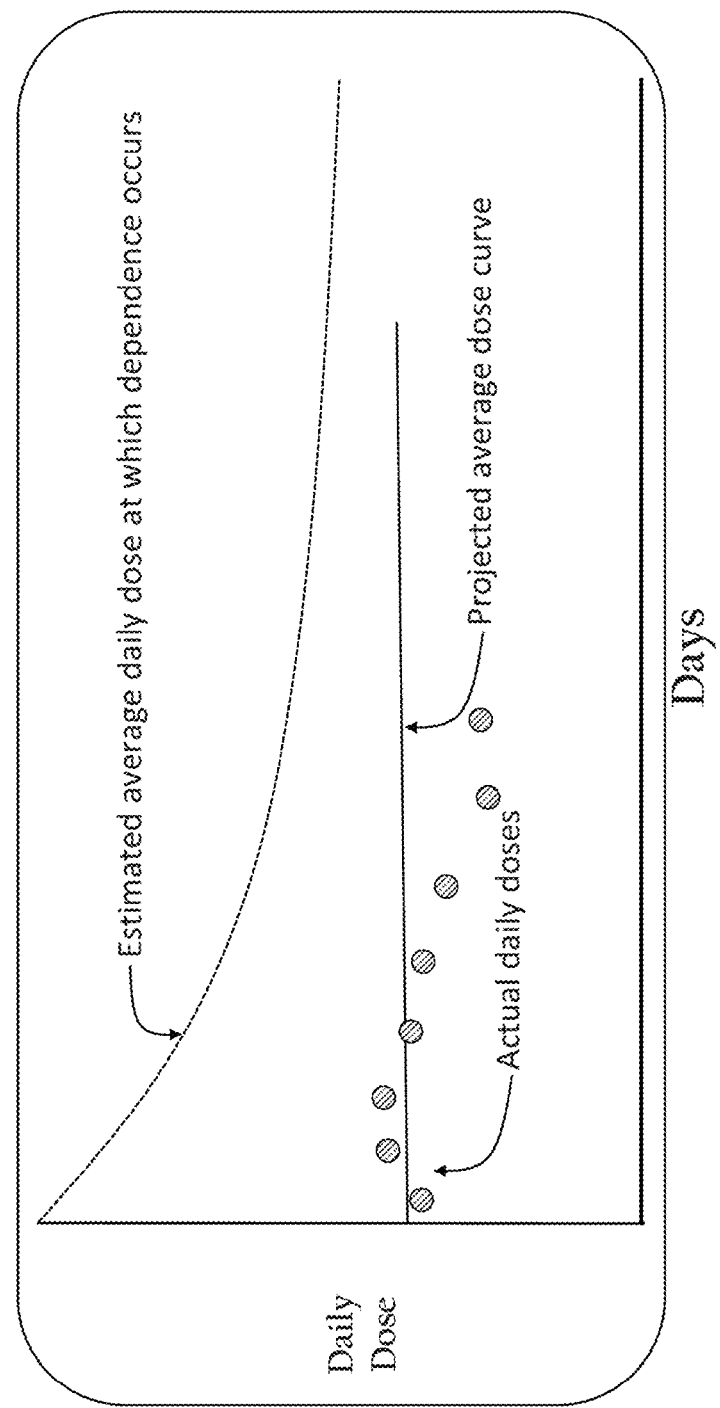
FIG. 6C is an exemplary diagram showing the same patient situation as depicted in FIG. 6B, but now that patient has decreased the daily dosage resulting in an upward shift in the first projected curve giving the daily medication dose that is estimated to result in medication dependence as a function of time, and a downward shift in the second curve giving the actual and extrapolated daily medication dose, which prevents the intersection of the curves and prevents medication dependence.

The graphical depiction of the approach to medication dependence can give a patient useful insight into the problematic accelerating approach to dependence state even if daily dosage is maintained constant. The mechanism of medication dependence includes compensatory receptor upregulation (e.g., for antagonistic medications), downregulation (e.g., for agonistic medications), or other physiologic or neurologic compensations (e.g., presynaptic effects and other neuroplasticity adaptations) which usually mean that the average daily dose at which medication dependence occurs will generally decrease with time. As tolerance and dependence curves generally follow such a first-order character (e.g., the receptor-induction model of medication tolerance and dependence shown in FIG. 35B and the homeostatic physiologic model of medication tolerance shown in FIG. 35A both follow an approximate first-order, two-compartment model). Consequently, if the patient decreases the average daily dose then the curve describing the daily dose at which dependence is estimated to occur is effectively shifted up to a higher daily dose range, while simultaneously the average daily dose curve itself tends to shift downward. These effects together mean that a moderate but consistent reduction in daily dosage can significantly delay the estimated time until medication dependence occurs. The effect is shown in FIG. 6C, which shows an exemplary diagram of the same patient as depicted in FIG. 6B, but in this case the patient has decreased the average daily dose, resulting in both less medication tolerance (an upward shift in the curve "Estimated average daily dose at which dependence occurs") and a downward shift in the "Projected average dose curve" which synergistically significantly delays the time until medication dependence occurs as represented by the intersection of the two curves (which, in the exemplary case of FIG. 6C do not intersect during the time period depicted in the graph. The graphical portrayal of the non-linear approach to medication dependence can educate patients as to the hazard of dose escalation. By using accurate dosage history together with the method described herein of employing a reasonable and conservative model of medication tolerance/dependence that is adapted to the individual patient, the graphical portrayal can be a useful daily warning of the approach to medication dependence. The graphical portrayal can motivate the patient to reduce daily doses to synergistically modulate both the upper medication tolerance curve and the lower daily dose curve in a way that delays or ultimately prevents the intersection of the two curves, and therefore prevents dependence.

Exemplary embodiments of the method can also estimate a time when medication dependence becomes unavoidable, given a past dosing history. Because tolerance and dependence mechanisms take time to recover (e.g., due to a specific half-life of an induced receptor), a patient may achieve a medication level at a certain time which does not result in medication dependence at that specific time, but which will result in a medication dependence state in the future even if the patient suddenly discontinues the medication at the specified time. In certain aspects, the method can report the time of "no return" as the time when medication dependence occurs, even though the patient may not yet be estimated to, for example, be susceptible to withdrawal symptoms at the certain time.

The graphical portrayal method, shown in FIG. 6B, also emphasizes to a patient that, once medication therapy is initiated or reinitiated, medication dependence becomes increasingly predetermined by the patient's past dose history and more difficult to correct as the patient approaches the estimated time of medication dependence. The determinism is a consequence of two central facts. First at any time the actual average daily dose is determined only by actual doses taken by the patient, and the projected average daily dose is weighed heavily by the actual past doses when projected only short periods into the future. The second constraint that makes it easier to prevent medication dependence than quickly correct an impending medication dependence state is that the biochemical (e.g. receptor induction), neurologic (e.g. neural plasticity), and other physiologic (e.g., compensatory homeostatic) mechanisms of tolerance and dependence are not instantaneous. They are governed by certain time constants of onset and offset which means that quickly reducing daily doses may not prevent dependence, since the top curve "Estimated average daily dose at which dependence occurs" may not shift upward quickly enough to avoid intersection with the curve labeled "Projected average dose curve".

The graphical portrayal makes it easy for the patient to visualize the potential effect of each dose of medication on both curves and on their intersection at the estimated time of medication dependence. The graphical portrayal emphasizes to the patient that once a dose history leading to medication dependence has been established, it becomes increasingly more difficult to prevent by late changes in the dosage pattern as time goes on. Conversely, the visualization of FIG. 6B can make apparent to the patient the effect of each dose of the medication on the estimated approach to dependence and can be used as a tool to encourage the patient to adopt early management and medication budgeting strategies which tend to prevent medication dependence.

Many medications are prescribed on a PRN ("as needed") basis. For example, the anxiolytic medications are often prescribed to be taken in response to or in anticipation of a situation which could precipitate anxiety. The cognitive objective stress (COS) score (e.g. included in step 602 of FIG. 1C, step 3010 of FIG. 3, data from client to server in FIG. 4, and in visual analog form as 5040 in FIG. 5) is a self-assessment tool that patients use to rationally analyze a feeling of anxiousness or a situation that a patient may fear will lead to anxiety. The COS assessment vehicle, in exemplary embodiments, can include an screening for exaggerated thinking, errors in thinking, catastrophizing, and other cognitive errors which tend to amplify an actual anxious experience or exaggerate a situation that the patient fears may lead to anxiety. In exemplary embodiments, the medication prescriber can ask the patient to perform a specific cognitive assessment and record a COS score before considering a dose of an anxiolytic medication. This cognitive assessment can often modulate the anxiety or feeling of impending anxiety, and can also be combined with relaxation response exercises. By encouraging or requiring the patient to make a cognitive assessment, and allowing the patient to visualize the contribution that each dose of anxiolytic medication could make toward medication dependence; the patient is encouraged to reduce unnecessary medication use. In exemplary embodiments, the method of requiring the patient to perform a COS or other assessment about the appropriateness of medication administration can be enforced using a secure, locked, single-dose administration device 4030 that is paired to and controlled by the client device 4010 and/or by the server 4020.

The exemplary diagram of FIG. 6C, for example, shows the same graphical portrayal for the same patient in FIG. 6B, but at a later time. In FIG. 6C, 5 days have passed since the portrayal in FIG. 6B. During this 5 days the patient has reduced the actual daily doses, leading to a downshift in the lower curve (Projected average dose curve) and an upshift in the upper curve (Estimated average daily dose at which dependence occurs). By reducing the daily doses, the patient tends to prevent medication dependence, as estimated by a conservative population model of medication tolerance/dependence for the specific medication, or a model that has been adapted to the patient using the methods of FIGS. 2-4, and FIGS. 35-36.

Figure 6D:
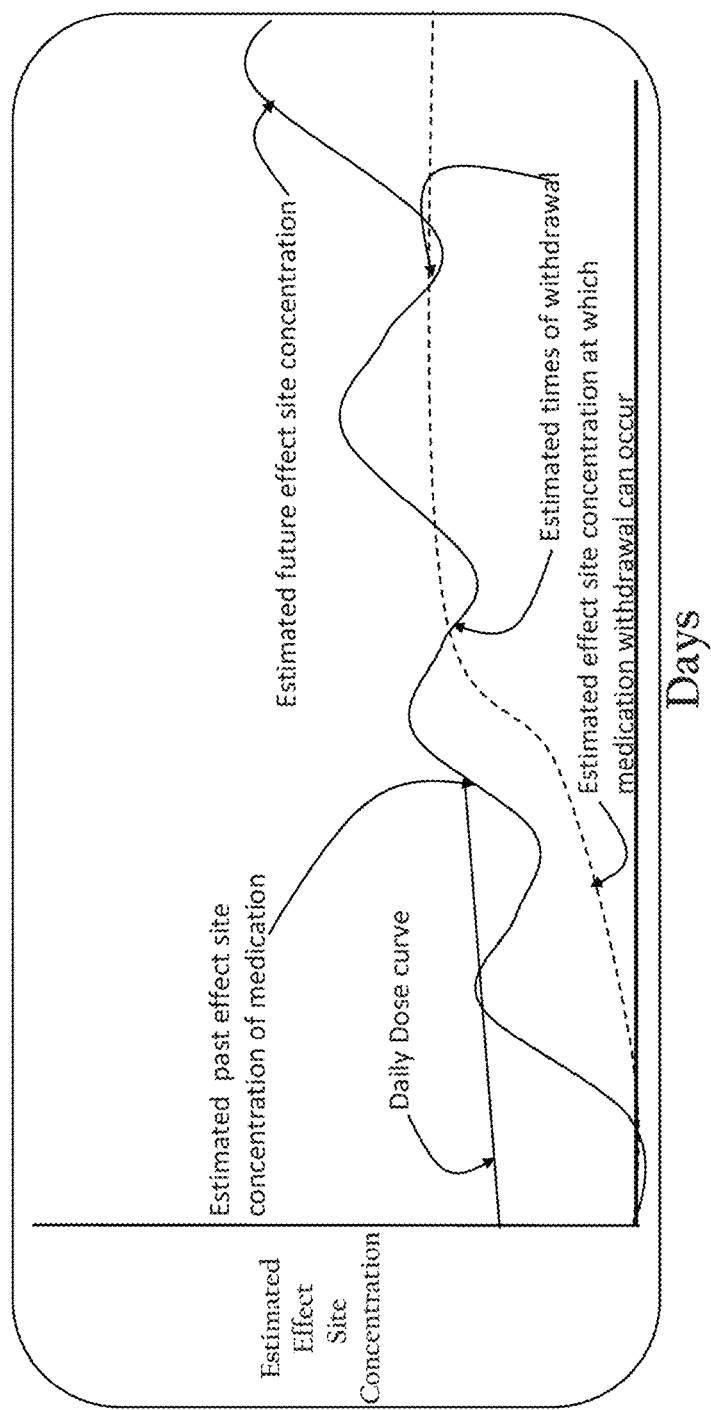
FIG. 6D is an exemplary diagram showing display of a first projected curve giving the effect site concentration that is estimated to result in medication withdrawal as a function of time, a second curve giving the estimated effect site concentration as a function of time, and the intersection of the two curves which is the estimated time at which medication withdrawal may occur.

FIG. 6D is an exemplary diagram showing a different graphical visualization of the approach to medication dependence and potential withdrawal. This graphical dashboard can be useful in helping a patient understand that the approach to medication dependence can be insidious, because stable or increasing steady-state effect site concentrations of medication can effectively mask withdrawal signs or symptoms. Presynaptic or postsynaptic receptor modulation, neural plasticity or other compensatory mechanisms which cause medication tolerance can build up slowly. Commonly, over the course of therapy for example, a patient's trough concentration of medication may consistently exceed the minimum effect site concentration below which withdrawal signs or symptoms will develop. For example, FIG. 6D shows a dashed curve labeled "Estimated effect site concentration at which medication withdrawal can occur. As a patient develops mediation tolerance, this value increases. At the same time, the estimated effect site concentration may be increasing toward an average or steady state value. During the normal course of therapy, peak effect site concentrations (maximum effect concentrations as determined over relatively short intervals) occur relatively soon after taking a dose of medication, whereas trough effect site concentrations (minimum effect site concentrations as determined over relatively short intervals) occur prior to the next dose of medication. Even when daily dosages are not increasing, a patient's estimated average, peak, and trough effect site concentrations may actually be increasing toward a stable steady state value. For example, the increasing effect site concentration values may result in trough levels being higher than the curve labeled "Estimated past effect site concentration of medication" represents the estimated effect site concentration for a patient, as determined by a pharmacokinetic model for example, based on known past dosage history. A different part of the same curve is labeled "Estimated future effect site concentration" for the same patient. On this part of the curve, the pharmacokinetic model is used to estimate effect site concentrations based on a dosage history that is a function of the past dosage history. For example, a stable daily dosage may be assumed, or extrapolation of an escalating dosage suggested by past actual daily dosage history may be used. As is apparent from the example of FIG. 6D, the increasing effect site concentrations can lead to a state for any patient in which the patient's "Estimated effect site concentration at which medication withdrawal can occur" can be close to normal trough concentrations, thereby preventing signs or symptoms medication withdrawal in the usual circumstance, despite substantial degrees of mediation tolerance. As shown in FIG. 6D, in certain cases even a brief delay of a single dose of medication can cause the effect site concentration to fall below the estimated effect site concentration at which withdrawal can occur. This graphical dashboard, displaying the information determined using the techniques of the present method, can provide an early warning to a patient of approaching or impending medication dependence, even in the absence of withdrawal signs or symptoms. This method of determining and presenting a conservative, but personalized assessment of the risk of tolerance and dependence has particular utility in assisting patients in preventing a state of tolerance that can result from dose escalation. The intersection of these two curves (estimated effect site concentration, and estimated effect site concentration at which withdrawal can develop) can be a useful daily warning to the patient to reduce dosages in a slow, controlled manner that tends optimally keep a falling the tolerance/withdrawal curve below a falling effect site concentration curve, for example using the de-escalation regimen and the "safe landing" methods of FIG. 10-14.

As previously described, the present method of estimating and reporting an estimated approach to medication dependence can employ a patient's dosing history and a projected dosing history that is based on an averaging or other extrapolation of the past dosing history. Other embodiments of the method allow a patient or a prescriber to enter simulated current or future doses in order to determine the potential impact on the time to medication dependence of one or more future medication doses. FIG. 6E is an exemplary diagram showing display of buttons for entering a simulated medication dose, which is a dose not actually taken by the patient but which is entered in order to determine the effect of the simulated dose or doses on the conservative estimate of the time until medication dependence. For example, a patient may contemplate taking a dose of an anxiolytic medication at the present time, but may wish to examine the effect of this dose on the estimated time to medication dependence. By pressing button 6067 shown in FIG. 6E, the patient could examine the effect of a simulated dose (usual dose at present time) on the estimated time until medication dependence. In other embodiments, the effect of one or more simulated doses is displayed graphically using the "crossing curves" graphical portrayal of FIG. 6B and FIG. 6C. Button 6061 may display the medication type and the dose. In exemplary embodiments, buttons 6063 and 6065 can be used to enter one or more alternative doses at one or more future times. For example, in the case illustrated in FIG. 6E, the patient enters a simulated dose and the method estimates that the time until medication dependence will be decreased by the simulated dose compared to not taking the simulated dose (e.g., compared to example of FIG. 6A for the same patient). In this method, patients can use simulated doses as a decision tool to determine whether an actual dose justifies the potential benefit of the medication dose (e.g., as cognitively assessed using, for example, a Cognitive Objective Stress score for anxiolytic medication, or an cognitive objective assessment of pain for analgesic medication) as weighed against the potential risk of the mediation dose as determined by the effect of the dose on the estimated time to medication dependence.

Figure 7:
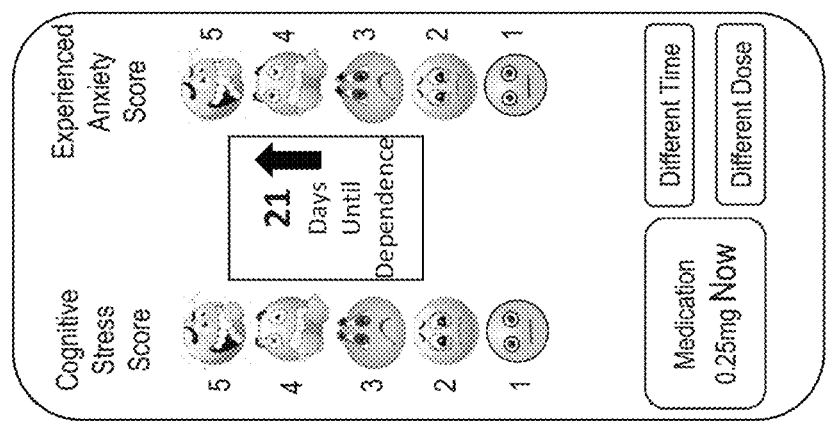
FIG. 7 is an exemplary diagram showing display of a scale for objective, cognitive scoring of the stressfulness of a current situation; a scale for scoring the current level of anxiety; display of buttons for entering medication dose and time; and display of a conservative estimate of the time until medication dependence for a case in which dependence is currently estimated to occur in 21 days and the time until dependence is increasing.

FIG. 7 is an exemplary diagram showing display of a scale for objective, cognitive scoring of the stressfulness of a current situation; a scale for scoring the current level of anxiety; display of buttons for entering medication dose and time; and display of a conservative estimate of the time until medication dependence for a case in which dependence is currently estimated to occur in 21 days and the time until dependence is increasing. In the example of FIG. 7, the same patient in the example of FIG. 6E and FIG. 6A has now reduced average daily medication dosage and the time until medication dependence is increasing compared to the earlier portrayed times, when the patient had a dosage history that was causing an accelerating approach to medication dependence. In exemplary embodiments, the use of the COS score assessment and associated objective pause before medication self-administration, combined with knowledge of the dependence-causing potential of each dose can help encourage responsible medication management practices which reduce the risk of medication tolerance and dependence.

Figure 8:
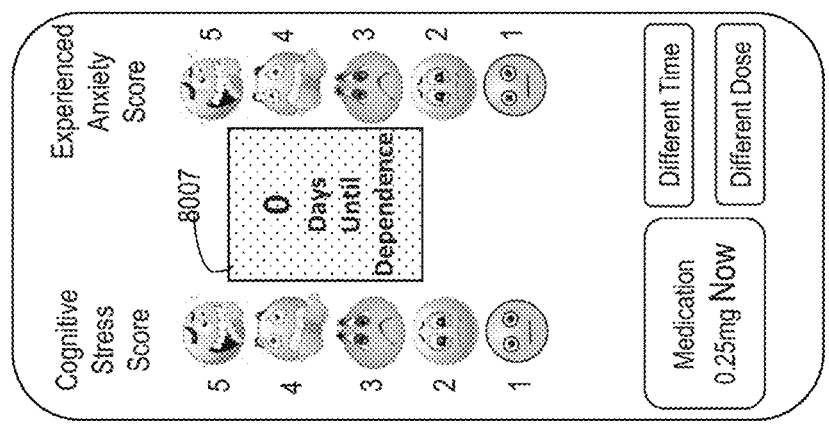
FIG. 8 is an exemplary diagram showing display of a scale for objective, cognitive scoring of the stressfulness of a current situation; a scale for scoring the current level of anxiety; display of buttons for entering medication dose and time; and display of a conservative estimate of the time until medication dependence for a case in which dependence is determined to have already occurred.

FIG. 8 shows the method employed in a medication management case which is a counterexample to the case shown in FIG. 7. In the example shown in FIG. 8, a patient has a medication dosage history that has led to an estimated condition of medication dependence. In exemplary embodiments, the method of conservatively estimating the time until medication dependence is determined, for example using the method described in conjunction with FIGS. 1-3, FIGS. 35A-35D, and FIG. 36. The display element indicates a zero time (e.g. in days) until medication dependence. In exemplary embodiments, dependence is estimated as a state of medication tolerance that will result in withdrawal symptoms or signs if the dosage is reduced by a predetermined amount.

Figure 9:
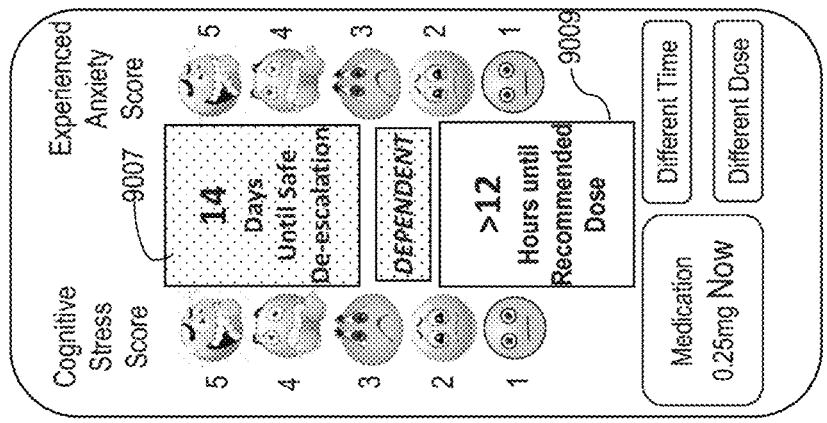
FIG. 9 is an exemplary diagram showing display of a scale for objective, cognitive scoring of the stressfulness of a current situation; a scale for scoring the current level of anxiety; display of buttons for entering medication dose and time; display of a conservative estimate of the time until medication dependence for a case in which dependence is determined to have already occurred; a display of a time until safe de-escalation following a de-escalation regimen; and a display of the minimum time until the next dose should be taken following the de-escalation recommendation.

FIG. 9 is an exemplary diagram showing display of a scale for objective, cognitive scoring of the stressfulness of a current situation; a scale for scoring the current level of anxiety; display of buttons for entering medication dose and time; display of a conservative estimate of the time until medication dependence for a case in which dependence is determined to have already occurred; a display of a time until a safe de-escalation can occur if the patient follows a prescribed de-escalation regimen; and a display of the minimum time until the next dose should be taken following the de-escalation recommendation.

Display element 9007 shows the display of a current time until safe de-escalation of a medication dosage can occur following a prescribed de-escalation dosage regimen. In exemplary embodiments, a conservative population model or personalized model (e.g., FIG. 2, FIG. 3, FIG. 35, FIG. 36) of medication tolerance/dependence is employed to produce a de-escalation regimen for a patient that weighs both the desired time to de-escalation and the risk or likelihood of medication withdrawal signs or symptoms. In the example of FIG. 9, a 14 day de-escalation regimen has been established and display element shows 14 days remaining in the regimen. Display element 9009 shows a minimum time until the next recommended dose as prescribed by the de-escalation regimen. In this example, the de-escalation model recommends that the patient attempt to wait at least 12 hours until taking the next dose of medication if possible. In exemplary embodiments, subsequent doses are conservatively estimated and recommended based on previous doses and the effect of those doses on adherence to the de-escalation regimen. For example, if the patient is incompliant with the de-escalation regimen and takes a dose of medication earlier than the time suggested by the de-escalation regimen, then the tolerance dependence model will likely increase the time required to achieve safe de-escalation (e.g., increasing the value displayed in 9007).

Figure 10:
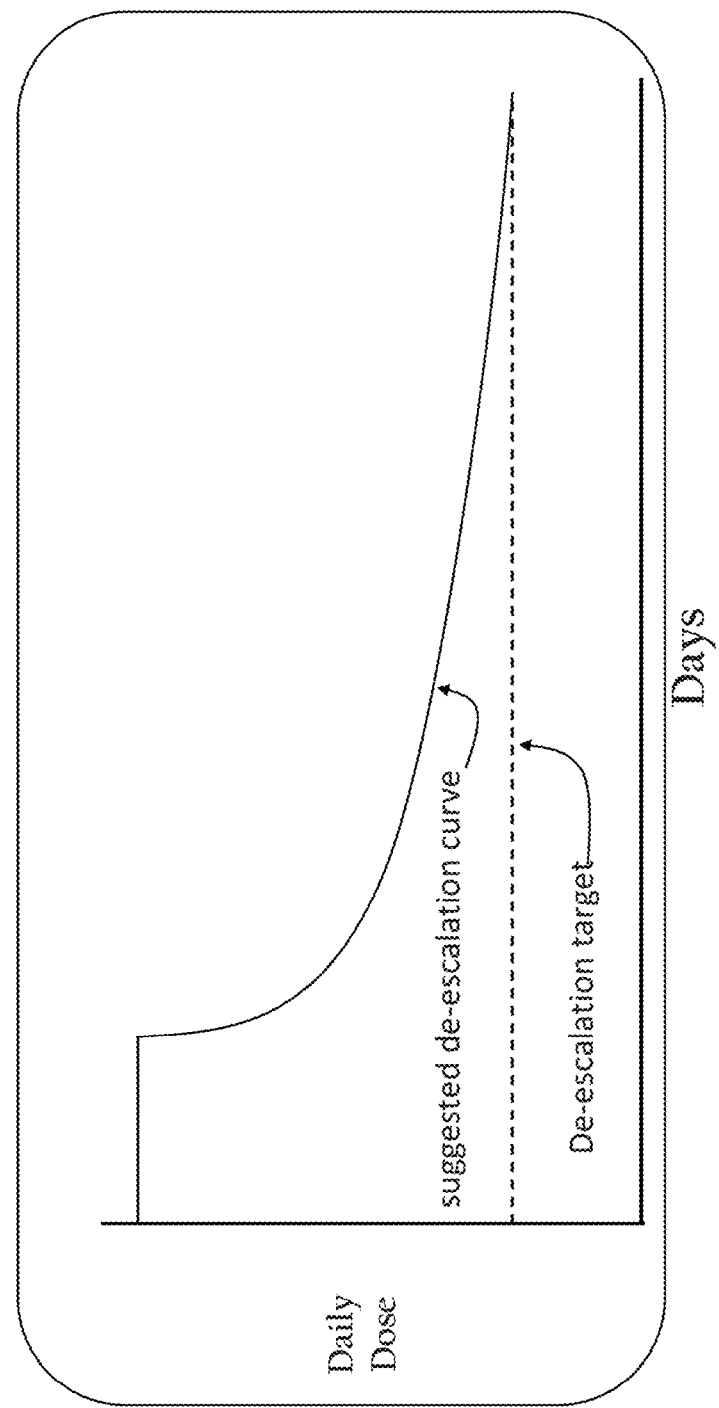
FIG. 10 is an exemplary graph showing display of a suggested conservative de-escalation dosing regimen determined to return a patient to a state of medication independence.

FIG. 10 shows a graphical display of the de-escalation regimen plotted as target daily dose as a function of time. If the patient follows the suggested de-escalation regimen, then the actual daily doses (e.g., plotted as hatched or solid circles in FIGS. 11-14.) will closely match the plotted de-escalation curve. The suggested de-escalation can be portrayed and used by the patient as a conservative estimate of a safe "glide path" to be used to approach a specific daily dosage at which the risk of medication tolerance/dependence is reduced. In FIGS. 10-14, the target daily dosage is labeled as the de-escalation target and, in other embodiments, may also reflect estimated medication levels in plasma or at the effect site.

Figure 11:
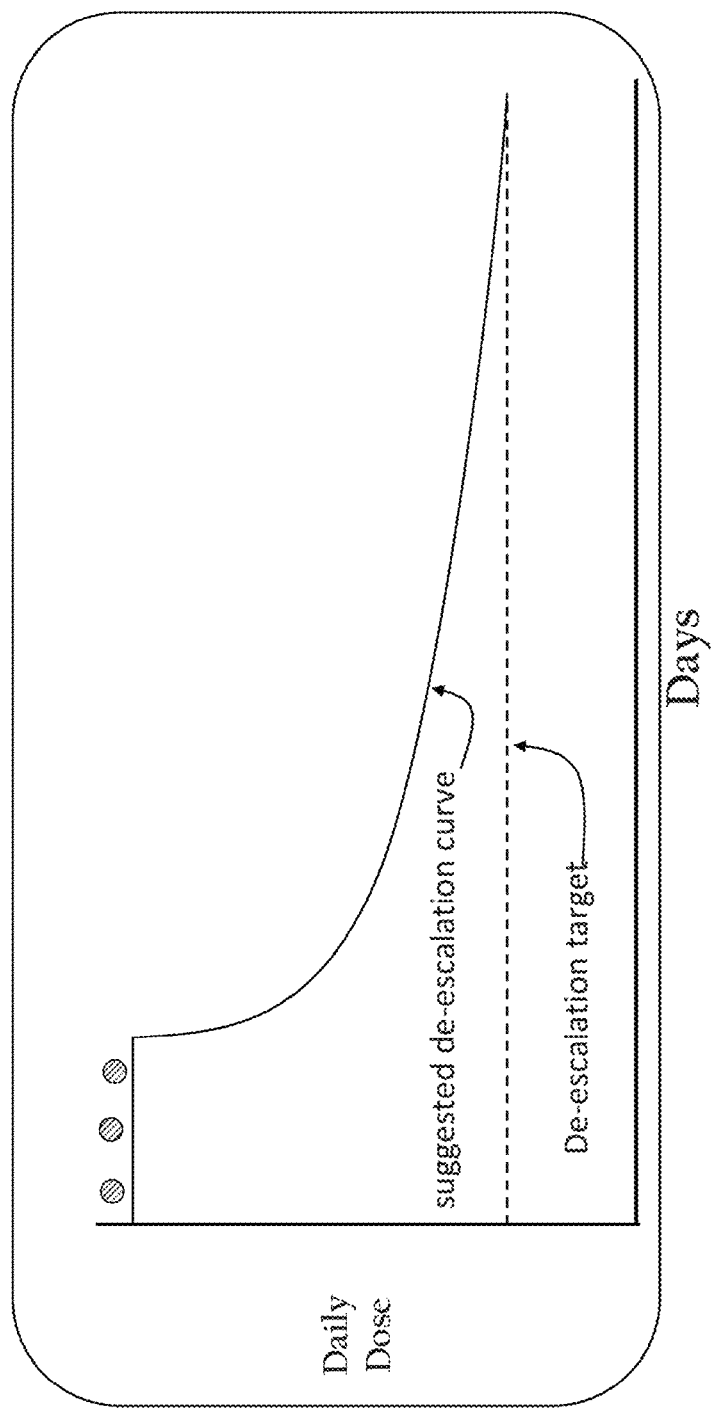
FIG. 11 is an exemplary graph showing display of a suggested conservative de-escalation dosing regimen determined to return a patient to a state of medication independence, and daily dose from the preceding three days.

FIG. 11 shows the same suggested de-escalation curve an de-escalation target curve as FIG. 10, but now including three actual daily dosages that were taken by the patient in the 3 days before the de-escalation regimen was started.

Figure 12:
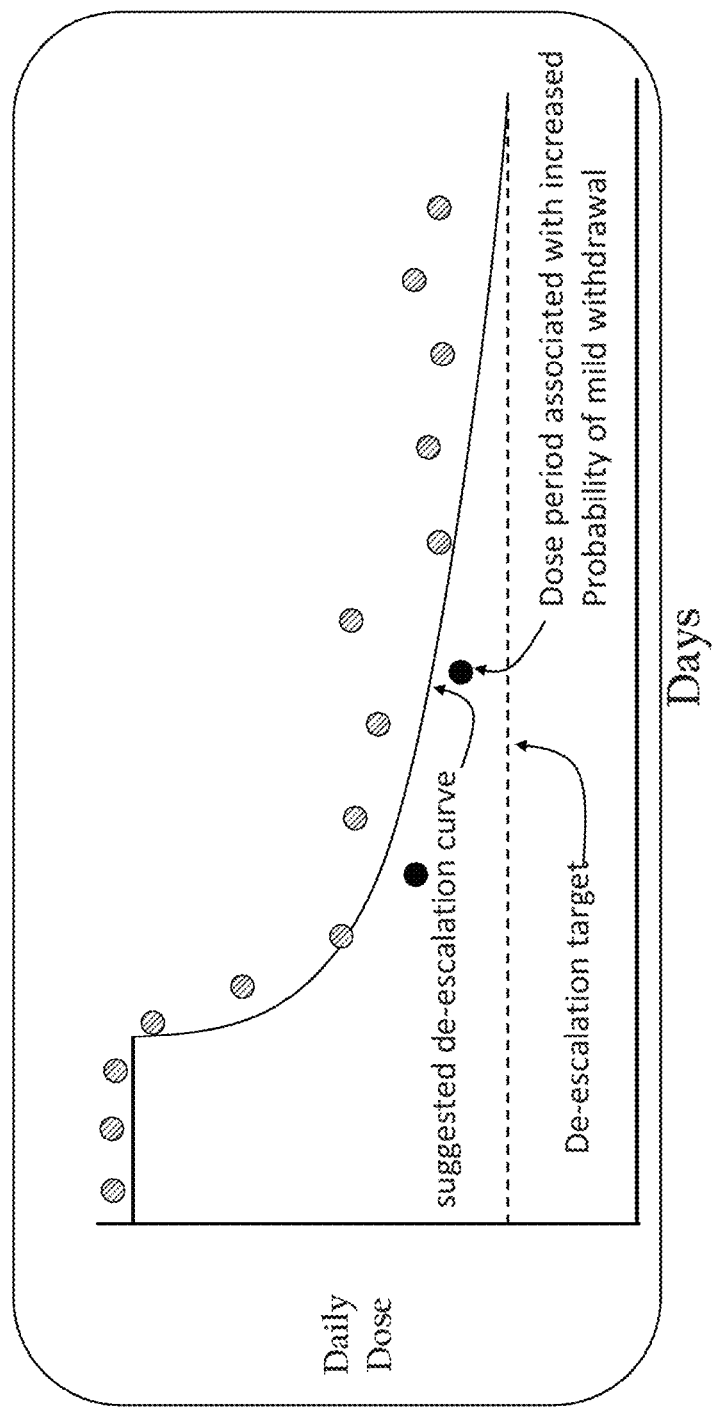
FIG. 12 is an exemplary graph showing display of a suggested conservative de-escalation dosing regimen determined to return a patient to a state of medication independence, and daily dose from the preceding 16 days, showing general compliance with the recommended regimen.

FIG. 12 shows an example of the same patient illustrated in FIG. 11, but in FIG. 12, the patient is now 13 days into a largely successful de-escalation regimen. FIG. 12 shows that the patient's daily doses closely followed the suggested de-escalation curve. However, on the fourth day of the actual de-escalation regimen, the patient' daily dose fell slightly below the daily dosage estimated by the model to potentially result in signs or symptoms of medication withdrawal at that time. In exemplary embodiments, the de-escalation regimen is provided as a guideline. If the patient keeps daily dosages consistently above the de-escalation guideline then the approach to successful de-escalation is delayed. If, on the other hand, the patient allows daily dosages to fall significantly below the de-escalation curve, then signs or symptoms of medication withdrawal may be expected during those periods. The solid dark circles illustrated in FIG. 12 fall below the suggested de-escalation curve and indicate to a patient that an increased risk of withdrawal signs of symptoms may occur during the associated dosing periods. Using exemplary models of medication tolerance/withdrawal, the expected severity of the withdrawal signs or symptoms can be in some proportion to the vertical displacement of the actual dose from the suggested de-escalation curve. The graphical portrayal of a personalized suggested or prescribed de-escalation regimen shown in FIG. 11 and FIG. 12 can provide a patient with a conservative guideline to follow, and ongoing feedback revealing the patient's compliance with the regimen.

Figure 13:
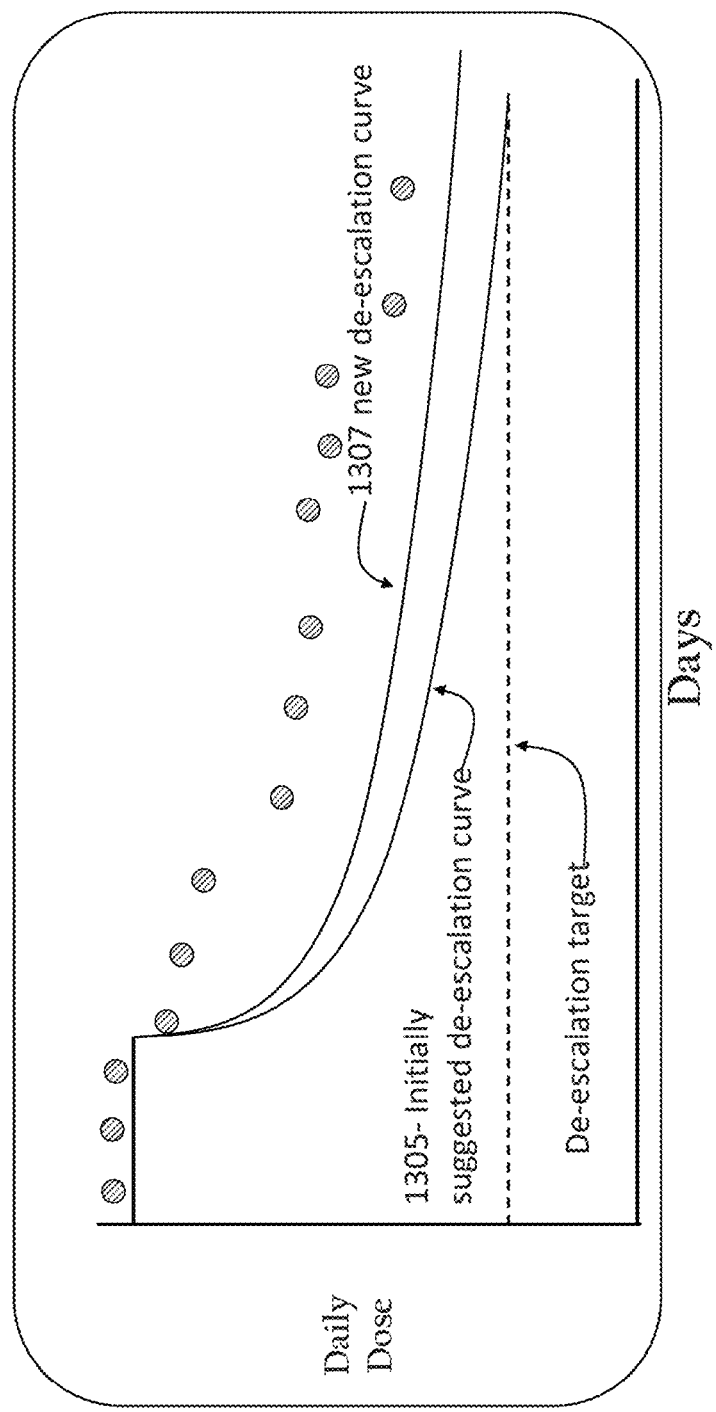
FIG. 13 is an exemplary graph showing display of a suggested conservative de-escalation dosing regimen determined to return a patient to a state of medication independence, and daily dose from the preceding 16 days, showing general incompliance with the recommended regimen and a new recommended de-escalation regimen.

FIG. 13 shows the initial suggested de-escalation regimen for the same patient, but in this case the patient fails to follow the suggested de-escalation regimen. The first three hatched circles portray the same pre-de-escalation regimen daily dosages for the same patient as portrayed in FIG. 11 and FIG. 12. However, in this case the patient did not follow the suggested dosing guideline but instead showed substantial incompliance with the initially suggested de-escalation curve, labeled 1305. In this case, the patient only made modest reductions in daily medication dosages during the de-escalation regimen. In response, the system 500 re-calculated a new de-escalation curve 1307 for the patient to follow. The new de-escalation curve 1307 produces a longer time period to de-escalation than the initially suggested de-escalation curve 1305. In the case of the recalculated de-escalation curve, the corresponding de-escalation target is several days farther into the future and is not shown since it is beyond the time axis on the graphical display of FIG. 13. In embodiments, the de-escalation target time can be portrayed numerically, as for example, using the graphical element 9007 of FIG. 9.

Figure 14:
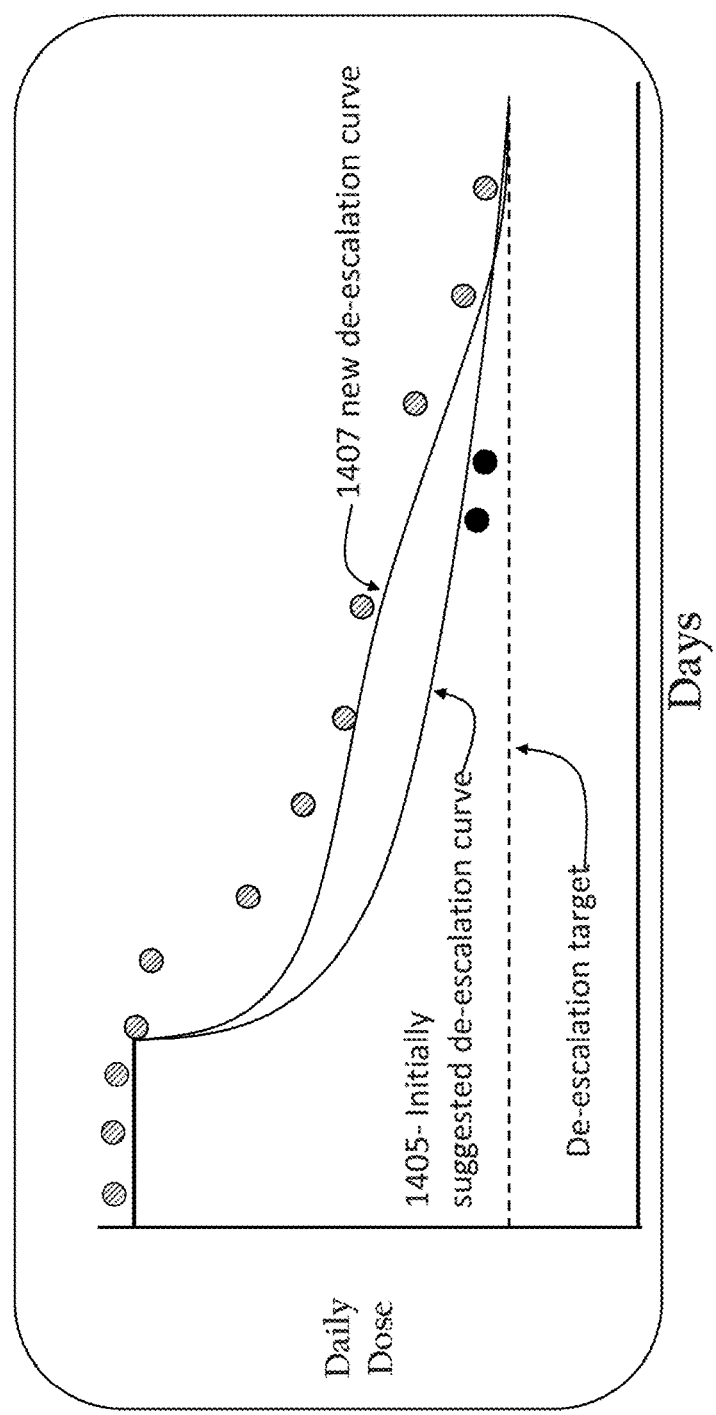
FIG. 14 is an exemplary graph showing display of a suggested conservative de-escalation dosing regimen determined to return a patient to a state of medication independence, and daily dose from the preceding 16 days, showing initial incompliance with the recommended regimen and a subsequent overcorrection leading to potential withdrawal symptoms but reaching the initially targeted de-escalation goal.

FIG. 14 shows a different example involving the same patient and the initially suggested de-escalation curve 1405. In this example, the patient initially had poor compliance with suggested de-escalation regimen as evidenced by the fact that the initial actual daily dosages were significantly above the initially suggested de-escalation curve. In this case, the mediation tolerance/dependence model is used to dynamically recalculate a new de-escalation curve 1407 that reflects the patient's initial incompliance. On the $7^{th}$ and $8^{th}$ day of the de-escalation regimen, the daily dosage plot indicates that the patient administered daily dosages that were substantially below the daily dosages corresponding to the dynamically recomputed recommended de-escalation curve corresponding to day 7 and day 8. The corresponding solid circles indicate some risk of medication withdrawal signs or symptoms during day 7 and day 8. However, the below-recommended dosages during these two days results in a dynamically recomputed de-escalation curve that has been "pulled down" by the two days of underdosing, resulting in a curve that the patient follows over the next three days to a successful de-escalation at the initial de-escalation target time. Using a dynamically recalculated tolerance-dependence model, a patient is effectively "given credit" for daily dosages that are on or below the recommended de-escalation curve, as dosages below the curve can effectively accelerate the de-escalation, albeit while incurring some risk of withdrawal signs or symptoms during the underdosing periods. Since small underdoses are expected to be associated with relatively mild withdrawal signs or symptoms, this can actually be a useful strategy for giving the patient flexibility and choice in de-escalation from some types of mediations. For example, de-escalation from an anxiolytic medication can be easier during a weekend period, when mild withdrawal symptoms have little or no impact on performance and are not exacerbated by a stressful environment. Moreover, some patients may actually have better success with a more aggressive de-escalation regimen which takes less time but may incur more signs or symptoms of withdrawal. By dynamically recalculating the de-escalation curve, the patient is given ongoing feedback about compliance and can make decisions toward more successful de-escalation outcomes. In embodiments, the medication prescriber can also enter parameters that influence and shape the suggested de-escalation regimen, for example either encouraging strict compliance to the initial de-escalation curve or encouraging patient-selected, but prescriber-limited periods of more aggressive de-escalation toward meeting an initial de-escalation target or a more aggressive target that is developed during the de-escalation regimen.

Figure 15:
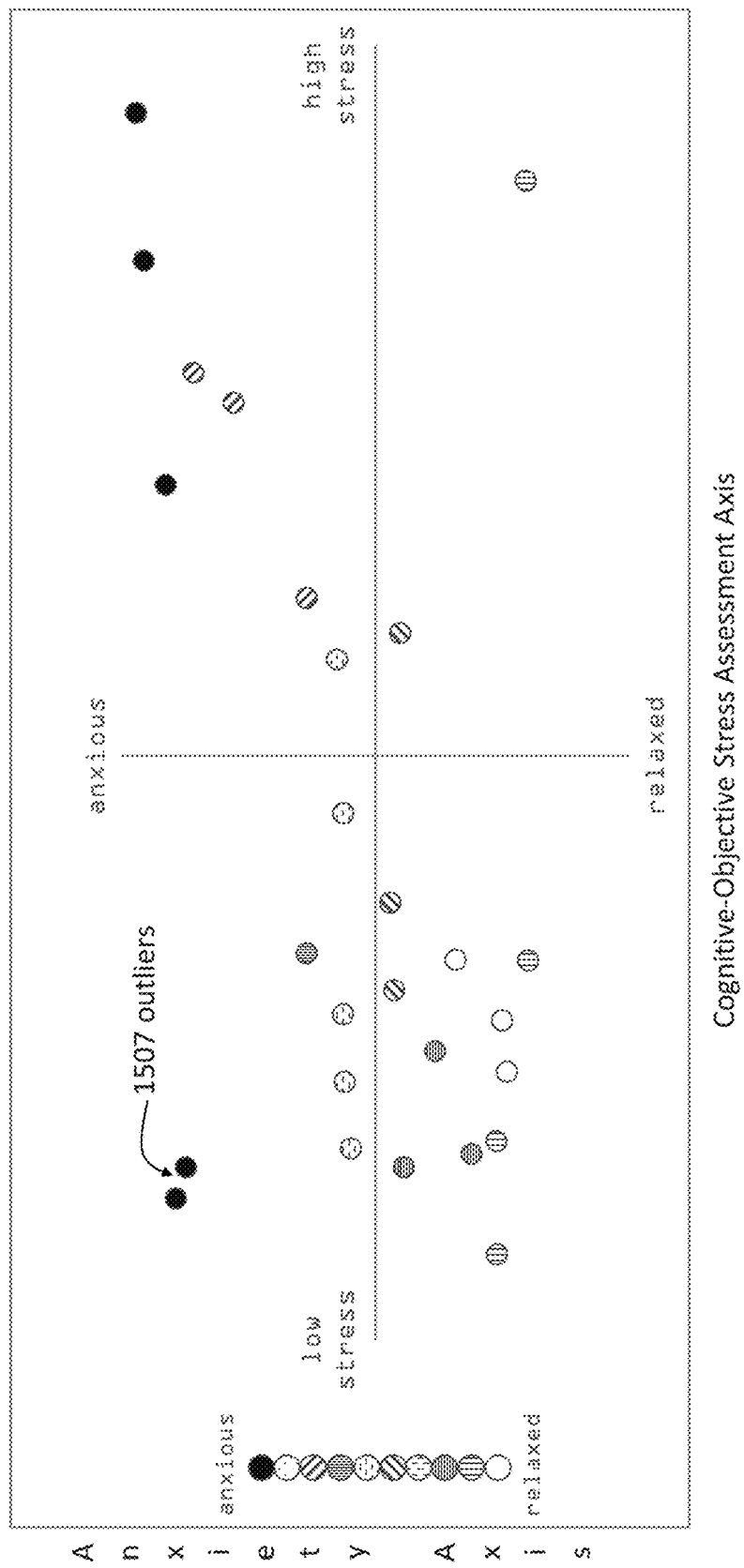
FIG. 15 is an exemplary scatter plot showing anxiety scores plotted against cognitive-objective stress assessment scores for a particular patient.

FIG. 15 is an exemplary scatter plot showing anxiety scores plotted against cognitive-objective stress assessment scores for a particular patient. In the scatterplot, the COS score is plotted on the x-axis, while the experienced, subjective anxiety scores are plotted on the y-axis. Anxiety scores are plotted in a lighter to a darker shade corresponding to a "relaxed" to "anxious" scores. In the example of FIG. 5, a correlation is seen between anxiety score and COS score, with higher subjective anxiety score values tending to occur during periods when higher reported COS scores were also reported. Two outlying values of relatively high anxiety scored occurring during periods when relatively low COS scores were reported are shown as the data points labeled 1507, outliers.

Figure 16:
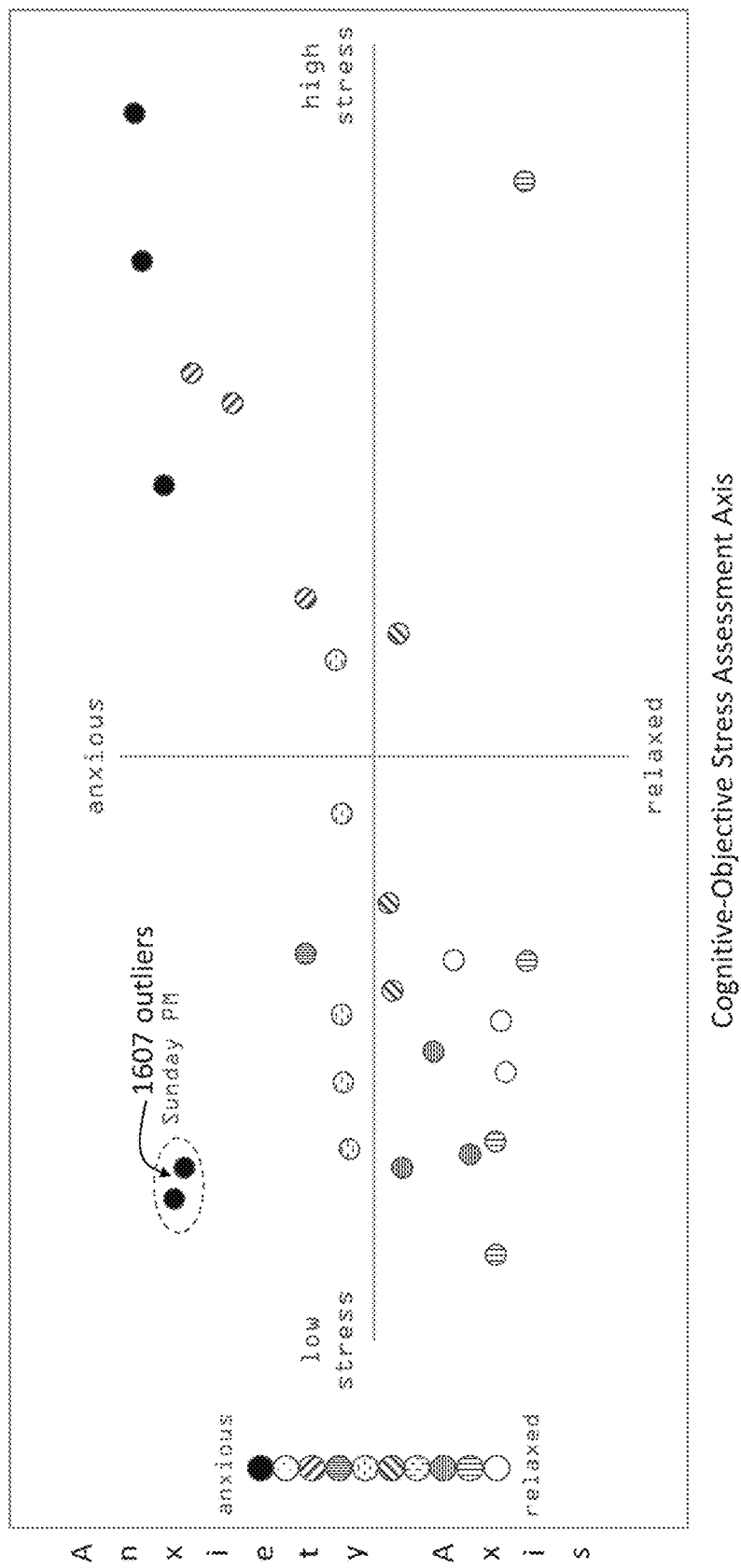
FIG. 16 is an exemplary scatter plot showing anxiety scores plotted against cognitive-objective stress assessment scores for a particular patient and showing two outlying values consistent with situational anxiety.
Figure 17:
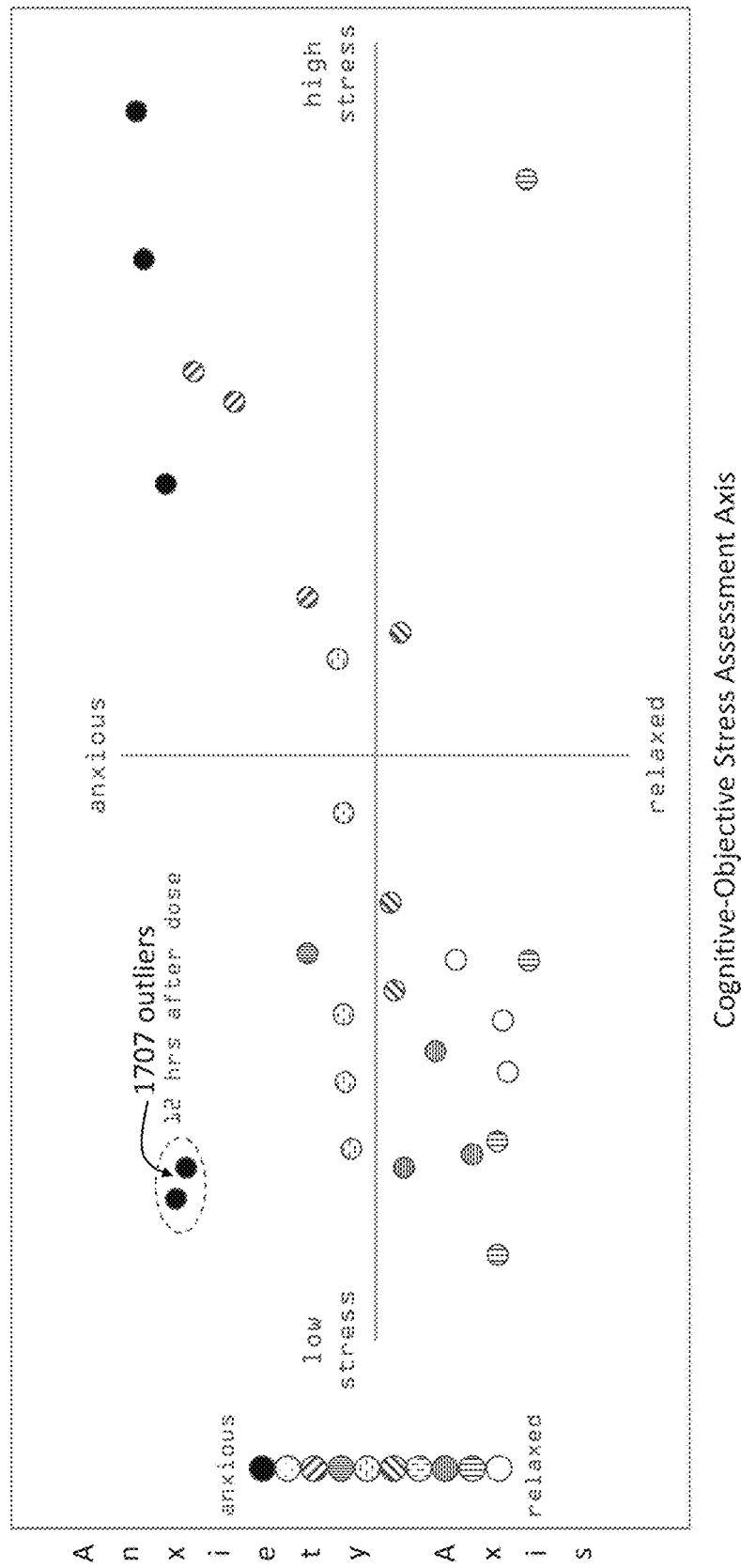
FIG. 17 is an exemplary scatter plot showing anxiety scores plotted against cognitive-objective stress assessment scores for a particular patient and showing two outlying values consistent with early withdrawal.

In an exemplary embodiment applied to anxiolytic medication, the method identifies discrepancies between the COS scores and subjective anxiety scores as shown, for example, in decision step 3010 of FIG. 3. In exemplary embodiments, it is determined if such a discrepancy occurs during a time that the model of medication tolerance/dependence that is currently being applied to the patient actually predicts an anxiolytic withdrawal event (e.g., as shown in decision step 3020 following step 3010 in FIG. 3). In the example illustrated in FIG. 15, the outlier data points do not correspond to a period during which withdrawal symptoms are predicted by the tolerance/dependence model currently being applied to the patient. In FIG. 16, it is revealed that the outlier points both occur during Sunday evening periods. In exemplary embodiments, the analysis of outlier data showing a discrepancy suggesting possible clinical indicators of early withdrawal, in this case identifies a pattern consistent with a certain situation, possibly suggesting anxiety related to anticipation of Monday morning stress or other stressful situations. In contrast, the same two outlying data points consistent with possible medication withdrawal consistently occur in FIG. 17, 12 hours after the last anxiolytic dose and although these events are not predicted by the tolerance/withdrawal model currently being applied to the patient, these outliers are not predicted by other circumstances (e.g., the common occurrence of Sunday evening stress/anxiety) and are consistent with unpredicted withdrawal signs and/or symptoms (e.g., as shown in decision step 3030 of FIG. 3). The scatterplot of anxiety scores vs Cognitive Objective Stress score is a useful visualization for patients and clinicians to evaluate episodes of anxiety against a more objective stress landscape in order to identify situational patterns that could be addressed behaviorally. Likewise, the method of adapting a model of anxiolytic medication tolerance/dependence to individual patients by identifying evidence of unpredicted withdrawal symptoms can also employ an analysis of the discrepancy between subjectively reported symptoms and objective analysis of the causative environmental milieu. In exemplary embodiments, methodologies described herein can be applied to analgesic medication management using a comparison of subjective pain scores and more objective assessments or sensor-based clinical signs. In other embodiments, the methodologies described herein can be applied to longer term, longer half-life antidepressant management, for example by identifying discrepancies between subjective mood scores and more objective analyses of depressive axes filtered through cognitive assessment vehicles to reduce the effect of exaggerated thinking and catastrophizing. The methodologies described herein could also be applied to amphetamine therapy for Attention-deficit/hyperactivity disorder (ADHD) by identifying potential withdrawal symptoms, for example anger or rage episodes that are not consistent with a social situation. In exemplary embodiments for amphetamine or methylphenidate therapy, disproportionate subjective feelings of anger or rage are identified using a Cognitive Objective Stress (COS) score that is targeted to help the patient analyze the social situation to objectively identify and score situations that may precipitate anger and to cognitively filter the reasonableness of the experienced anger by removing the effects of exaggerated or erroneous thinking that initiated or exacerbated the feelings of anger or rage. In exemplary embodiments, this subjective anger score vs COS score method can be applied, using the approach of decision step 3020 and 3030 to weigh possible amphetamine withdrawal events and adaptive models of amphetamine tolerance/dependence to individual patients.

Figure 18:
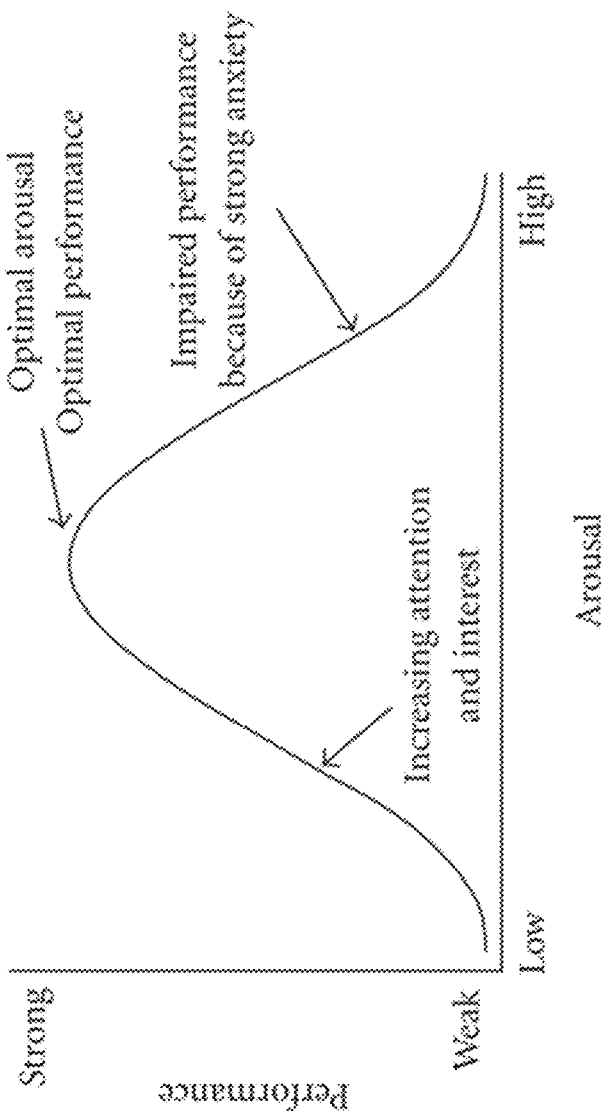
FIG. 18 is an exemplary graph illustrating the Yerkes-Dodson Performance Anxiety Curve.
Figure 19:
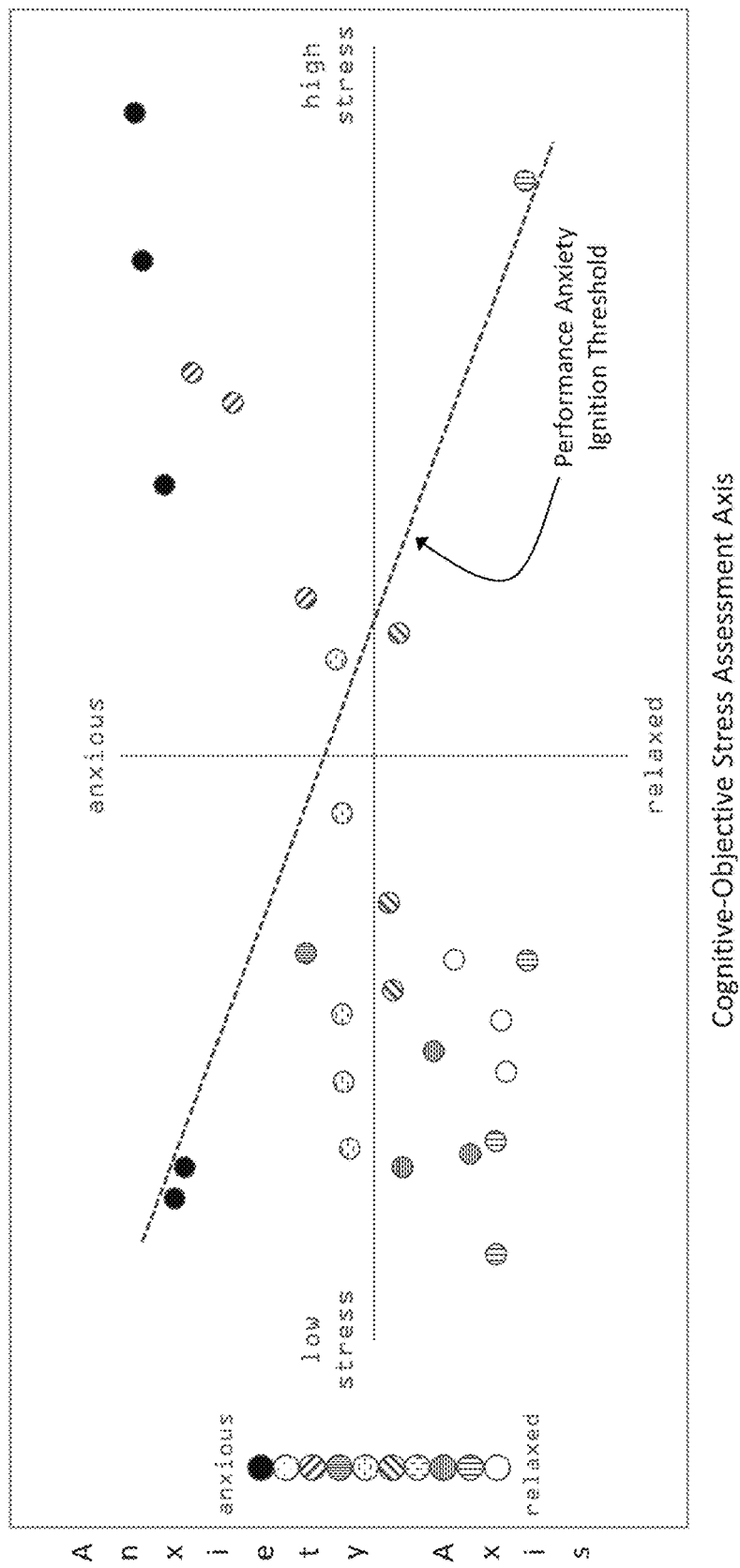
FIG. 19 is an exemplary scatter plot showing a performance anxiety threshold curve with lower threshold in high stress situations.
Figure 20:
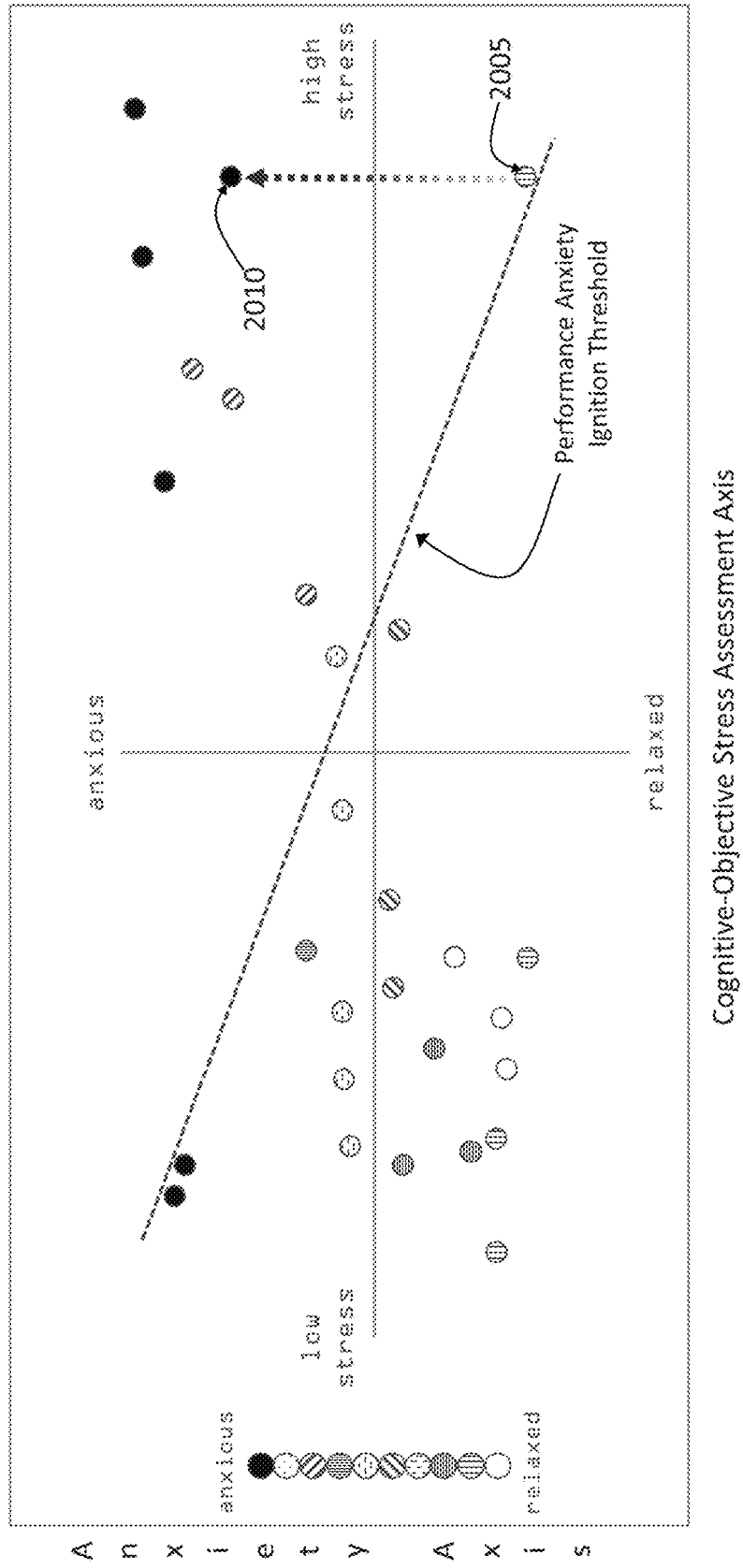
FIG. 20 is an exemplary scatter plot showing a performance anxiety threshold curve with lower threshold in high stress situations and showing ignition of anxiety during a high level of objective-cognitive stress but low initial anxiety score.

FIG. 19 shows a scatterplot of subjective anxiety scores plotted against cognitive objective stress scores for a patient. FIG. 20 shows the same scatterplot for the same patient but now including a single data point (labeled 2010) corresponding to a high subjective anxiety score and a high cognitive objective stress (COS) score. Analysis of the data by the method described herein reveals that the event 2010 occurs soon after event 2005, which is a point corresponding to a relatively low anxiety score and a relatively high COS score. In the method described herein, a rapid transition from a low anxiety score to a high anxiety score during periods of high cognitive stress is identified as a potential episode of performance anxiety and given a low weight as a possible medication withdrawal event (e.g., not consistent with unpredicted withdrawal of anxiolytic in step 3030 of FIG. 3). FIG. 18 is a graph showing the Yerkes-Dodson Curve which relates performance as a function of an "Arousal" state where low levels of arousal correspond to objectively justifiable stress which can actually increase performance, and higher levels of arousal correspond to anxiety which can cause thought paralysis which actually results in lower levels of performance. FIG. 19 and FIG. 20 show a dashed line labeled the "Performance anxiety ignition threshold" which corresponds to the Yerkes-Dodson curve in the sense that relatively mild initial subjective feelings of anxiety that occur during periods of high cognitive stress can quickly undergo an ignition phenomena which leads to amplified anxiety and at times panic, which can quickly cause a deterioration in performance that tends to cause additional anxiety. It is known that the threshold for the ignition phenomena tends to be lower in stressful situations (e.g., during periods in which the COS score is high). However, the performance anxiety threshold has significant interpatient variability. In the present method, COS scores, anxiety scores for individual patients are analyzed in order to identify ignition events that could correspond to performance anxiety and to develop a performance anxiety ignition threshold for the patient which can be displayed on the scatterplot graphic of FIGS. 19-20. The graphical display of the performance anxiety ignition threshold curve for a patient can give insight into the susceptibility to the performance anxiety, and could be used to monitor the effectiveness of medication and cognitive therapies aimed at treating this condition. Moreover, the identification of high stress scores associated with episodes of performance anxiety is used by the present method, which gives reduced weight to such clinical events as potential indicators of anxiolytic medication withdrawal (and for example, does not tend to modify the patient's anxiolytic tolerance/dependence model in decision step 3030 of FIG. 3). For example, the experience of anxiety (and the associated report of a relatively high anxiety score) during a relatively stressful situation (for example, a car accident) is not weighted by the system as evidence for anxiolytic medication withdrawal. A high score (e.g., of anxiety, COS, anxiety) is a score that is higher than an average population score by a predetermined percentage.

FIG. 21 is an exemplary scatter plot showing the display of average anxiety score vs. the average cognitive-objective stress assessment score for an individual compared to the average for the individual's cohort. In exemplary embodiments, the display is provided by display module 709 of FIG. 1B, for example implemented on medication recommendation mobile application client 4010 of FIG. 4. In exemplary embodiments which provide recommendations for anxiety and anxiolytic medication the display module presents a patient's time averaged or incident averaged subjective anxiety scores (plotted, for example, on the y axis of FIG. 21) versus the patient's Cognitive Objective Stress (COS) scores, (plotted for example on the x axis of FIG. 21) as well as the same scores for population or cohort groups. In exemplary embodiments, the patients' scores over time can also be displayed by display module 709. In other embodiments, the patient's average scores can be shown together with the average scores of individuals within a population or cohort, as shown in FIG. 22.

The visualizations of FIG. 21 and FIG. 22 enable a patient to compare cognitive objective stress scores and anxiety scores to unnamed individuals in a population and/or in cohorts. In exemplary embodiments, the patients scores can be displayed at different times, showing a trend as a result of treatment for example. This display of the patient's own scores together with that of population and or cohort groups can be used by a patient to compare their own situational and clinical situation to similar cohort groups. In exemplary embodiments, the average medication dosages of cohort groups can also be displayed. The average medication dosages of cohort groups can be used to motivate a patient toward a more self-controlled budgeting of self-administered anxiolytic or pain medications and to maintaining a de-escalating dosing schedule that avoids medication tolerance and dependence and which can lead to alternative maintenance therapies without medications, for example therapies based on cognitive behavioral therapy. In exemplary embodiments, the information is used to motivate patients toward medication de-escalation and medication-free therapies which may include group support chat and communication with anonymous members of the same cohort, or which may include remote sessions with a cognitive behavioral therapist. In embodiments, the clinician, prescriber, or cognitive behavioral therapist may also access the patient's Cognitive Objective Stress Scores, Anxiety Scores, Mediation dosing history, physiologic or sensor-based clinical indicators, as well as estimates of time to medication dependence for the patient and cohorts, for example using the HIPAA-compliant interfaces between the client device 4010 and the server 4020.

FIG. 23 is an exemplary diagram showing elements of a single-dose dispensing device in an initial rotational position. As discussed in conjunction with FIG. 1C (e.g., steps 620 and 622) and dispenser control module 707, the present method of estimating a time until medication tolerance/dependence can be used to control a secure, single-dose administration device that is electronically paired to, or otherwise communicates with a client (e.g., client device 4010 of FIG. 4) or server (e.g., server 4020 of FIG. 4) embodiment of the present method.

Figure 23C:
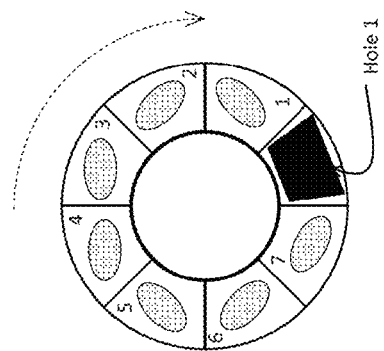
FIGS. 23A, 23B, and 23C are exemplary diagrams showing elements of a single-dose dispensing device in an initial rotational position.
Figure 23B:
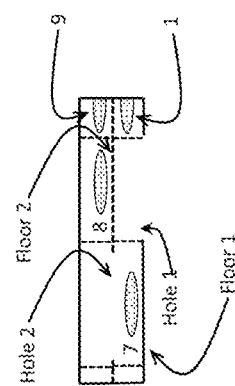
Figure 23A:
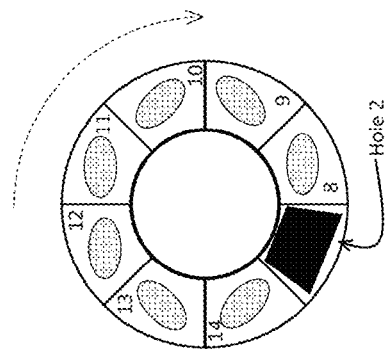

FIGS. 23A, 23B, and 23C show a rotary single-dose medication dispensing device based on a two-floor design in a first position before any rotation with zero tablets dispensed. In FIGS. 23A, 23B, 23C, the locking mechanism is not shown and an exemplary locking mechanism is shown in FIG. 25. FIG. 23C shows a bottom level which is arranged as ring of sections labeled 1-7 and separated by dividers which rotate across a closed base or floor of the disc shaped container for the bottom level the floor is labeled Floor 1 in the side view FIG. 23B. In each floor of the device, there is a hole in the floor in a fixed position. For example, the hole in Floor 1 of the bottom level of the disc shaped dispenser is labeled Hole 1 in FIGS. 23B and 23C. When the dividers are rotated for a floor, the dividers sweep a single dose of medication to the hole in the floor. For the bottom level floor, a rotary movement of the dividers by one position allows a single dose of medication to leave Hole 1 and thereby exit the device. A second floor, labeled floor 2 in FIG. 23B and indicated by a dashed line has a hole in a single position labeled Hole 2 in FIG. 23A and FIG. 23B.

Figure 24A:
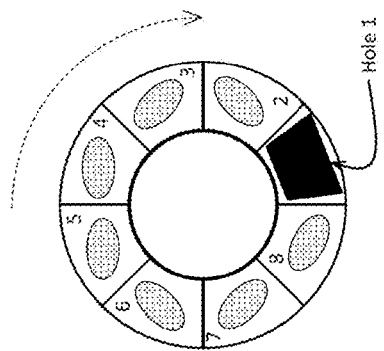
FIGS. 24A, 24B, and 24C are exemplary diagrams showing elements of a single-dose dispensing device in a subsequent rotational position.
Figure 24B:
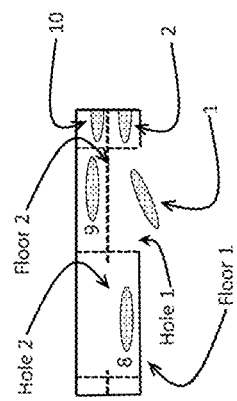
Figure 24C:
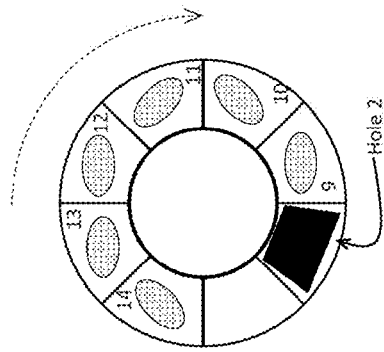

FIGS. 24A, 24B, and 24C show the two-floor embodiment of FIGS. 23A, 23B, and 23C, in a second rotational position, with one tablet dispensed through Hole 1, and one tablet moving from the upper level to the bottom level through Hole 2 in Floor 2, having advanced only one rotary position. FIGS. 24A, 24B, and 24C show that tablet 1 is swept out of hole 1 and tablet 8 is swept from its initial position on the upper level floor (shown in FIGS. 23A. 23B, and 23C) to its new position on the bottom floor.

FIG. 25A shows detail of the bottom level of the two-floor embodiment of FIGS. 23A, 23B, and 23C and both levels in a side view. A lock 2500 (such as a locking pin or slide) is labeled as Lock 1 in both the top view of the bottom level and the side view. A central rotor 2502 which is configured to admit the lock 2500. In exemplary embodiments, the rotor rotation is connected to the rotating dividers for each floor of the device and free rotation of the rotor by a single rotational position allows free rotation of the rotating dividers for each floor also by a single rotational position. FIG. 25A shows the lock 2500 in the locked position which prevents rotation of the rotor and therefore also prevents rotation of the rotating dividers separating the tablets. FIG. 25A also shows a mobile device (e.g., a smart phone, a tablet, a watch, a fitness appliance, or other device) or server system that may be in communication with the exemplary two-level single-dose dispensing device. In exemplary embodiments, the Mobile App or Server COMM system may send a signal to the two-level dispensing device which may be a near-field communication pairing or signal, a Bluetooth, wifi, 4G or other wired or wireless signal which causes the lock 2500 slide to actively or passively disengage the rotor 2502, allowing rotation of the rotor 2502 (and the rotating dividers separating the individual doses of mediation) to advance one rotational position before the lock 2500 automatically engages with rotor 2502, preventing the rotation beyond a single rotational position. Exemplary embodiments can employ a spring loading of the lock 2500 and an appropriate angular arrangement of the impressions in rotor 2502 in order to limit advancement by a single rotational position as a result of a single disengagement or unlocking of the lock 2500. In some embodiments, the lock 2500 is implemented as a pin or a slide which engages the rotor 2502. In exemplary embodiments, the pin or slide can be disengaged using a mechanical or electromechanical, or magnetic techniques. In exemplary embodiments, the slide or pin comprising the lock 2500 can itself be restricted from disengagement by a smaller pin, slide, or other restriction mechanisms and upon disengagement of this restriction the larger, more substantial lock 2500 slide or pin is free to disengage the rotor 2502 by a centrifugal force applied by spinning the entire dispenser. This allows a "slide" implementation without the need for a large on-board power supply or additional mechanisms of imparting mechanical advantage between an electrical or other powered disengaging mechanisms. In exemplary embodiments, individual medication doses can be pre-packaged in a disposable reel comprising a single medication dose for each segment of the reel and the locked, paired, single-dose, rotational dispenser device can employ a similar locking slide or pin which is unlocked by the Mobile App or Server COMM in order to allow advancement of the disposable medication by only one rotational position at a time (for example after unlocking only one rotational position the lock pin or slide reengages to prevent another advancement of the rotational mechanism and thereby prevent more than one rotational advancement of the reel at one time). In some implementations, the device is disposable. Other embodiments are possible in which the main locking mechanism is reusable and controls a disposable component which can only be opened by docking to a paired locking device (e.g., using NFC pairing of the two components of the administration device, with the locking component also paired to a controlling application (e.g., client device 4010 of FIG. 4)

In exemplary embodiments, a slide or pin lock (e.g., lock 2500) automatically reengages and locks the rotor mechanism (e.g., Rotor 2502) using a cam linkage and or a spring linkage between the rotor (e.g., Rotor 2502) and the slide or pin lock (e.g., Lock 2500).

FIG. 25B shows the same dispenser depicted in FIG. 25A, but in FIG. 25B, the lock 2500 has been unlocked by a wireless signal from the Mobile App, Server COMM, the server 4020, or the client device 4010 and is now disengaged from the rotor 2502.

FIG. 25C shows the same dispenser depicted in FIG. 25B, but now the rotor 2502 and the rotating dividers have been advanced by one rotational position (tablets on the second floor are not shown to improve clarity of the figure). In this case, tablet 1 has been dispensed (through Hole 1, which is omitted for clarity but corresponds to the Hole 1 position labeled in FIGS. 23A, 23B, 23C, 24A, 24B, and 24C.

FIG. 25D shows the rotor 2502 and the rotating dividers in the same position as FIG. 25C, but now the lock 2500 has reengaged the rotor 2502, preventing rotation beyond a single rotational position at a time.

In some embodiments, the rotary portable dispenser has a small diameter and many levels and takes a form factor of a tube or pen-like device. In such embodiments, the locking pin or slide (e.g., Slide 1) is controlled by the electronically paired Mobile App or Server COMM, and the rotor (e.g., Rotor 1) is advanced manually using a pen-top like push button at one or more ends of the device that advances the rotor, for example using a cam. In some embodiments, the dispenser uses a weakened cam or other weakened rotor-advancing mechanism so that manual forcing of the pen-top advance unit if the slide or pen mechanism has locked will cause the cam to break, preventing further advance of the rotor. In some embodiments, special low-dose or small form-factor formulations of a medication can be used to increase the precision of the administration, and/or to allow more doses to be accommodated in a portable secured, electronically paired, single dose administration device. In some embodiments, the medication is formulated into a specific shape so as to be administered only by a specific controlled single-dose administration device which accommodates that shape. In embodiments, the shape specificity can be used to provide greater control and specific device compatibility.

FIG. 26A is an exemplary diagram showing a locked, secure, single-dose medication dispensing device 2600 that is paired to and controlled by a Mobile app or Server COMM (e.g., in step 620, the dispenser control module 707), and having two independent rotary sweep mechanisms configured to be unlocked independently. In exemplary embodiments, a lower or bottom level including a first lock 2602 (e.g., implemented as a slide or pin), a first rotor 2604, and connected rotating dividers 2610 and associated floor with hole (e.g., Floor 1 with Hole 1) comprises a rotary level that is controlled independently from a higher or upper level which has a second independent lock 2606 (e.g., implemented as a slide or pin), a second rotor 2608, and connected rotating dividers 2612 and associated floor with hole (e.g., Floor 2 with Hole 2). In exemplary embodiments, the dose of mediation stored on one level of the single-dose administration device is a smaller dose of the same medication that is stored in a different level of the single-dose administration device. In such embodiments, the medication recommendation device, communicating using Mobile App or Server COMM shown in FIG. 26A (e.g., implemented as the Medication Recommendation Mobile application on the client device 4010, or the Server 4020 of FIG. 4) can unlock a larger or a smaller dose of a mediation (e.g., in step 4030 of FIG. 4, dispenser control module 707 of FIG. 1B). Such embodiments provide more precision in the administration of the controlled medication, since the device can make a recommendation of a smaller dose of medication if the medication tolerance/dependence method determines that the smaller dose would potentially be useful to reduce the risk of developing tolerance/dependence for the medication, or if a smaller dose would allow the patient to remain compliant with a de-escalation regimen currently recommended by the system, while making available a reduced dose of medication to treat or prevent symptoms during the de-escalation period. In some embodiments, the two levels of the dispenser may contain different medications that are under control of separate dispenser control modules (e.g., Module 707 of FIG. 1B) under the control of separate modules to determine and display a conservative estimate of the time until medication dependence (e.g., in step 612 FIG. 1C, the tolerance module 705, and the dependence module 706 FIG. 1C). An advantage of the multi-dose administration method, described herein, is that it provides greater precision in both administration recommendations as well as accounting for actual dosages taken, since many "as needed" medications can be scored into smaller doses by the patient, but with now systematic accounting method for recalling how many tablets have been scored, the patient often has no good estimate of the amount of medication taken and the amount of medication remaining. In exemplary embodiments, the separate sections of the rotary dispenser shown in FIG. 26A can take a tubular or pen-like form factor with different doses of medications or different medications being issued from different ends of the tube.

FIG. 26B is an exemplary diagram showing elements of a single-dose dispensing device having an outer dispensing ring and at least one inner dispensing ring. In exemplary embodiments an inner ring contains a smaller dose of a medication than the outer ring.

Figure 27:
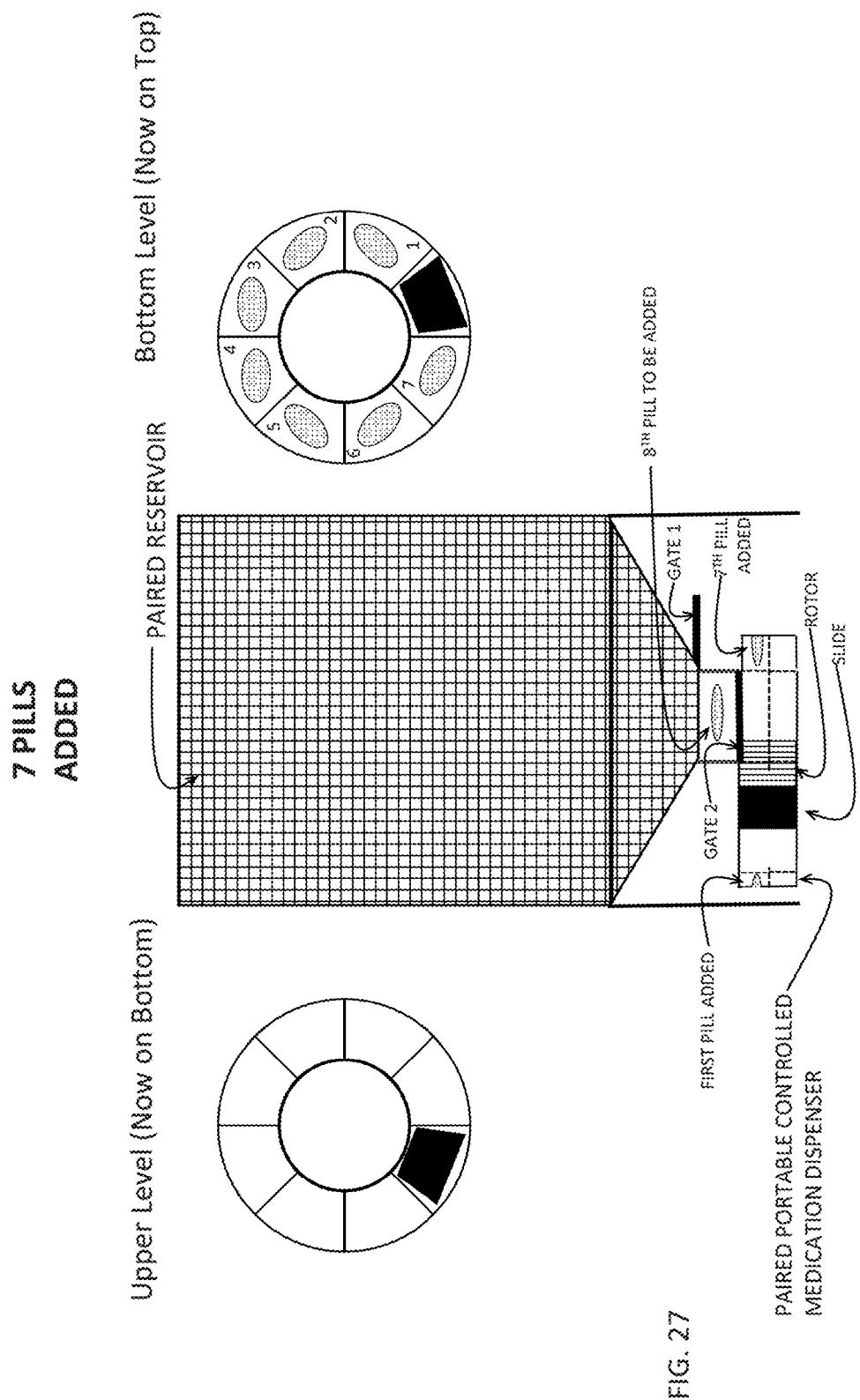
FIG. 27 is an exemplary diagram showing a high-capacity dispensing reservoir securely docked to a portable single-dose cascade dispensing device in a first step of rotational filling of the cascade.
Figure 28:
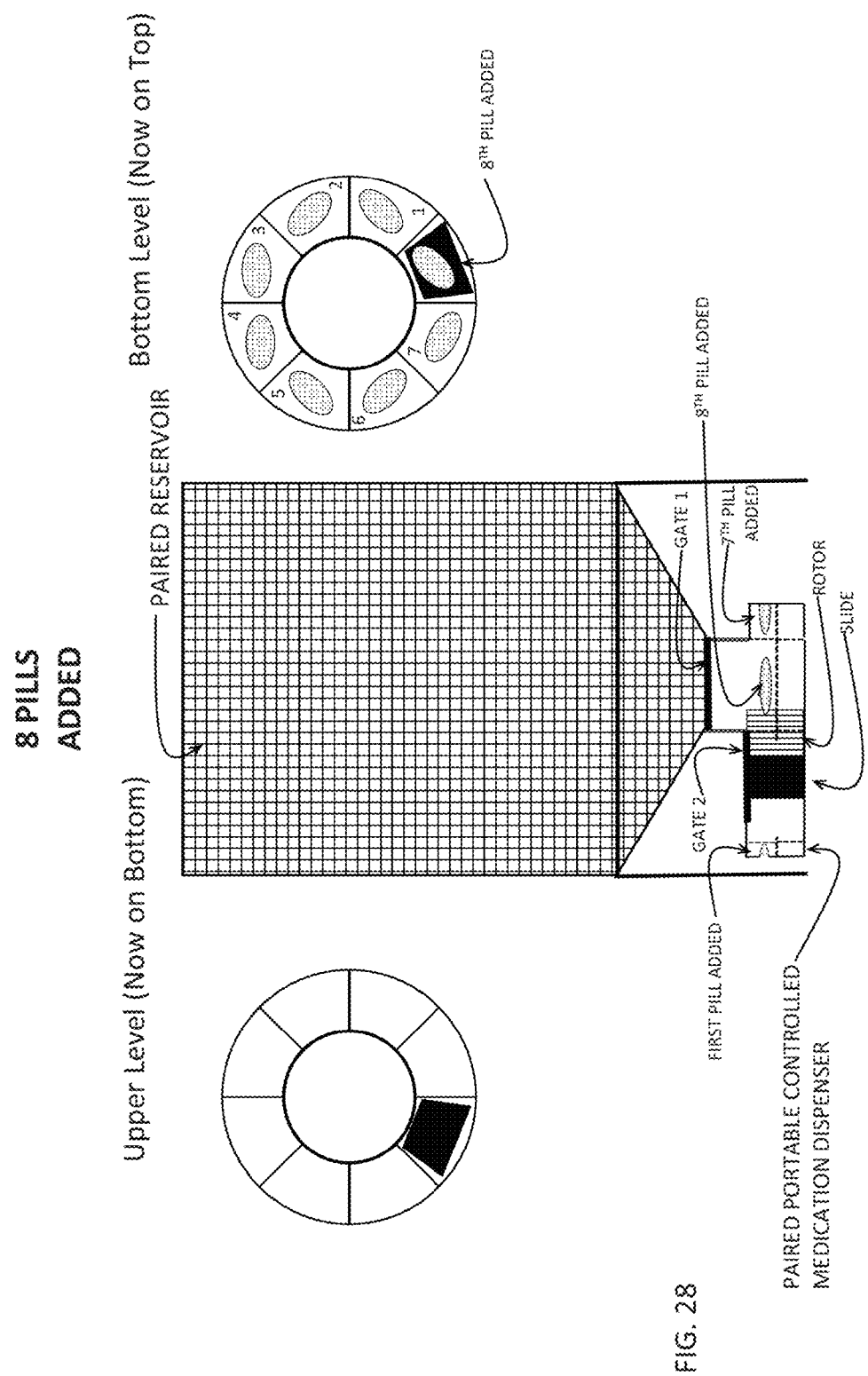
FIG. 28 is an exemplary diagram showing a high-capacity dispensing reservoir securely docked to a portable single-dose cascade dispensing device in a second step of rotational filling of the cascade.
Figure 29:
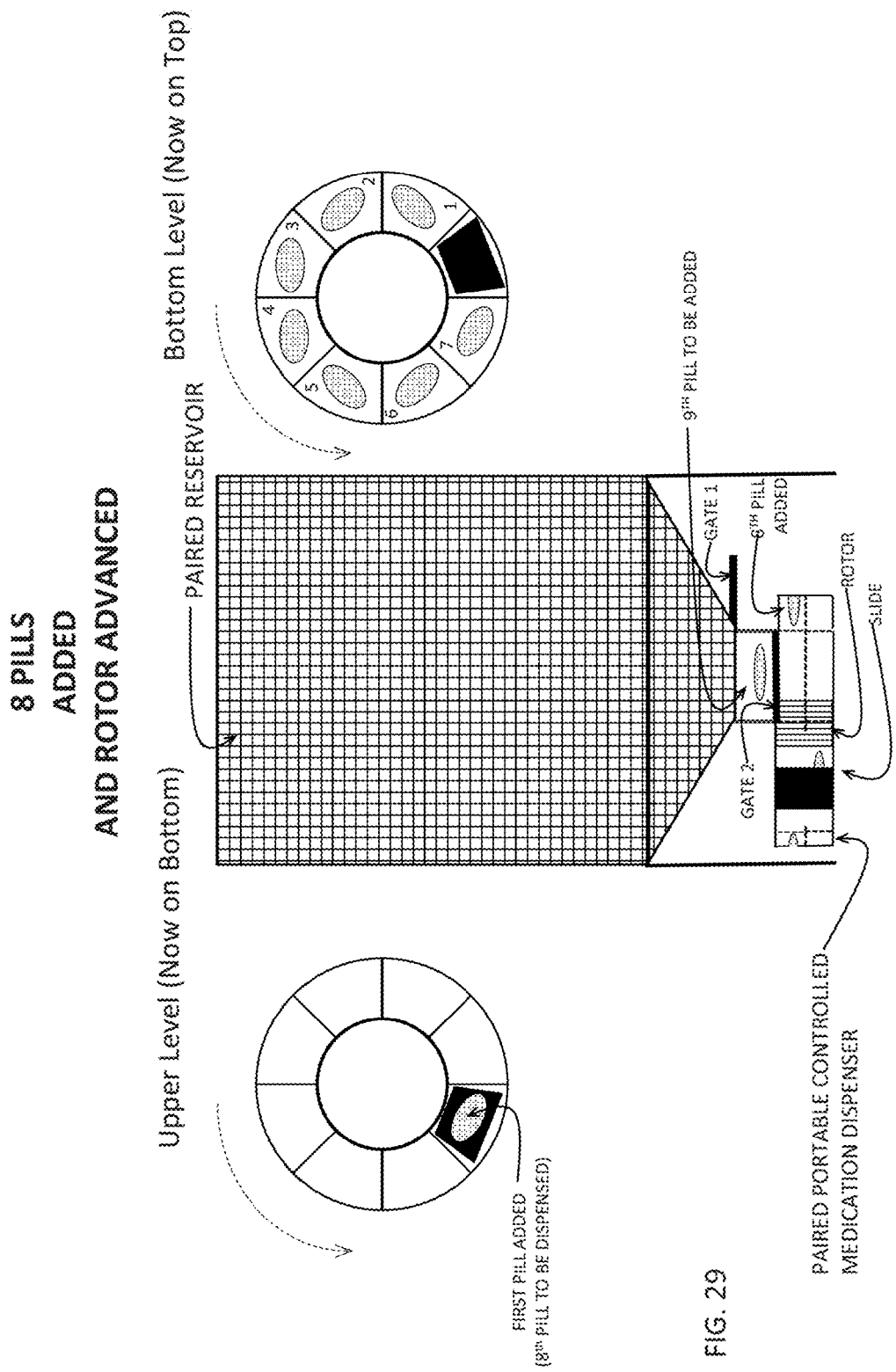
FIG. 29 is an exemplary diagram showing a high-capacity dispensing reservoir securely docked to a portable single-dose cascade dispensing device in a third step of rotational filling of the cascade.

FIG. 27 is an exemplary diagram showing a high-capacity dispensing reservoir securely docked to a portable single-dose cascade dispensing device in a first step of rotational filling of the cascade. FIG. 27 shows an exemplary embodiment in which a portable rotary single-dose medication dispenser (e.g., FIGS. 25A, 25B, and 25C) is inverted (so that the hole in the floor is facing up) and is docked with a paired secure medication reservoir (e.g., labeled Paired Reservoir). FIG. 27 illustrates the process of filling the portable rotary device from the larger paired reservoir and shows the state of filling of the rotary single dose medication dispenser after 7 pills have already been added. In embodiments, the paired portable controlled medication dispenser is inverted and attached to the paired reservoir. In some embodiments, a motor or other actuator is used to advance the rotor one rotational position each time the slide is opened once. In exemplary embodiments, one section of the rotary portable device is filled by opening gate 1 of the reservoir to admit a single pill into the reservoir's chamber between gate 1 and gate 2, then closing gate 1 of the reservoir and opening gate 2 of the reservoir and allowing the single pill from the chamber to advance into an empty section of the portable device, as shown in FIG. 28. In a next step, gate 2 is closed and gate 1 is opened to admit the next pill into the reservoir's chamber. Then the rotor is advanced one rotational position, exposing the next open section of the portable device to the hole in the inverted portable device, as shown in FIG. 29 which illustrates the slide in an open or unlocked position and the rotor advanced, adding the $8^{th}$ pill in the sequence and exposing another open section of the portable device. The process repeats until the portable device is filled from the reservoir.

Exemplary embodiments can employ a hybrid single-dose dispenser having a gravity feed at the top controlled by one or more slides which accommodate a single dose of medication through a chamber into a rotary section which advances a rotor to sweep a single dose through a hole in the floor of the device. Such hybrid embodiments allow greater capacity in small tubular (e.g., pen-like) form factors. Such embodiments have the capacity advantage of the reservoir, while also having increased tamper-proof security provided by a 2 or 3 level rotary cascade between the hole and the reservoir.

A tubular embodiment employing a hybrid gravity feed with gates and a cascade feed with floor holes, and using a push top which motivates a cam driving an unlocked rotor is shown in FIG. 30A, in a pen-like embodiment. The reservoir labeled Integrated Reservoir increases capacity in a narrow-aspect form factor, since less space is taken up by rotary sections having one section requiring a hole for each level of the cascade. The reservoir is configured to admit pills to the cascade through gates 1 and optional gate 2, controlling passage through Chamber 1. In embodiments, gates 1 and 2 may have different electronic unlocking controls (e.g., via a wireless signal from Mobile App or Server COMM, using the dispenser control module 707 of FIG. 1B) than lock 3000 (which controls the advance of the pill cascade using the rotor), giving extra security. In exemplary embodiments, the bottom level hole in the floor can be offset from the upper reservoir chamber, making the device less susceptible to tampering using a single linear tool through both the cascade hole and the reservoir gates and chamber.

Some embodiments of the present method of a secure, single-dose medication dispenser that is paired and controlled by an unlocking device incorporate a method of detecting when the dispensing device has been tampered with and reporting such an event, for example to the server 4020 shown in FIG. 4. Such embodiments enable the physician prescriber, or other accountable care organization, dispensing pharmacy, or regulatory agency to be notified of malfunction of, or exploitative tampering with the single-dose dispensing portal device or reservoir.

Figure 30B:
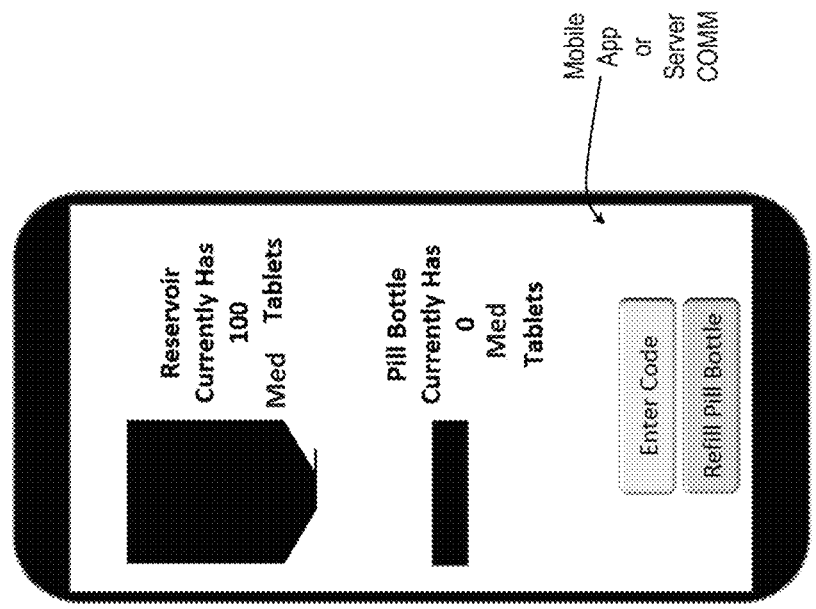
FIG. 30B is an exemplary diagram showing a display of a portable application controlling the filling of the portable single-dose dispensing device from the high-capacity dispensing reservoir.

FIG. 30B is an exemplary diagram showing a display of a portable application controlling the filling of the portable single-dose dispensing device from the high-capacity dispensing reservoir. In exemplary embodiments, paring of the portable device and the reservoir device to the Mobile App or Server COMM (e.g., the client device 4010 of FIG. 4). In exemplary embodiments, the electronic paring is established through Near Field Communication (NFC) or other secure protocol and employs encryption and authentication to establish a secure pairing and control. In embodiments, the mobile application can display the current remaining doses of medication in the reservoir and the portable dispensing device and can issue warnings of low remaining doses to the patient and/or the prescribing provider.

Figure 30C:
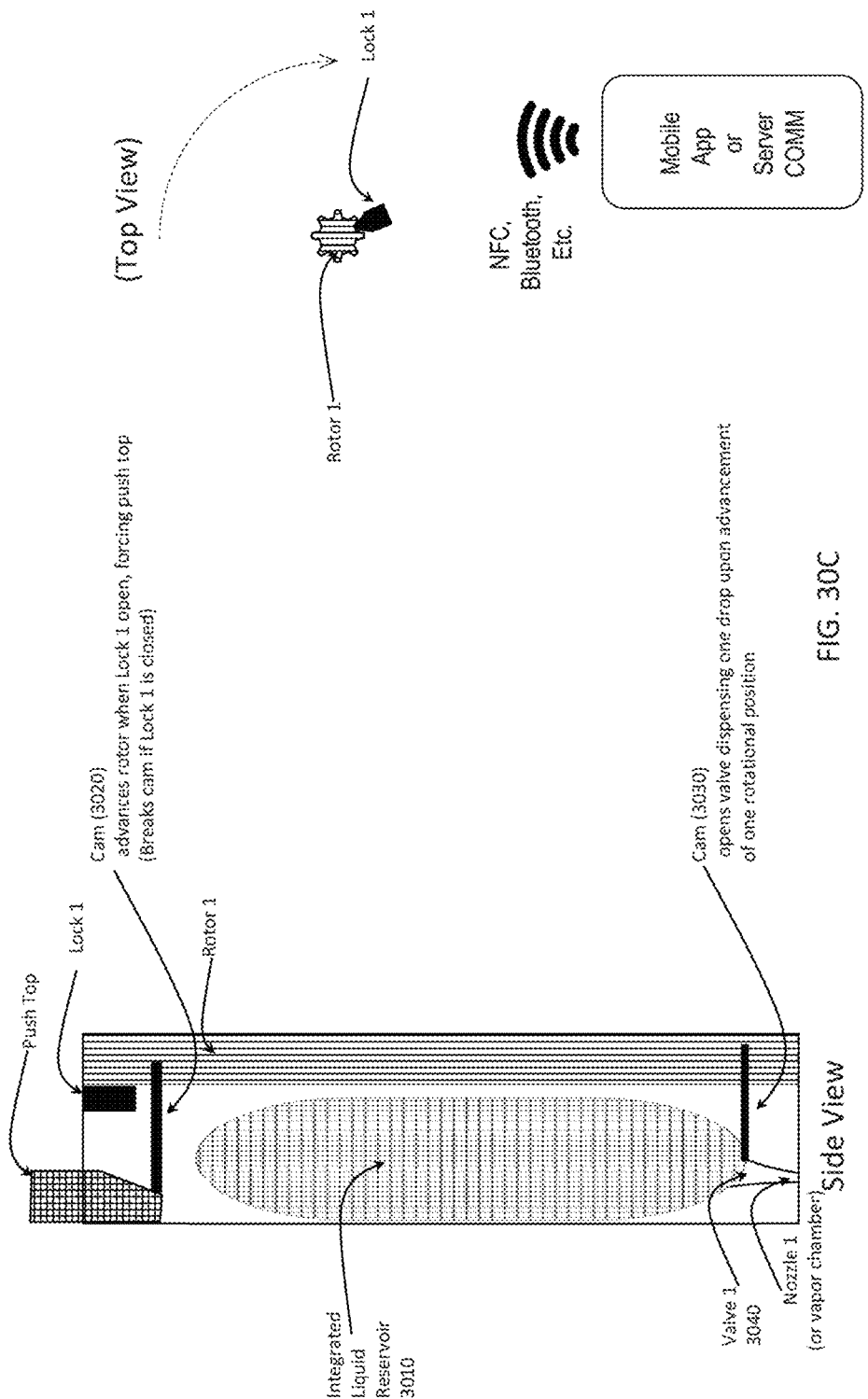
FIG. 30C is an exemplary diagram showing a showing a secure, single-dose medication liquid medication dispenser using a liquid reservoir.

FIG. 30C is an exemplary diagram showing a showing a secure, single-dose medication liquid medication dispenser using a liquid reservoir. In exemplary embodiments, the dispenser is electronically paired via a wireless or hard-wired connection, for example to the Mobile App or Server COMM (e.g., the client device 4010 or the server 4020). In embodiments, an integrated liquid reservoir (e.g., reservoir 3010 in FIG. 30C) contains the medication in dissolved, suspended, or other liquid preparation. In some embodiments, the lock is controlled by a control signal (e.g., step 620 or step 622 in FIG. 1C, or module 707 in FIG. 620). FIG. 30C shows a push top which engages a first cam 3020. In some embodiments, a cam or other advancing means may advance a rotor (e.g. Rotor 1 of FIG. 30C) if a rotor lock (e.g. Lock 1 shown in FIG. 30C) is not in a lock position. In some embodiments, a locking mechanism such as Lock 1 is controlled by a wired or wireless communication such as Mobile App or Server COMM shown in FIG. 30C sending an NFC, Bluetooth or similar signal causing the Lock to unlock and allowing a rotor (e.g. Rotor 1) to move one rotational unit. FIG. 30 also shows a second cam 3030, connected to Rotor 1 and actuating a liquid valve 3040. In some embodiments, the liquid valve 3040 may be controlled directly using an electrical, electrical-mechanical, pneumatic or other means, for example via a signal from the Mobile App or Server COMM using a wireless protocol. As described in conjunction with FIGS. 1-4, FIG. 35 and FIG. 36, in some embodiments, the system 500 (e.g., the client device 4010) can initiate signals unlocking or otherwise activating the single-dose liquid medication dispenser shown in FIG. 30C only when the controlling systems determines that a likelihood of medication dependence is below a predetermined or dynamically re-determined threshold, for example, if the estimated time until a patient may become dependent on a medication is determined to be greater than a threshold time period. In some embodiments the mechanical, electrical, or pneumatically operated liquid valve can be operated so as to provide a variable medication dose to a patient (e.g. drop size), dependent upon the patient's current state of medication dependence, as estimated by the medication tolerance/dependence methods and systems described in FIGS. 1-4, FIG. 35 and FIG. 36. In some embodiments of the locked, single-dose medication dispensing method and system controlled using an ongoing estimate of the patient's time until medication dependence is estimated to develop, a concentration liquid form of the medication and dispensing means can allow a smaller and/or more secure implementation (e.g. using more substantial armoring of the device, while keeping size and cost lower. In some embodiments, the dispensation of different dose sizes can be me made with greater precision using a liquid form and liquid dispenser.

In some other embodiments, the medication in liquid form is metered through a locked, controlled valve (e.g., Valve 1) into a nozzle (e.g., Nozzle 1) for dispensing as liquid form. In other embodiments, the dose of the liquid medicine is metered through the locked, controlled valve (e.g., controlled by systems and methodologies described herein for estimating medication tolerance/dependence) and released into a vaporization chamber for administration as a vapor.

Figure 31A:
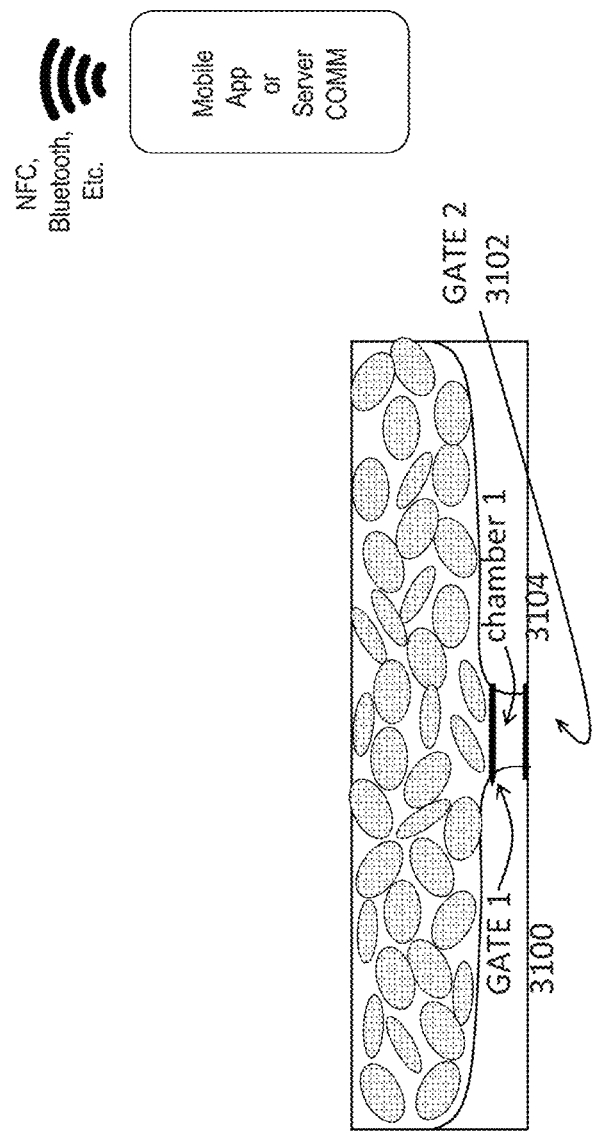
FIGS. 31A and 31B are exemplary diagrams showing a secure-single dose medication dispensing device using a shake-facilitated feed into a lock chamber controlled by two gates, in a first stage of lock chamber operation.
Figure 31B:
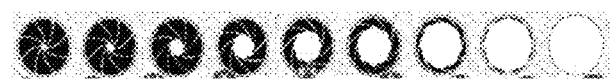

FIG. 31A is an exemplary diagram showing a secure-single dose medication dispensing device using a shake-facilitated feed into a lock chamber controlled by two gates, in a first stage of lock chamber operation. In some embodiments, the gates can employ available low-power iris devices that are commonly used in cell-phone and other small cameras, as shown in FIG. 31B. In exemplary embodiments, the reservoir employs a slanted or parabolic shape that facilitates gravity feed toward a first gate 3100. Upon unlocking of the device in order to administer a single medication dose (for example, module 707 in FIG. 1B).

Figure 34:
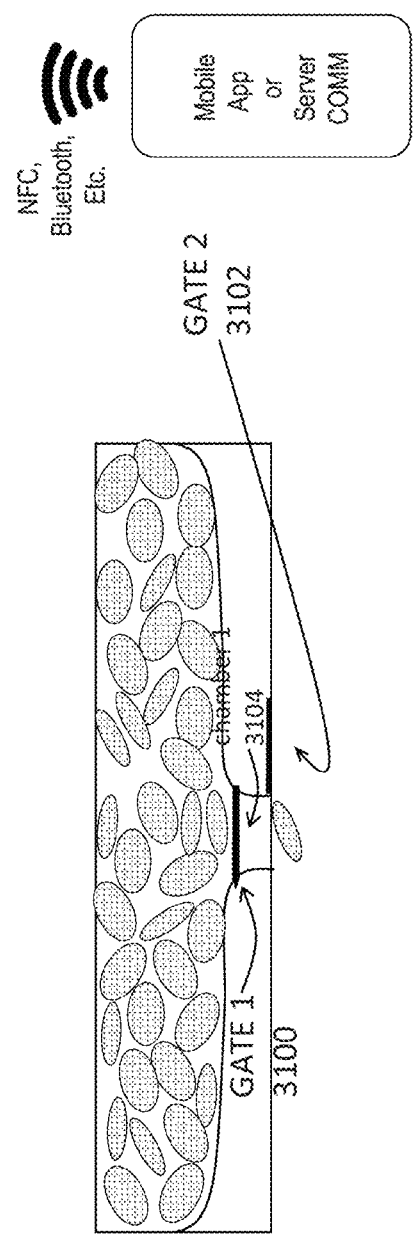
FIG. 34 is an exemplary diagram showing a secure-single dose medication dispensing device using a shake-facilitated feed into a lock chamber controlled by two gates, in a fourth stage of lock chamber operation.

In exemplary embodiments, the first gate 3100 opens under wireless or hard-wired control of Mobile App or Server COMM, admitting a single dose of medication to a chamber 3104. In some embodiments, a sensor (not shown) such as optical sensor determines if a dose of medication has been admitted to the chamber 3104 (e.g., as shown in the exemplary diagram FIG. 32). In embodiments, if a single dose of medication fails to enter the chamber 3104, then a light or other indicator on the device or a warning is communicated to the Mobile App or Server COMM to indicate to the user that the chamber 3104 is not prepared which may be corrected by shaking the device. In exemplary embodiments, when the chamber 3104 is populated by a single dose of medication, for example as determined by the sensor (not shown), then the first gate 3100 closes, after which the second gate 3102 can open, allowing a single dose of medication to leave the device, as illustrated in FIG. 34. In some embodiments, the first gate 3100 and the second gate 3102 are offset so that the gates are less susceptible to damaged by a probe introduced into an outer gate (e.g., the second gate 3102) of the single-dose administration device.

FIG. 35A is an exemplary diagram of a known method of modeling medication tolerance using a homeostatic physiologic model, according to the method described in *Intermittent Adaptation: A Mathematical Model of Drug Tolerance, Dependence and Addiction*, Peper, Abraham in *Computational Neuroscience of Drug Addiction*, Springer Series in Computational Neuroscience 10, DOI 10.1007/ 978-1-4614-0751-5_2, © Springer Science+Business Media, LLC 2012, incorporated herein by reference in its entirety. The tolerance model of FIG. 35C can be applied to both receptor agonistic medications and antagonistic medications and is based on a compensatory modulation or signal $S_{adapt}$ that is determined by a slow regulator, a fast regulator, and interval regulator which produces a multi-compartment like model having different time constants and a general first-order behavior. Exemplary embodiments of the present method can incorporate such homeostatic models of medication tolerance as a baseline or population model of medication tolerance (e.g., in step 610 in FIG. 1C) which can then be personalized to a patient, for example using the method of FIG. 3 and/or FIG. 35D, and improved with additional data using statistical and machine learning methods, as shown in FIG. 36.

FIG. 35B is an exemplary diagram of a known method of modeling medication tolerance using a model of receptor induction according to the method described in *Modified 'Joyce model' of opioid dependence/withdrawal*, Robert B. Raffaa and Ronald J. Tallaridab, Eur J Pharmacol., 2006 Dec. 3; 551(1-3): 54-57 incorporated herein by reference in its entirety. This model accommodates a multi-compartment model of receptor induction kinetics which can be used as a baseline or population model of medication tolerance (e.g., in step 610 in FIG. 1C) which can then be personalized to a patient, for example using the method of FIG. 3 and/or FIG. 35D, and improved with additional data using statistical and machine learning methods, as shown in FIG. 36.

Other embodiments are possible which employ alternate models of medication tolerance as the baseline or population model to be personalized and improved with additional data.

Figure 35E:
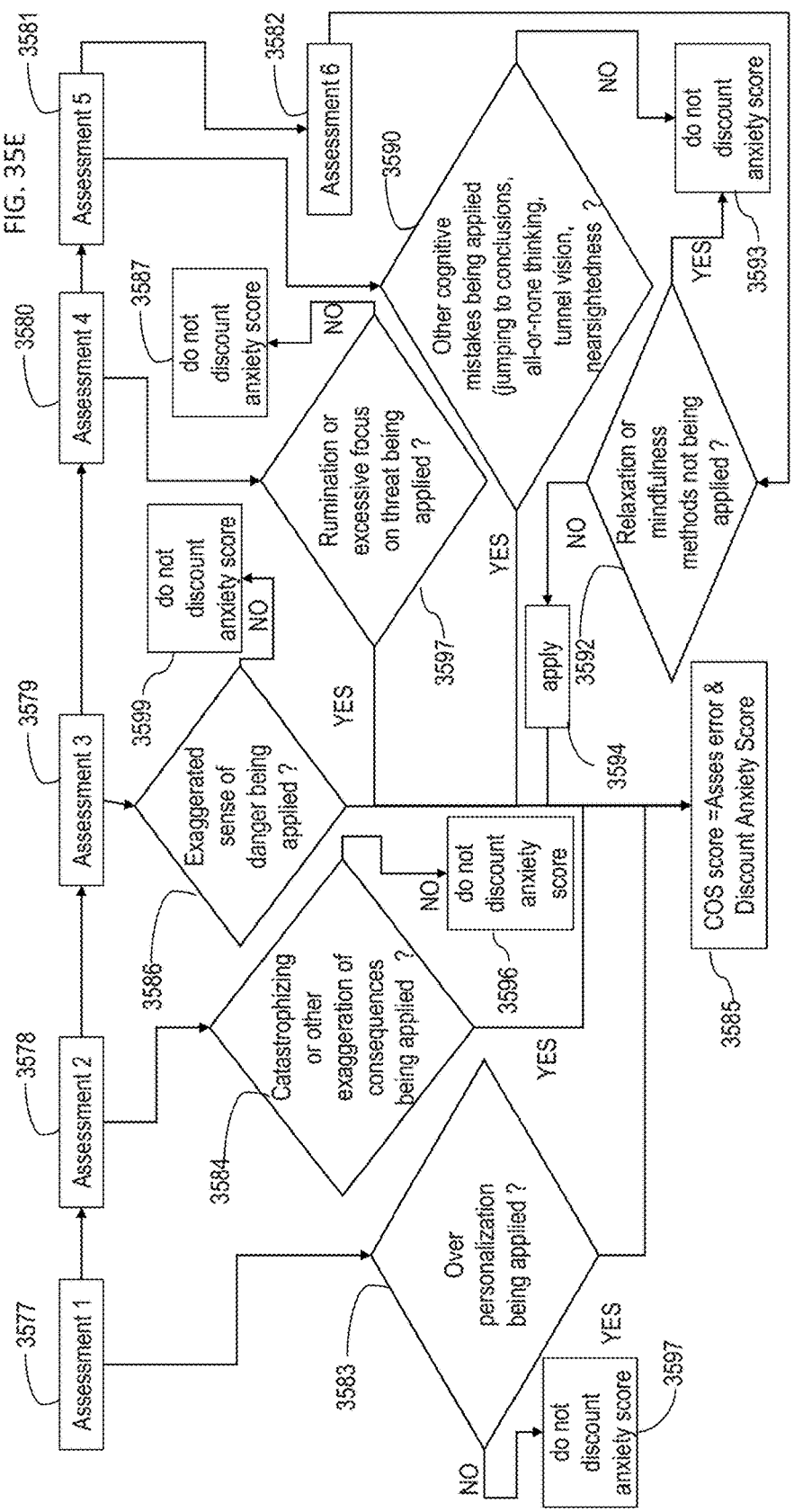
FIG. 35E is an exemplary flow diagram showing a method of determining a cognitive objective stress score from an anxiety score by applying cognitive skills and methods to make real-time adjustment to an initial anxiety score.
Figure 35F:
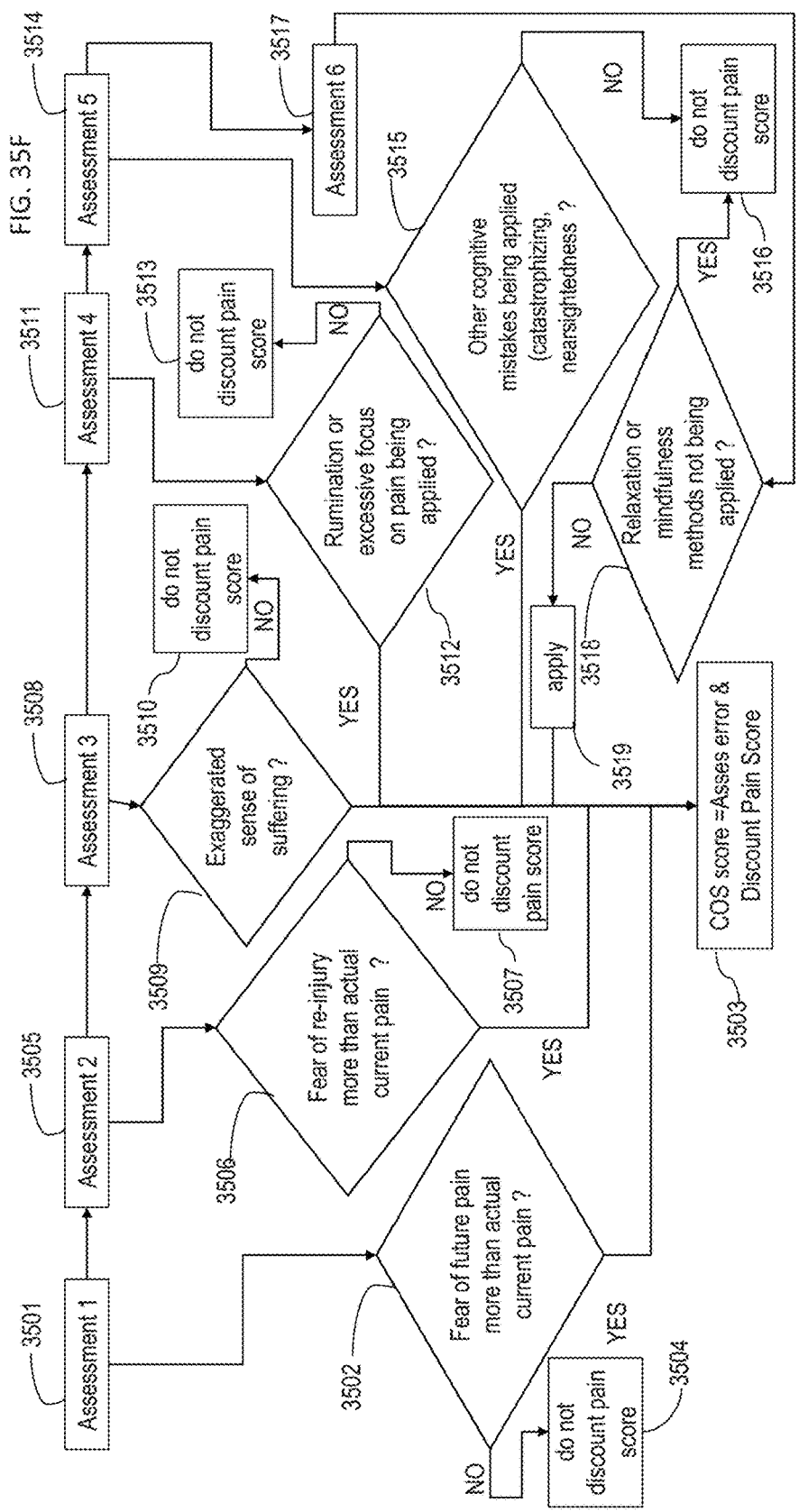
FIG. 35F is an exemplary flow diagram showing a method of determining a cognitive objective stress score from a pain score by applying cognitive skills and methods to make real-time adjustment to an initial pain score.
Figure 35G:
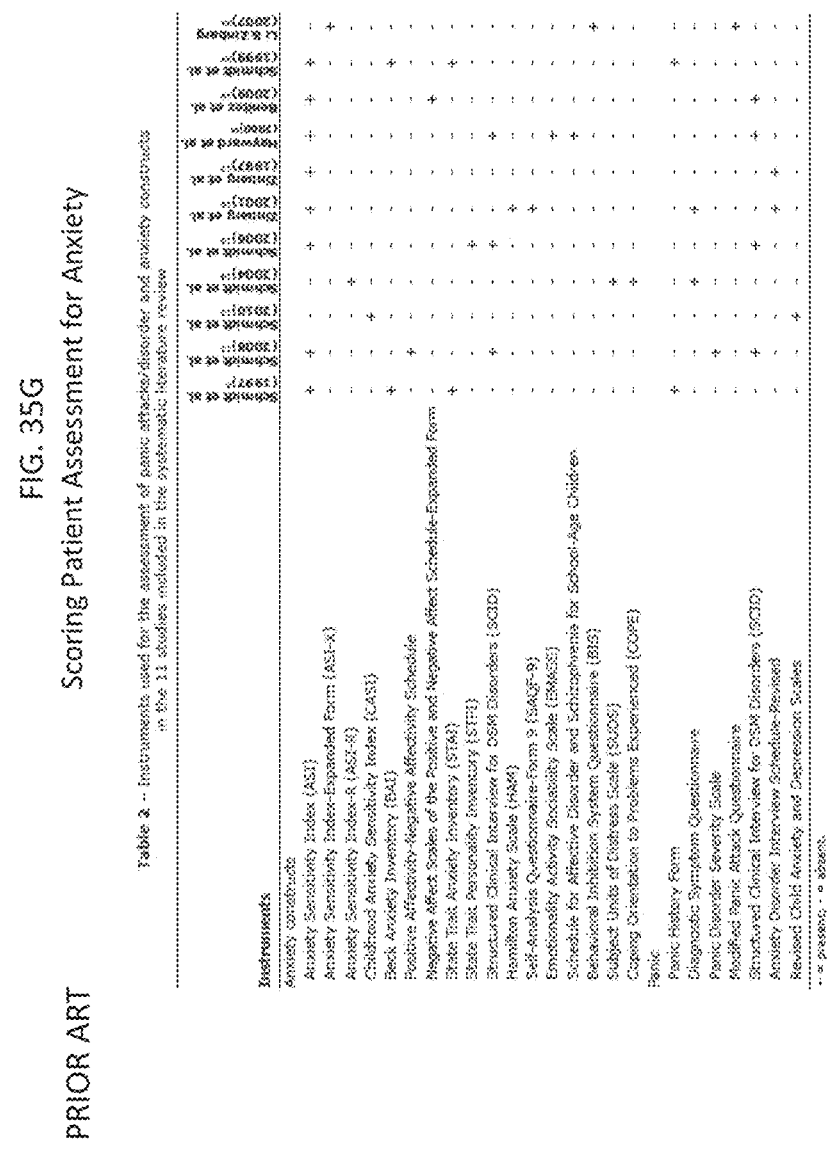

FIG. 35E is an exemplary flow diagram showing a method of determining a cognitive objective stress score from an anxiety score by applying cognitive skills and methods to make real-time adjustment to an initial anxiety score. In assessing anxiety scores, a patient's initial assessment is frequently overwhelmed with emotional thinking and does not get the benefit of a more objective, rational assessment. The field of Cognitive Behavioral Therapy teaches patients various skills and methods of more objectively analyzing emotional experiences such as anxiety, panic, and depression. The present system and method of medication management provides patients with continuous visual feedback that illustrates to the patient that each dose of medication can contribute to medication tolerance and withdrawal. In some exemplary embodiments, the method targets medications which are taken by patients on an "as needed" basis, including certain anxiolytic medications for anxiety disorder. The Cognitive Objective Stress (COS) is a method of applying cognitive behavioral therapy methods to encourage or enforce patients to revise an initial, emotional evaluation of a clinical sign or symptom (e.g., as measured using an unfiltered Anxiety Score) using cognitive methods. By encouraging or requiring the patient to make this assessment prior to self-administering a medication, the patient is asked to more carefully decide if the dose of medication is necessary, once the severity of the clinical symptoms have been reassessed using cognitive-behavioral methods as shown in FIGS. 35E and 35F. The patient may be encouraged by the lower COS score compared to the initial anxiety score. Thus, the patient may become psychologically as well as physiologically less dependent on the medication. The reduced physiologic dependence resulting because of the eliminated doses result pharmacokinetically in less accumulation of the medication in the body, and pharmacodynamically because the lowered concentrations lead to less rapid tolerance. In exemplary embodiments, the method can also be applied to pain management, since in some cases pain can have a subjective and/or emotional component and in some cases a reassessment of a pain score using cognitive methods can reduce medication requirements. In exemplary embodiments, the method can also be applied to more precisely manage "as needed" medications that are used for other disorders that also benefit from cognitive behavioral methods.

In a first assessment, step 3577 control flow proceeds to decision step 3583. In decision step 3853 it is determined if the cognitive error of over personalization (e.g., assessing threats as being directed to the patient personally) is being applied when determining an anxiety score for a situation. If the patient realizes that this cognitive error is being made then control flow proceeds to step 3585, where the magnitude of the effect of this error on the anxiety score is evaluated and the anxiety score is modified and the cognitive objective stress (COS) score is set to the modified anxiety score. If this cognitive error is determined to have no effect on the anxiety score then control flow proceeds to step 3598, where no modification of the score is made.

In a second assessment step 3578, control flow proceeds to decision step 3584. In decision step 3584, it is determined if the cognitive error of exaggeration of consequences or other catastrophizing is being used by the patient when determining an anxiety score for a situation. If, in decision step 3584, the patient realizes that this cognitive error is being made, then control flow proceeds to step 3585, where the magnitude of the effect of this error on the anxiety score is evaluated and the anxiety score is modified and the cognitive objective stress (COS) score is set to the modified anxiety score. If this cognitive error is determined to have no effect on the anxiety score then control flow proceeds to step 3596, where no modification of the score is made.

In a third assessment step 3579, control flow proceeds to decision step 3586. In decision step 3586, it is determined if the cognitive error of exaggerated sense of danger is being used by the patient when determining an anxiety score for a situation. If, in decision step 3586, the patient realizes that this cognitive error is being made, then control flow proceeds to step 3585, where the magnitude of the effect of this error on the anxiety score is evaluated and the anxiety score is modified and the cognitive objective stress (COS) score is set to the modified anxiety score. If this cognitive error is determined to have no effect on the anxiety score then control flow proceeds to step 3599, where no modification of the score is made.

In a forth assessment step 3580, control flow proceeds to decision step 3597. In decision step 3597, it is determined if the cognitive error of rumination or excessive focus on threat is being used by the patient when determining an anxiety score for a situation. If, in decision step 3597, the patient realizes that this cognitive error is being made, then control flow proceeds to step 3585, where the magnitude of the effect of this error on the anxiety score is evaluated and the anxiety score is modified and the cognitive objective stress (COS) score is set to the modified anxiety score. If this cognitive error is determined to have no effect on the anxiety score then control flow proceeds to step 3587, where no modification of the score is made.

In a fifth assessment step 3581, control flow proceeds to decision step 3590. In decision step 3590 it is determined one or more other cognitive errors (e.g., all-or-none thinking, nearsightedness, jumping to conclusions) are being used by the patient when determining an anxiety score for a situation. If, in decision step 3590, the patient realizes that one or more of these cognitive errors are being made, then control flow proceeds to step 3585, where the magnitude of the effect of the specific error on the anxiety score is evaluated and the anxiety score is modified and the cognitive objective stress (COS) score is set to the modified anxiety score. If this cognitive error is determined to have no effect on the anxiety score then control flow proceeds to step 3593, where no modification of the score is made.

In a sixth assessment step 3582, control flow proceeds to decision step 3592. In decision step 3592 it is determined if relaxation or mindfulness methods are not being applied by the patient during the initial determination of the anxiety score for a situation. If, in decision step 3592, the patient has already applied these methods prior to or during the determination of the anxiety score for the situation then control flow proceeds to step 3593, where then anxiety score is not modified for this effect in determining an overall adjusted COS score. If, in decision step 3592 it is determined that the patient has not yet applied relaxation or mindfulness methods then control proceeds to step 3594, where these methods are applied. Subsequently, control flow proceeds to step 3585, where the magnitude of the effect of the specific error on the anxiety score is evaluated and the anxiety score is modified and the cognitive objective stress (COS) score is set to the modified anxiety score.

In certain embodiments, the Cognitive Objective Stress score method is applied to the problem of providing a more objective self-assessment of pain. In such embodiments, the Cognitive Objective Stress score method includes assessment elements which help the patient identify certain cognitive errors which tend to amplify the experience of pain. The method allows the patient to quickly identify these errors prior to each anticipated dose of pain medicine. Using this method, a more rational assessment of pain is performed prior to considering the need for a dose of pain medication. The assessment can produce a decrease in the experiential pain score that may cause the patient to reassess the need for the dose of pain medication. In exemplary embodiments, the method also displays information about the potential effect of the single, anticipated dose of pain medication on the development of tolerance, at the time the patient has taken the Cognitive Objective Stress assessment. In some embodiments, the presentation of the information together with the COS test can make the patient aware of both positive and negative reinforcement motivators toward more judicious analgesic use.

FIG. 35F is an exemplary flow diagram showing a method of determining a cognitive objective stress score from a pain score by applying cognitive skills and methods to make real-time adjustment to an initial pain score. In assessing pain scores, a patient's initial assessment is frequently overwhelmed with emotional thinking and does not get the benefit of a more objective, rational assessment. The field of Cognitive Behavioral Therapy teaches patients various skills and methods of more objectively analyzing emotional experiences such as anxiety, panic, and depression, and pain. The present system and method of medication management provides patients with continuous visual feedback that illustrates to the patient that each dose of medication can contribute to medication tolerance and withdrawal. In some exemplary embodiments, the method targets medications which are taken by patients on an "as needed" basis, including certain analgesic medications for pain. Many of these medications, especially the opioid analgesics, can quickly cause medication tolerance, dependence, and addiction. The Cognitive Objective Stress (COS) is a method of applying cognitive behavioral therapy methods to encourage or enforce patients to revise an initial, emotional evaluation of a clinical sign or symptom (e.g., as measured using an unfiltered Pain Score) using cognitive methods. By encouraging or requiring the patient to make this assessment prior to self-administering a medication, the patient is asked to more carefully decide if the dose of medication is necessary, once the severity of the clinical symptoms have been reassessed using cognitive-behavioral methods. In exemplary embodiments, the method can also be applied to pain management, since in some cases pain can have a subjective and/or emotional component and in some cases a reassessment of a pain score using cognitive methods can reduce medication requirements. In exemplary embodiments, the method can also be applied to more precisely manage "as needed" medications that are used for other disorders that also benefit from cognitive behavioral methods.

In a first assessment, step 3501 control flow proceeds to decision step 3502. In decision step 3502, it is determined if the cognitive error of anticipating future pain rather than treating current actual pain is being applied when determining a pain score for a situation. If the patient realizes that the cognitive error is being made then control flow proceeds to step 3503, where the magnitude of the effect of the error on the pain score is evaluated and the pain score is modified and the COS score is set to the modified or discounted pain score. If this cognitive error is determined to have no effect on the pain score then control flow proceeds to step 3504, where no modification of the score is made.

In a second assessment step 3505, control flow proceeds to decision step 3506. In decision step 3506, it is determined if the cognitive error of unfounded fear of re-injury is being used by the patient when determining a pain score for a situation. If, in decision step 3506, the patient realizes that this cognitive error is being made, then control flow proceeds to step 3503, where the magnitude of the effect of this error on the pain score is evaluated and the anxiety score is modified and the cognitive objective stress (COS) score is set to the modified pain score. If this cognitive error is determined to have no effect on the pain score then control flow proceeds to step 3507, where no modification of the score is made.

In a third assessment step 3508, control flow proceeds to decision step 3509. In decision step 3586 it is determined if the cognitive error of exaggerated sense of suffering is being used by the patient when determining a pain score for a situation. Using cognitive behavior therapy methods, patients can differentiate between pain, which is considered to be a natural part of life, and suffering which can include the amplification of the experience of pain due to maladaptive cognition. If, in decision step 3509, the patient realizes that the cognitive error is being made, then control flow proceeds to step 3503, where the magnitude of the effect of this error on the pain score is evaluated and the pain score is modified and the cognitive objective stress (COS) score is set to the modified pain score. If this cognitive error is determined to have no effect on the pain score then control flow proceeds to step 3510, where no modification of the score is made.

In a forth assessment step 3511, control flow proceeds to decision step 3512. In decision step 3512, it is determined if the cognitive error of rumination or excessive focus on pain is being used by the patient when determining a pain score for a situation. If, in decision step 3512, the patient realizes that this cognitive error is being made, then control flow proceeds to step 3503, where the magnitude of the effect of this error on the pain score is evaluated and the pain score is modified and the cognitive objective stress (COS) score is set to the modified pain score. If this cognitive error is determined to have no effect on the pain score then control flow proceeds to step 3513, where no modification of the score is made.

In a fifth assessment step 3514, control flow proceeds to decision step 3515. In decision step 3515, it is determined if one or more other cognitive errors (e.g., all-or-none thinking, nearsightedness, catastrophizing) are being used by the patient when determining a pain score for a situation. If, in decision step 3515, the patient realizes that one or more of these cognitive errors are being made, then control flow proceeds to step 3503, where the magnitude of the effect of the specific error on the pain score is evaluated and the pain score is modified and the COS score is set to the modified pain score. If the one or more cognitive errors are determined to have no effect on the pain score then control flow proceeds to step 3516, where no modification of the score is made.

In a sixth assessment step 3517, control flow proceeds to decision step 3518. In decision step 3518 it is determined if relaxation or mindfulness methods are not being applied by the patient during the initial determination of the pain score for a situation. If, in decision step 3518, the patient has already applied these methods prior to or during the determination of the pain score for the situation then control flow proceeds to step 3516, where the pain score is not modified for this effect in determining an overall adjusted COS score. If, in decision step 3518 it is determined that the patient has not yet applied relaxation or mindfulness methods then control proceeds to step 3519, where these methods are applied. Subsequently, control flow proceeds to step 3503, where the magnitude of the effect of the specific error on the pain score is evaluated and the anxiety score is modified and the cognitive objective stress (COS) score is set to the modified pain score.

In certain embodiments of the present method of determining the time at which a patient may become dependent on a medication, pharmacokinetic modeling can be used to estimate effect site concentrations of the medication at various times. Pharmacokinetic modeling can be a useful method of estimating effect site concentrations, since the models can generally reflect the first-order, multi-compartment dynamics of medication distribution and elimination from effect site tissues; and can therefore model both the transient and steady-state dynamics. Some embodiments of the present method of determining the time at which a patient may become dependent on a medication can employ other types of models for estimating effect site medication concentrations. For example, a patient's time-weighted average exposure to the medication can be computed and compared to a population-based permissible exposure limit (PEL) to classify the risk of medication dependency. In some embodiments, excursion limits for exposure can also be employed, as is used in determining exposure limits to hazardous substances. In some embodiments of the present method of determining the time at which a patient may become dependent on a medication do not require explicit models of effect site concentration but instead can directly model the risk of medication dependence, for example, as a function of average daily dosage using models derived from population data.

Figure 37:
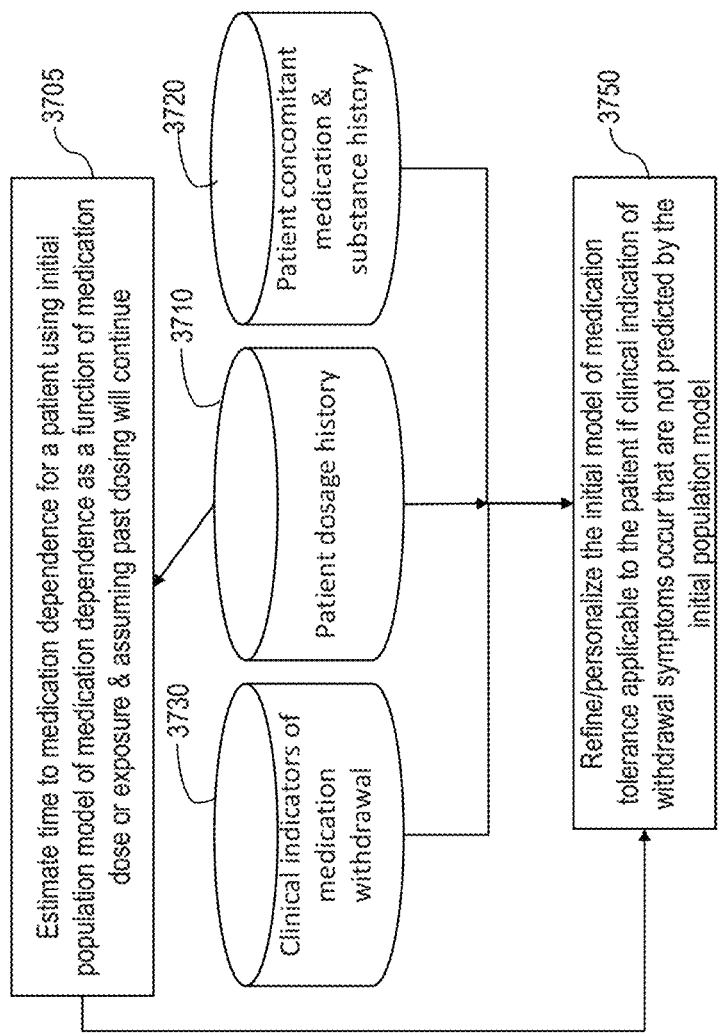
FIG. 37 is an exemplary flow diagram showing a method of estimating a time until a patient may develop medication dependence that does not employ an explicit model of medication effect site concentration.

FIG. 37 is an exemplary flow diagram showing a method of estimating a time until a patient may develop medication dependence that does not employ an explicit model of medication effect site concentration. In a first step 3705, the time until a patient may become dependent on a medication is determined from the patient's past dosing history and a population model of medication dependence which relates the risk of dependence as a function of the dose history. In certain embodiments, the time-weighted average exposure or the daily dose can be used as the basis of the population model, for example, expressing risk of dependence as a function of daily dosage. The patient's individual risk is determined from the population model using the patient's dose history stored in the data store 3710. In a subsequent step 3750, the population model of dependence risk vs medication exposure is personalized to the patient using data representing evidence of clinical indicators of medication withdrawal (e.g., sensor based clinical data, or patient-reported symptoms). Also in step 3750, the population model is personalized to the patient using the patient's history of concomitant or past use of related medications or substances. In embodiments, personalization of the model to an individual patient can include adjustment of individual parameters of the model to reflect the data of 3730 and 3720, or the data of 3730 and 3720 may be used to apply a completely different model to the patient. In some embodiments, the patient dosage history can also be used to personalize the model, as indicated by the personalization step 3750 also accessing data from data store 3710. For example, data representing a pattern of early dose escalation can be used to classify the patient to a dependence model that reflects a higher risk of medication dependence such as early escalation of opioid narcotic dosing indicating a possibility of opioid-induced hyperalgesia and an increased risk of medication dependence. In embodiments, statistical learning methods can be applied to the population and individual patient models of medication tolerance and dependence, as shown in FIG. 36.

Figure 38:
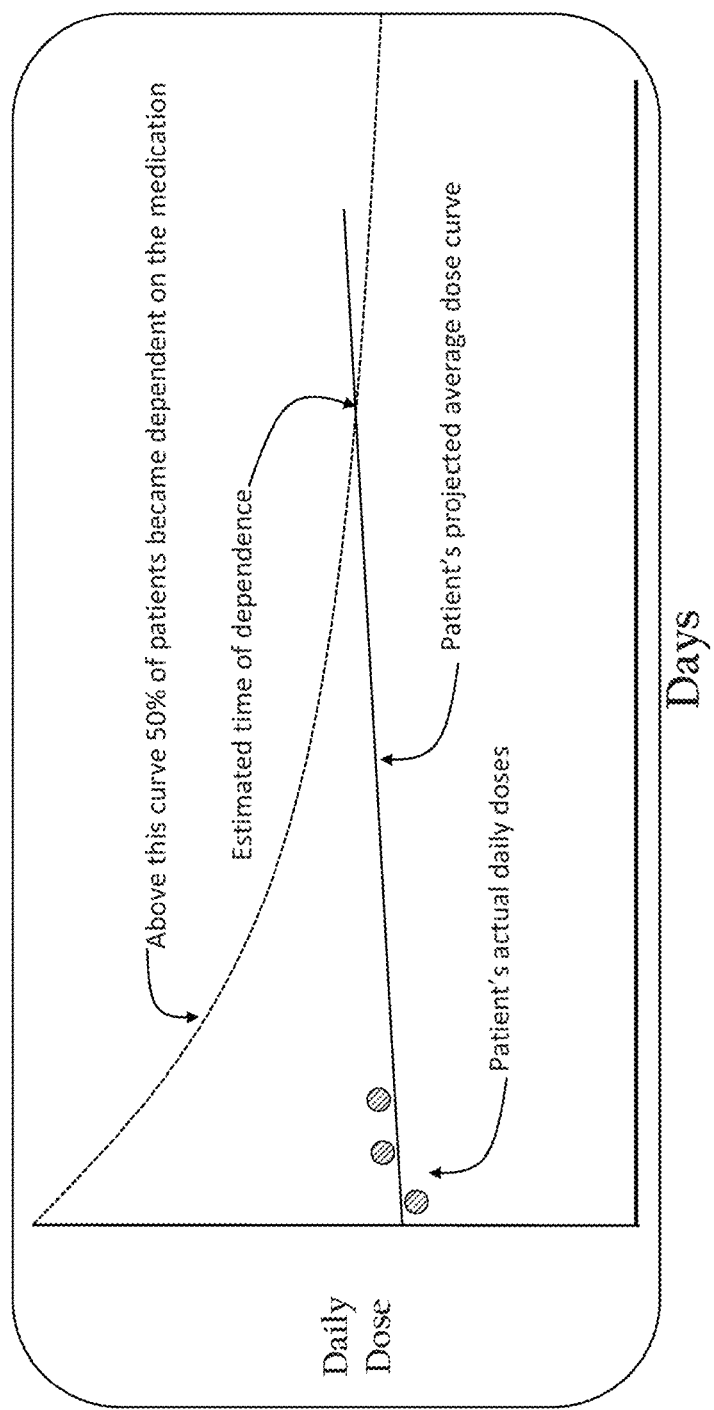
FIG. 38 is an exemplary diagram showing display of a first projected curve giving statistics showing the daily dose of a medication that results in medication dependence in 50% of a population taking the medication as a function of time, and a second curve giving a specific patient's daily dose as a function of time in the past and as a function of the patient's past daily doses, and the intersection of the two curves which is the estimated time at which medication dependence may occur.

FIG. 38 shows a graphic display of impending approach to medication dependence which uses a statistical population model of medication dependence and which does not use a pharmacokinetic estimate of effect site concentration of the medication. FIG. 38 is an exemplary diagram showing display of a first projected curve giving statistics showing the daily dose of a medication that results in medication dependence in 50% of a population taking the medication as a function of time, and a second curve giving a specific patient's daily dose as a function of time in the past and as a function of the patient's past daily doses, and the intersection of the two curves which is the estimated time at which medication dependence may occur.

Medications such as benzodiazepines and opioid narcotics have a high potential for abuse, tolerance, dependence and even addiction. The methods and systems described herein, for managing the dosing of such medications using personalized models of medication tolerance and dependence, in conjunction with an optional locked, paired, controlled single-dose medication dispenser is applicable to medications such as benzodiazepines, opioid narcotics, and other medications that patients tend to over use.

In contrast, other types of medications tend to be under-used by patients. For example, patients who are prescribed antipsychotic medications frequently take less than the prescribed dosage, and may even completely discontinue taking the medication. Known methods exist which attempt to validate medication compliance, but these methods are susceptible to simple exploits and are not able to validate that a patient ingested or otherwise actually took a dose of a medication. For example, several products such as MedSmart® PLUS and eCAP®, MEMSCap® and other existing medication event monitoring systems notify a third party if the patient opened a pill bottle, but cannot verify that the patient ingested the dosage. Video systems such as AiCure (www.aicure.com) can provide video evidence that a patient placed a medication dose inside the mouth, but cannot confirm ingestion. In the case of antipsychotic medications, for example, periodic serum level determinations can be used to monitor medication adherence. However, serum levels for the antipsychotic medications do not accurately reflect steady state effect site tissue levels. In addition, patients can manipulate dosing schedules to falsify the tests. Another method has investigated the use of tracer compounds to improve the precision of serum testing as described in *Limits of Confidence in Tracer Compounds as a Means of Measuring Patient Compliance with Medication*, Shine D, McDonald J. J Clin Pharmacol, 1999; 39:1233-1241, incorporated herein by reference in its entirety. The serum tracer measurements could estimate compliance to within 4-8 doses per month under the best conditions.

The method of medication management described herein provides a technique for monitoring medication adherence that overcomes the limited precision of using tracer compounds that are assayed in the serum. In the method described herein, tracer compounds are detected using a transcutaneous spectrophotometer or other sensor to determine that the tracer compound was ingested or otherwise taken by the patient.

In some embodiments, multi-frequency transcutaneous spectrophotometers are used as a sensor to detect the tracer in the body. The multi-frequency transcutaneous spectrophotometers (e.g., Masimo, Nellcor corporations) are used to make quantitative assessments of blood constituents. The multi-frequency transcutaneous spectrophotometers work by measuring absorption/transmission of light at specific frequencies for targeted constituent molecules. The multi-frequency transcutaneous spectrophotometers are available as inexpensive portable devices. Using advanced signal processing techniques, simultaneous detection and measurement of multiple targeted molecules is possible. Certain exogenous molecules strongly absorb within the portion of the spectrum commonly used for transcutaneous spectrophotometry. For example, methylene blue is a hetrocyclic aromatic compound that is used in intravenous and other forms for therapeutic purposes and as a marker dye. Methylene blue has strong light absorption at frequencies near hemoglobin. Small quantities of Methylene blue can be detected using small, inexpensive transcutaneous spectrophotometers available as pulse oximeters. A single dose of methylene blue is very rapidly detected by a pulse oximeter, which is a transcutaneous spectrophotometer that is used to measure the relative proportions of oxyhemoglobin and hemoglobin. The pulse oximeters are available as very small, portable devices.

In an embodiment, using transcutaneous or other spectrophotometry, a strongly absorbing tracer is added to the medication, and a portable transcutaneous spectrophotometer is used to detect the appearance of the tracer in the body due to ingestion of the medication. In certain aspects, a number of different tracer compounds can be employed in different ratios which generate unique spectral absorption signatures. The ratio of tracers can be varied to create unique absorption spectra (e.g., for different medications or different individual doses of the same medication) using a small number of tracers. In certain aspects, the spectrophotometer is a finger device that has an integrated fingerprint reading sensor which is used to verify that the sensor is in contact with a specific patient at the time of the reading via fingerprint verification circuitry as would be understood by one of ordinary skill in the art.

In some embodiments, tracers with a short effective half-life or distribution half-life, or tracers which show a strong first-pass effect (e.g. short distribution half-life) are employed. For example, in an embodiment, a tracer with a short half-life of initial distribution of approximately five minutes could be used. In such embodiments, the ingestion of the medication and the integrated tracer(s) results in a transient absorption in the finger spectrophotometer caused by a first-pass circulation effect of the tracer(s) being absorbed into the bloodstream and transported to the finger. In the same embodiment, a second tracer with a longer elimination half-life, for example similar to the half-live of the medication (e.g. 24-48 hours) is also added. Detection of the tracer or combination of tracers provides an indication that the patient ingested or otherwise took the corresponding medication at a time prior to the absorption reading. The delay between the ingestion and the absorption reading is determined by the time constants governing gastrointestinal absorption of the tracer(s). In some embodiments, the method described herein provides confirmation that the dose of medication containing the integrated tracer(s) was ingested. The spectrophotographic reading does not provide quantitative information about the dose ingested. However, in some embodiments, the quantity of tracer added to the medication is selected so that partial doses of the medication may not be detected by the transcutaneous spectrophotometer.

In embodiments, individual pills or capsules of the same medication and the same dosage have different tracer agents or different ratios of tracer agents added. In such embodiments, capsules are labeled or otherwise given an identifying mark which identifies the tracer or combination of tracers added. In certain aspects, a patient may take a photograph or other record of the identifying mark prior to ingestion of the medication dosage. The photograph is communicated to a unit (such as the server 4020 or the computing device 508) which also receives readings from the tracer sensor. The tracer sensor readings are correlated with the identifying mark to confirm that the medication was ingested or otherwise taken by the patient. The use of a range of tracers makes it more difficult for patients to falsify the test (e.g., by obtaining and ingesting or otherwise self-administering tracer compounds). In some embodiments, sensor readings are analyzed for the presence of unexpected tracer compounds which could be analyzed for evidence of attempted falsification. The measurement of individual tracers in a mixture of tracers can employ the standard method of using simultaneous equations in the analysis of substances in a mixture. For example, if the sensor is a transcutaneous spectrophotometer the method described in *Simultaneous Equations as a Tool in the Spectrophotometric Analysis of Two Non-interacting Substances in a Binary Mixture*, R. Sanjeev, V. J agannadham, R. Ravi, R. Veda Vrath, Arijit Das, Journal of Laboratory Chemical Education 2013, 1(4): 59-64 incorporated herein can be used.

In some embodiments, the method and system can be can be calibrated to individual patients. For example, if medication therapy is initiated while the patient is an in-patient or otherwise has mediation administered by a caregiver, then tracer sensor readings can be correlated with witnessed administrations. In such observed cases a record of the timing and magnitude of the tracer sensor reading can be used to develop a first-order model of sensor kinetics for the patient. For example, the time constants for a simple one compartment first-order kinetic model could be determined using the sensor readings and the formula:

$$\text{Kelim} = (\ln(\text{Speak}) - \ln(\text{Strough}))/T\text{interval} \quad (1)$$

$$T_{1/2} = 0.693/\text{Kelim} \quad (2)$$

The calibrated model can later be applied to the patient in an unobserved setting. Using short half-live or first-pass tracers, the method is calibrated to provide a reliable verification that a certain dose of a specific medication was taken by the patient. A threshold function for tracer detection can be employed which increases the sensitivity and specificity of the detection, but may provide little information about the actual amount of the tracer/medication taken.

In other embodiments, a long half-life tracer or mixture of tracers is used. Sensor readings can provide quantitative or semi-quantitative information about the steady state level of tracer/medication in the patient's body. In some embodiments, a combination of tracers, some of which have a short effective half-life at the sensor measurement site and some of which have a longer effective half-life at the sensor measurement site are added to the medication. In such embodiments, sensor readings provide information verifying the administration of each dose, through detection of first-pass at the sensor; as well as information about steady state levels.

In certain aspects, the sensor is a transcutaneous spectrophotometer. The sensor may be a mass spectrometer or other sensor capable of detecting or measuring tracers or metabolites of tracers in the patient's exhaled breath. In certain aspects, the sensor may be an ion specific field effect transistors or other sensor which directly detect or measures tracer or medication in tissue. In some embodiments, the sensor can measure tracer accumulation in patient sweat or other bodily fluid that can be sampled or continuously monitored. Herein, the term 'sensor' includes any detecting or measuring circuitry and/or techniques configured to provide a single reading or continuous monitoring. Embodiments are possible in which the sensor is not connected to the patient, but a sampling device (e.g., sweat or other body fluid sampling device) is attached and later analyzed by a sensor that is not collocated with the patient. In some embodiments, the sensor may reside in a central location, for example a mass spectrometer or other sensor for analyzing exhaled compounds, or other sensor may be located at a pharmacy or clinic.

In some embodiments, the individual ingested doses are recorded by an estimation system which employs a pharmacokinetic model that is used to estimates the steady state effect site concentration of the medication. In such embodiments, the model is used to estimate the effect of one or more missed doses and the timing of the missed doses on the effect site concentration of the medication. The pharmacokinetic model can be used to determine an adjusted medication schedule that compensates for missed or delayed doses. For example, after a patient misses several doses of a medication, the estimated effect site concentration may be so low that a full or partial loading dose of a medication can be recommended to reestablish therapeutic levels of the medication.

Figure 39:
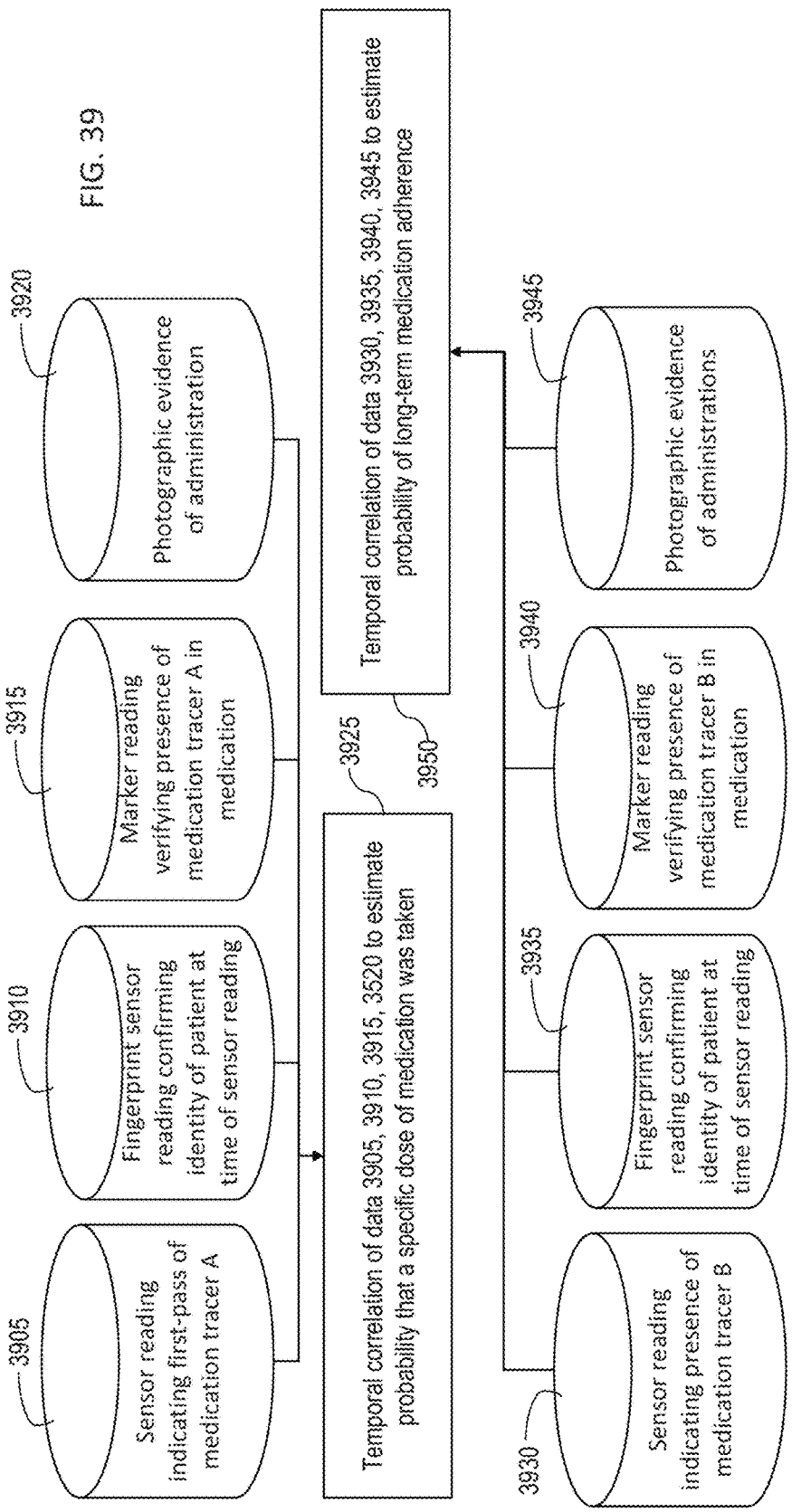
FIG. 39 is an exemplary flowchart illustrating a method using detection of medication tracers to provide evidence that a patient took a specific dose of a medication and evidence that the patient has adhered to a prescribed medication regimen over a long period of time.

FIG. 39 is an exemplary flowchart illustrating a method using detection of medication tracers to provide evidence that a patient took a specific dose of a medication and evidence that the patient has adhered to a prescribed medication regimen over a long period of time. In step 3925, information from data stores is analyzed to estimate the probability that a patient took a specific dose of a medication at a specific time. Information from a first data store 3905 includes sensor information from a sensor detecting a first-pass presence of a medication tracer (e.g., tracer A) having a short half-life at the site of sensor detection. In embodiments, the medication tracer may be a single tracer compound or a mixture of tracer compounds in a specific ratio. The sensor may be a transcutaneous spectrophotometer, an indwelling sensor capable of measuring the short half-life tracer, a sensor configured to detect the tracer or metabolites of the tracer in the patient's breath, a sensor configured to detect the tracer or metabolites of the tracer collected from body fluids, or any other device capable of detecting the tracer in the body tissue or samples of body tissue, fluids, or gases. A second data store 3910 includes information from a fingerprint analyzer that is optionally integrated into the sensor used to generate the sensor data of the first data store 3905. The fingerprint data of the second data store 3910 provides confirmation that the integrated sensor was attached to the patient at a certain time, for example corresponding to the time of a sensor detection of the short half-life tracer A as recorded in the first data store 3905. A third data store 3915 includes a marker reading from an individual dose of a specific medication, indicating that the medication contains the specific tracer, e.g. tracer A. A fourth data store 3920 includes photographic or video evidence that the patient took the medication at a certain time. For example, the fourth data store 3920 may include video of the patient ingesting a specific pill at a specific time. The photographic evidence of the fourth data store 3920 can also be used to confirm the marker reading indicating that the specific pill contains a specific medication marker, as stored in the third data store 3915.

In step 3925, information from data stores 3905, 3910, 3915, and 3920 are correlated to estimate the probability that the patient actually took a specific dose of medication at a specific time. Correlation and determination of the overall probability that the dose was taken may include weighing the data of data stores 3905, 3910, 3915, 3920 based on the known sensitivity and specificity of the methods used to develop the individual elements of information, as well as other metrics indicating the reliability of the individual elements of data in data stores 3905, 3910, 3915, and 3920.

The system may also include a fifth data store 3930, a sixth data store 3935, a seventh data store 3940, and an eighth data store 3950. The fifth data store 3930 includes information about sensor readings indicating presence of medication tracer B. The sixth data store 3935 includes fingerprint sensor reading confirming identity of a patient at the time of readings. The seventh data store 3940 includes marker reading verifying presence of medication tracer B. The eighth data store 3945 includes photographic evidence of administrations.

In step 3950, the information from data stores 3930, 3935, 3940, and 3945 are correlated to estimate the probability that the patient has been in longer-term compliance with the prescribed medication regimen. Correlation and determination of the overall probability of long-term medication adherence may include weighing data from the data stores 3930, 3935, 3940, and 3945 based on the known sensitivity and specificity of the methods used to develop the individual data.

In some embodiments, the determination of step 3925 is made by a server or a client device (e.g., the client device 4110 or the server 4120 of FIG. 40) which analyzes the data from a paired sensor 4130 (or sensor analyzing data from a paired collector) to determine the probability that individual doses were taken, e.g., in step 3925 of FIG. 39, and/or of long-term medication adherence, e.g. in step 3950 of FIG. 30. In any case, the combined information about short term and long-term medication adherence can be made available to a medication prescriber, other caregiver, or accountable care organization through a HIPAA-compliant data transfer protocol such as NCPDP, ASC X12N, CCR/CCD. In embodiments, a medication adherence mobile application may be integrated to existing mobile health or fitness applications 4135, through an application programming interface 4134, allowing use of an existing HIPAA-compliant port to an existing server application 4145 that is already integrated to, and securely communicating with, the existing mobile health or fitness application 4135. Likewise, in embodiments, the server 4120 can be integrated into the existing server application 4145 using an API 4144.

In some embodiments, the server 4120 may make the determination of short-term or long-term incompliance and issue a recommendation of a compensatory adjustment to the patient's medication regime, as shown in FIG. 40 via a HIPAA-compliant issuance from the server to the client device. For example, if the system determines that the patient has failed to take several doses of the medication, then a recommendation for a compensatory loading dose can be issued. Depending on the number of doses missed, the compensatory loading dose may not be a full loading dose, and the size of the compensation can be estimated using a pharmacokinetic model.

In some embodiments, the system can report the medication adherence of populations or specific cohorts, e.g. as the information "Patient Adherence compared to cohorts" shown in FIG. 40, which can be used to encourage greater medication adherence by comparison to peer performance.

I claim:

1. A method of determining whether a patient has taken a dose of medication, the method comprising:
   a) including a first-pass tracer substance with at least one dose of the medication, the first-pass tracer substance being detectable in a body of the patient using a sensor, and the first-pass tracer substance having a short half-life at the site of detection in the body;
   b) determining, using processing circuitry, that the patient has taken the dose of medication when the first-pass tracer substance is detected using the sensor at a time after a scheduled medication administration;
   c) recording, using the processing circuitry, at the scheduled medication administration, at least one image of the patient taking the dose of the medication; and
   d) determining, using the processing circuitry, with an increased probability that the patient has taken the dose of medication when the first-pass tracer substance is detected by the sensor and the detection correlates with the at least one image.

2. The method of claim 1, further comprising:
   verifying that the sensor was in contact with the patient at the time of detecting the first-pass tracer substance.

3. The method of claim 1, wherein the sensor is a transcutaneous spectrophotometer.

4. The method of claim 1, further comprising:
   detecting, using the sensor, the first-pass tracer in an exhaled breath of the patient.

5. The method of claim 1, further comprising:
   detecting, using the sensor, the first-pass tracer when the sensor is connected to the patient at the time the dose was taken.

6. A method of determining whether a patient has taken a dose of medication, the method comprising:
   a) including a first-pass tracer substance with at least one dose of the medication, the first-pass tracer substance being detectable in a body of the patient using a sensor, and the first-pass tracer substance having a short half-life at the site of detection in the body;
   b) determining, using processing circuitry, that the patient has taken the dose of medication when the first-pass tracer substance is detected using the sensor at a time after a scheduled medication administration;
   c) including a second first-pass tracer substance with at least one second dose of the medication, the second tracer substance being detectable in the body of the patient using the sensor, and the second first-pass tracer substance having a short half-life at the site of detection in the body by the sensor;
   d) detecting, using the sensor, the second first-pass tracer substance at a time after the medication dose containing the second first-pass tracer substance should have been taken by the patient;
   e) recording, using the processing circuitry, at the time that the patient takes a dose of the medication, a unique indicator of the dose of medication indicating that the dose of medication contains the first-pass tracer substance or the second first-pass tracer substance;
   f) matching, using the processing circuitry, a result of the detection by the sensor to the unique indicator on the dose of medication; and
   g) outputting, using the processing circuitry, a negative result when the result of the detection and the unique indicator does not match, thus indicating the patient did not take the dose of medication.

7. The method of claim 6, further comprising:
   verifying that the sensor was in contact with the patient at the time of detecting the first-pass tracer substance.

8. A method of determining whether a patient has taken a dose of medication, the method comprising:
   a) including a first-pass tracer substance with at least one dose of the medication, the first-pass tracer substance being detectable in a body of the patient using a sensor, and the first-pass tracer substance having a short half-life at the site of detection in the body;
   b) determining, using processing circuitry, that the patient has taken the dose of medication when the first-pass tracer substance is detected using the sensor at a time after a scheduled medication administration;
   c) detecting, using the sensor, the first-pass tracer substance at a first plurality of times after the medication containing the first-pass tracer substance has been taken by the patient;
   d) including a long half-life tracer substance with at least one dose of the medication, the long half-life tracer substance being detectable in the body using a second sensor, and the long half-life tracer substance having a long half-life at the site of detection in the body;
   e) detecting, using the second sensor, the long half-life tracer substance at a second plurality of times; and
   f) determining, using the processing circuitry, an increased probability that the patient is adhering to a prescribed medication regimen when the number of times the first-pass tracer substance was detected corresponds to a number of scheduled doses during a detection period and the long half-life tracer substance is detected at least a predetermined number of times during the detection period.

* * * * *